US006080748A

United States Patent [19]
Uckun et al.

[11] Patent Number: 6,080,748
[45] Date of Patent: Jun. 27, 2000

[54] THERAPEUTIC USE OF JAK-3 INHIBITORS

[75] Inventors: Fatih M. Uckun, White Bear Lake; Ravi Malavia, Shoreview; Elise A. Sudbeck, St. Paul, all of Minn.

[73] Assignee: Parker Hughes Institute, Roseville, Minn.

[21] Appl. No.: 09/361,491

[22] Filed: Jul. 26, 1999

Related U.S. Application Data

[63] Continuation of application No. 09/263,420, Mar. 5, 1999.
[51] Int. Cl.⁷ .................................................. A61K 31/505
[52] U.S. Cl. .................................................... 514/259
[58] Field of Search ............................................. 514/259

[56] References Cited

U.S. PATENT DOCUMENTS

| | | |
|---|---|---|
| 4,559,157 | 12/1985 | Smith et al. . |
| 4,608,392 | 8/1986 | Jacquet et al. . |
| 4,820,508 | 4/1989 | Wortzman . |
| 4,938,949 | 7/1990 | Borch et al. . |
| 4,992,478 | 2/1991 | Geria . |
| 5,817,674 | 10/1998 | Clemence et al. . |
| 5,916,792 | 6/1999 | Civin et al. .............................. 435/194 |

OTHER PUBLICATIONS

Amir, S. et al.,"An inhibitor of nitric oxide production, $N^G$–nitro–L–arginine–methyl ester, improves survival in anaphylactic shock", *Eur. J. Pharmacol.*, vol. 203, No. 1, pp. 125–127 (Oct. 2, 1991).

Apgar, J., "Increased degranulation and phospholipase $A_2$, C, and D activity in RBL cells stimulated through FcεR1 is due to spreading and not simply adhesion", *J. Cell. Sci.*, vol. 110, No. 6, pp. 771–780 (Mar. 1997).

Blank, U. et al., "Complete structure and expression in transfected cells of high affinity IgE receptor", *Nature*, vol. 337, No. 6203, pp. 187–189 (Jan. 12, 1989).

Böhm, H–J, "The development of a simple empirical scoring function to estimate the binding constant for a protein–ligand complex of known three–dimensional structure", *J. Comput. Aided Mol. Des.*, vol. 8, No. 3, pp. 243–256 (Jun. 1994).

Buckley, R. et al., "Human severe combined immunodeficiency: Genetic, phenotypic, and functional diversity in one hundred eight infants", *J. Pediatr.*, vol. 130, No. 3, pp. 378–387 (Mar. 1997).

Chen, C–L., et al., "Pharmacokinetics and Biologic Activity of the Novel Mast Cell Inhibitor, 4–(3'–Hydroxyphenyl)–amino–6,7–dimethoxyquinazoline in Mice", *Pharmaceutical Research*, vol. 16, No. 1, pp. 117–122 (Jan. 1999).

Costello, P. et al., "Critical role for the tyrosine kinase Syk in signalling through the high affinity IgE receptor of mast cells", *Oncogene*, vol. 13, No. 12, pp. 2595–2605 (Dec. 19, 1996).

Danial, N. et al., "Jak–STAT Signaling Induced by the v–able Oncogene", *Science*, vol. 269, No. 5232, pp. 1875–1877 (Sep. 29, 1995).

Darnell, Jr. J. et al., "Jak–STAT Pathways and Transcriptional Activation in Response to IFNs and Other Extracellular Signaling Proteins", *Science*, vol. 264, pp. 1415–1421 (Jun. 3, 1994).

Deckert, M. et al., "Coordinated Regulation of the Tyrosine Phosphorylation of Cbl by Fyn and Syk Tyrosine Kinases", *J. Biol. Chem.*, vol. 273, No. 15, pp. 8867–8874 (Apr. 10, 1998).

Dvorak, A. et al., "Effects of Interleukin–3 With or Without the c–kit Ligand, Stem Cell Factor, on the Survival and Cytoplasmic Granule Formation of Mouse Basophils and Mast Cells in Vitro", *Am. J. Pathol.*, vol. 144, No. 1, pp. 160–170 (Jan. 1994).

Endo, T. et al., "A new protein containing an SH2 domain that inhibits JAK kinases", *Nature*, vol. 387, pp. 921–924 (Jun. 26, 1997).

Fusaki, N. et al., "Interaction between Sam68 and Src Family Tyrosine Kinases, Fyn and Lck, in T Cell Receptor Signaling", *J. Biol. Chem.*, vol. 272, No. 10, pp. 6214–6219 (Mar. 7, 1997).

Galli, S., "Seminars in Medicine of the Beth Israel Hospital, Boston: New Concepts About the Mast Cell", *New Eng. J. Med.*, vol. 328, No. 4, pp. 257–265 (Jan. 28, 1993).

Ghosh, S. et al., "α–Cyano–β–hydorxy–β–methyl–N–[4–(trifluoromethoxy)phenyl] Propenamide: An Inhibitor of the Epidermal Growth Factor Receptor Tyrosine Kinase with Potent Cytotoxic Activity against Breast Cancer Cells", *Clin. Cancer Res.*, vol. 4, No. 11, pp. 2657–2668 (Nov. 1998).

Goodman, P. et al., "Role of Tyrosine Kinases in Induction of the c–jun Proto–oncogene in Irradiated B–Lineage Lymphoid Cells", *J. Biol. Chem.*, vol. 273, No. 28, pp. 17742–17748 (Jul. 10, 1998).

Gordon, J. et al., "Mast cells as a source of both preformed and immunologically inducible TNF–α/cachetin", *Nature*, vol. 346, No. 6281, pp. 274–276 (Jul. 19, 1990).

Gurniak, C. et al., "Murine JAK3 Is Preferentially Expressed in Hematopoietic Tissues and Lymphocyte Precursor Cells", *Blood*, vol. 87, No. 8, pp. 3151–3160 (Apr. 15, 1996).

Hamawy, M. et al., "Protein tyrosine phosphorylation as a mechanism of signalling in mast cells and basophils", *Cellular Signalling*, vol. 7, No. 6, pp. 535–544 (Aug. 1995).

Hanissian, S. et al., "Jak3 Is Associated with CD40 and Is Critical for CD40 Induction of Gene Expression in B Cells", *Immunity*, vol. 6, No. 4, pp. 379–387 (Apr. 1997).

Hirasawa, N. et al., "A Requirement for Syk in the Activation of the Microtubule–associated Protein Kinase/Phospholipase $A_2$ Pathway by FcεR1 Is Not Shared by a G Protein–coupled Receptor", *J. Biol. Chem.*, vol. 270, No. 18, pp. 10960–10967 (May 5, 1995).

Hoffman, S. et al., "JAK3 Maps to Human Chromosome 19p12 within a Cluster of Proto–oncogenes and Transcription Factors", *Genomics*, vol. 43, No. 1, pp. 109–111 (Jul. 1, 1997).

(List continued on next page.)

*Primary Examiner*—James H. Reamer
*Attorney, Agent, or Firm*—Merchant & Gould P.C.

[57] ABSTRACT

Inhibitors of JAK3 kinase for the treatment of allergy inhibit mast cell degranulation an dmediator release.

11 Claims, 18 Drawing Sheets

OTHER PUBLICATIONS

Hogan, A. et al., "Markers of Mast Cell Degranulation", *Methods: A Companion to Methods in Enzymology*, vol. 13, No. 1, pp. 43–52 (Sep. 1997).

Hubbard, S. et al., "Crystal structure of the tyrosine kinase domain of the human insulin receptor", *Nature*, vol. 372, No. 6508, pp. 746–754 (Dec. 1994).

Hubbard, S., "Crystal structure of the activated insulin receptor tyrosine kinase in complex with peptide substrate and ATP analog", *The EMBO Journal*, vol. 16, No. 18, pp. 5572–5581 (Sep. 15, 1997).

Ihle, J. et al., "Jaks and Stats in signaling by the cytokine receptor superfamily", *Trends in Genetics*, vol. 11, No. 2, pp. 69–74 (Feb. 1995).

Ihle, J., "Janus kinases in cytokine signalling", *Phil. Trans. R. Soc. Lond. B*, vol. 351, No. 1336, pp. 159–166 (Feb. 29, 1996).

Irani, A. et al., "Detection of $MC_T$ and $MC_{TC}$ Types of Human Mast Cells by Immunohistochemistry Using New Monoclonal Anti–tryptase and Anti–chymase Antibodies", *J. Histochem. Cytochem.*, vol. 37, No. 7, pp. 1509–1515 (1989).

Johnston, J. et al., "Phosphorylation and activation of the JAK–3 Janus Kinase in response to interleukin–2", *Nature*, vol. 370, No. 6485, pp. 151–153 (Jul. 14, 1994).

Johnston, J. et al., Interleukins 2, 4, 7, and 15 Stimulate Tyrosine Phosphorylation of Insulin Receptor Substrates and 1 and 2 in T Cells, *J. Biol. Chem.*, vol. 270, No. 48, pp. 28527–28530 (Dec. 1, 1995).

Kumar, A. et al., "Structural organization and chromosomal mapping of JAK3 locus", *Oncogene*, vol. 13, No. 9, pp. 2009–2014 (Nov. 7, 1996).

Lavens–Phillips, S. et al., "The effect of tyrosine kinase inhibitors on IgE–mediated histamine release from human lung mast cells and basophils", *Inflamm. Res.*, vol. 47, No. 3, pp. 137–143 (Mar. 1998).

Leonard, W., "STATs and cytokine specificity. Several STATs transduce signals and activate genes only in response to select cytokines—will all STATs prove so specific?", *Nature Medicine*, vol. 2, No. 9, pp. 968–969 (Sep. 1996).

Levy, D., "The House that JAK/STAT Built", *Cytokine & Growth Factor Reviews*, vol. 8, No. 1, pp. 81–90 (Mar. 1997).

Liu, F. et al., "Monoclonal Dinitrophenyl–specific Murine IgE Antibody: Preparation, Isolation, and Characterization", *J. Immunol.*, vol. 124, No. 6, pp. 2728–2737 (Jun. 1980).

Mahajan, S. et al., "Src Family Protein Tyrosine Kinases Induce Autoactivation of Bruton's Tyrosine Kinase", *Mol. Cell. Biol.*, vol. 15, No. 10, pp. 5304–5311 (Oct. 1995).

Mahajan, S. et al., "Rational Design and Synthesis of a Novel Anti–leukemic Agent Targeting Bruton's Tyrosine Kinase (BTK), LFM–A13 [α–Cyano–β–Hydroxy–β–Methyl–N–(2,5–Dibromophenyl)Propenamide]", *J. Biol. Chem.*, vol. 274, No. 14, pp. 9587–9599 (Apr. 2, 1999).

Malaviya, R. et al., "Reversible Translocation of 5–Lipoxygenase in Mast Cells upon IgE/Antigen Stimulation", *J. Biol. Chem.*, vol. 268, No. 7, pp. 4939–4944 (Mar. 5, 1993).

Malaviya, R. et al., "Mast Cell Phagocytosis of FimH–Expressing Enterobacteria", *J. Immunol.*, vol. 152, 1907–1914 (1994).

Malaviya, R. et al., "Mast Cell Degranulation Induced by Type 1 Fimbriated *Escherichia coli* in Mice", *J. Clin. Invest.*, vol. 93, pp. 1645–1653 (Apr. 1994).

Malaviya, R. et al., "Histamine in Human Epidermal Cells is Induced by Ultraviolet Light Injury", *J. Invest. Dermatol.*, vol. 106, No. 4, pp. 785–789 (Apr. 1996).

Malaviya, R. et al., "Mast cell modulation of neutrophil influx and bacterial clearance at sites of infection through TNF–α", *Nature*, vol. 381, No. 6577, pp. 77–80 (May 2, 1996).

Matsuda, T. et al., "Association of p72 Tyrosine Kinase With Stat Factors and Its Activation by Interleukin–3, Interleukin–6, and Granulocyte Colony–Stimulating Factor", *Blood*, vol. 83, No. 12, pp. 3457–3461 (Jun. 15, 1994).

Millard, P. et al., "Immunoglobulin E Receptor Cross–linking Induces Oscillations in Intracellular Free Ionized Calcium in Individual Tumor Mast Cells", *J. Biol. Chem.*, vol. 264, No. 33, pp. 19730–19739 (Nov. 25, 1989).

Miyajima, I. et al., "Systemic Anaphylaxis in the Mouse Can Be Mediated Largely through $IgG_1$ and $Fc_\gamma RIII$", *J. Clin. Invest.*, vol. 99, No. 5, pp. 901–914 (Mar. 1997).

Miyazaki, T. et al., "Coupling of the IL2 Receptor Complex with Non–receptor Protein Tyrosine Kinases", *Cancer Surveys*, vol. 27, pp. 25–40, *Cell Signalling*, published by Cold Spring Harbor Laboratory Press (1996).

Mohammadi, M. et al., "Structure of the FGF Receptor Tyrosine Kinase Domain Reveals a Novel Autoinhibitory Mechanism", *Cell*, vol. 86, pp. 577–587 (Aug. 23, 1996).

Mohammadi, M. et al., "Structures of the Tyrosine Kinase Domain of Fibroblast Growth Factor Receptor in Complex with Inhibitors", *Science*, vol. 276, No. 5314, pp. 955–960 (May 9, 1997).

Moriya, K. et al., "ER–27319, an acridone–related compound, inhibits release of antigen–induced allergic mediators from mast cells by selective inhibitin of Fcε receptor I–mediated activation of Syk", *Proc. Natl. Acad. Sci. USA*, vol. 94, No. 23, pp. 12539–12544 (Nov. 11, 1997).

Narla, R. et al., "4–(3'–Bromo–4'hydroxylpenyl)–amino–6, 7–dimethoxyquinazoline: A Novel Quinazoline Derivative with Potent Cytotoxic Activity against Human Glioblastoma Cells", *Clin. Cancer Res.*, vol. 4, No. 6, pp. 1405–1414 (Jun. 1998).

Nelson, B. et al., "A Membrane–Proximal Region of the Interleukin–2 Receptor $\gamma_c$ Chain Sufficient for Jak Kinase Activation and Induction of Proliferation in T Cells", *Mol. Cell. Biol.*, vol. 16, No. 1, pp. 309–317 (Jan. 1996).

Nomoto, Y. et al., "Studies on Cardiotonic Agents. I. Synthesis of Some Quinazoline Derivatives", *Chem. Pharm. Bull.*, vol. 38, No. 6, pp. 1591–1595 (Jun. 1990).

Nosaka, T. et al., "Defective Lymphoid Development in Mice Lacking Jak3", *Science*, vol. 270, No. 5237, pp. 800–802 (Nov. 3, 1995).

Oettgen, H. et al., "Active anaphylaxis in IgE–deficient mice", *Nature*, vol. 370, No. 6488, pp. 367–370 (Aug. 4, 1994).

Oliver, J. et al., "Inhibition of Mast Cell FcεR1–mediated Signaling and Effector Function by the Syk–selective Inhibitor, Piceatannol", *J. Biol. Chem.*, vol. 269, No. 47, pp. 29697–29703 (Nov. 25, 1994).

Ozawa, K. et al., "$Ca^{2+}$–dependent and $Ca^{2+}$–independent Isozymes of Protein Kinase C Mediate Exocytosis in Antigen–stimulated Rat Basophilic RBL–2H3 Cells", *J. Biol. Chem.*, vol. 268, No. 3, pp. 1749–1756 (Jan. 25, 1993).

Riedy, M. et al., "Genomic Sequence, Organization, and Chromosomal Localization of Human JAK3", *Genomics*, vol. 37, No. 1, pp. 57–61 (Oct. 1, 1996).

Riske, F. et al., "High Affinity Human IgE Receptor (FcεRI): Analysis of Functional Domains of the α–Subunit with Monoclonal Antibodies", *J. Biol. Chem.*, vol. 266, No. 17, pp. 11245–11251 (Jun. 15, 1991).

Rolling, C. et al., "JAK3 associates with the human Interleukin 4 receptor and is tyrosine phosphorylated following receptor triggering", *Oncogene*, vol. 10, No. 9, pp. 1757–1761(May 4, 1995).

Rolling C. et al., "IL4 and IL13 receptors share the γc chain and activate STAT6, STAT3 and STAT5 proteins in normal human B cells", *FEBS Letters*, vol. 393, No. 1, pp. 53–56 (Sep. 9, 1996).

Safford, M. et al., [published erratum appears in *Exp. Hematol.*, vol. 25, No. 7, p. 650 (Jul. 1997)] "JAK3: Expression and mapping to chromosome 19p12–13.1", *Exp. Hematol.*, vol. 25, No. 5, pp. 374–386 (May 1997).

Scharenberg, A. et al., "Early Events in Mast Cell Signal Transduction", *Chem. Immunol.*, vol. 61, pp. 72–87, "Marone G (ed): Human Basophils and Mast Cells: Biological Aspects" (Copyright 1995 by S. Karger AG, Basel, Switzerland).

Scharenberg, A. et al., "Reconstitution of interactions between tyrosine kinases and the high affinity IgE receptor which are controlled by receptor clustering", *The EMBO Journal*, vol. 14, No. 14, pp. 3385–3394 (Jul. 17, 1995).

Sharfe, N. et al., "Jak3 activation in human lymphocyte precursor cells", *Clin. Exp. Immunol.*, vol. 108, No. 3, pp. 552–556 (Jun. 1997).

Sicheri, F. et al., "Crystal structure of the Src family tyrosine kinase HcK", *Nature*, vol. 385, pp. 602–609 (Feb. 13, 1997).

Thomis, D. et al., "Defects in B Lymphocyte Maturation and T Lymphocyte Activation in Mice Lacking Jak3", *Science*, vol. 270, No. 5237, pp. 794–797 (Nov. 3, 1995).

Thomis, D. et al., "The role of Jak3 in lymphoid development, activation, and signaling", *Curr. Opin. Immunol.*, vol. 9, No. 4, pp. 541–547 (Aug. 1997).

Tortolani, P. et al., "Regulation of JAK3 Expression and Activation in Human B Cells and B Cell Malignancies", *J. Immunol.*, vol. 155, pp. 5220–5226 (1995).

Uckun, F. et al., "Biotherapy of B–Cell Precursor Leukemia by Targeting Genistein to CD19–Associated Tyrosine Kinases", *Science*, vol. 267, No. 5199, pp. 886–891 (Feb. 10, 1995).

Uckun, F. et al., "Physical and Functional Interactions between Lyn and p34$^{cdc2}$ Kinases in Irradiated Human B–cell Precursors", *J. Biol. Chem.*, vol. 271, No. 11, pp. 6389–6397 (Mar. 15, 1996).

Uckun, F. et al., "BTK as a Mediator of Radiation–Induced Apoptosis in DT–40 Lymphoma B Cells", *Science*, vol. 273, No. 5278, pp. 1096–1100 (Aug. 23, 1996).

Uckun, F. et al., "Cytotoxic Activity of Epidermal Growth Factor–Genistein against Breast Cancer Cells", *Clin. Cancer Res.*, vol. 4, No. 4, pp. 901–912 (Apr. 1998).

Vassilev, A. et al., "Bruton's Tyrosine Kinase as an Inhibitor of the Fas/CD95 Death–inducing Signaling Complex", *J. Biol. Chem.*, vol. 274, No. 3, pp. 1646–1656 (Jan. 15, 1999).

Verbsky, J. et al., "Expression of Janus Kinase 3 in Human Endothelial and Other Non–lymphoid and Non–myeloid Cells", *J. Biol. Chem.*, vol. 271, No. 24, pp. 13976–13980 (Jun. 14, 1996).

Villa, A. et al., "Monocyte Function in a Severe Combined Immunodeficient Patient With a Donor Splice Site Mutation in the Jak3 Gene", *Blood*, vol. 88, No. 3, pp. 817–823 (Aug. 1, 1996).

Wei, Y. et al., "Contribution of Macrophages to Immediate Hypersensitivity Reaction", *J. Immunol.*, vol. 137, No. 6, pp. 1993–2000 (Sep. 15, 1986).

Wong, A. et al., "Stimulation of Leukotriene Production and Membrane Translocation of 5–Lipoxygenase by Cross–Linking of the IgE Receptors in RBL–2H3 Cells", *Biochemistry*, vol. 31, No. 16, pp. 4046–4053 (Apr. 28, 1992).

Xia, H.–Z. et al., "Effect of Recombinant Human IL–4 on Tryptase, Chymase, and Fcε Receptor Type I Expression in Recombinant Human Stem Cell Factor–Dependent Fetal Liver–Derived Human Mast Cells", *J. Immunol.*, vol. 159, No. 6, pp. 2911–2921 (Sep. 15, 1997).

Yamauchi, T. et al., "Growth Hormone and Prolactin Stimulate Tyrosine Phosphorylation of Insulin Receptor Substrate–1, –2, and –3, Their Association with p85 Phosphatidylinositol 3–Kinase (PI3–kinase), and Concomitantly PI3–kinase Activation via JAK 2 Kinase", *J. Biol. Chem.*, vol. 273, No. 25, pp. 15719–15726 (Jun. 19, 1998).

Yin, T. et al., "Interleukin–9 Induces Tyrosine Phosphorylation of Insulin Receptor Substrate–1 via JAK Tyrosine Kinases", *J. Biol. Chem.*, vol. 270, No. 35, pp. 20497–20502 (Sep. 1, 1995).

Zhong, Z. et al., "Stat3 and Stat4: Members of the family of signal transducers and activators of transcription", *Proc. Natl. Acad. Sci. USA*, vol. 91, No. 11, pp. 4806–4810 (May 24, 1994).

Zhu, D–M. et al., "Calphostin C Triggers Calcium–dependent Apoptosis in Human Acute Lymphoblastic Leukemia Cells", *Clin. Cancer Res.*, vol. 4, No. 12, pp. 2967–2976 (Dec. 1998).

| Protein Tyrosine Kinase | Residue at Region A | Residue at Region B | Residue at Region C | Residue at Region D | Residue at Region E | Residue at Region F |
|---|---|---|---|---|---|---|
| JAK3 | Pro906 | Tyr904 | Leu905 | Met902 | Ala966 | Asp912 |
| JAK2 | Pro933 | Tyr931 | Leu932 | Met929 | Gly993 | Asp939 |
| JAK1 | Pro948 | Phe946 | Leu947 | Met944 | Gly1008 | Glu954 |
| BTK | Ala101 | Tyr99 | Met100 | Thr97 | Ser161 | Asn107 |
| SYK | Glu342 | Met340 | Ala341 | Met338 | Ser403 | Lys348 |
| HCK | Ala342 | Phe340 | Met341 | Ala342 | Ala403 | Asp348 |
| LYN | Ala323 | Tyr321 | Met322 | Ala323 | Ala384 | Asp329 |
| IRK | Ala1080 | Leu1078 | Met1079 | Met1076 | Gly1149 | Ser1086 |

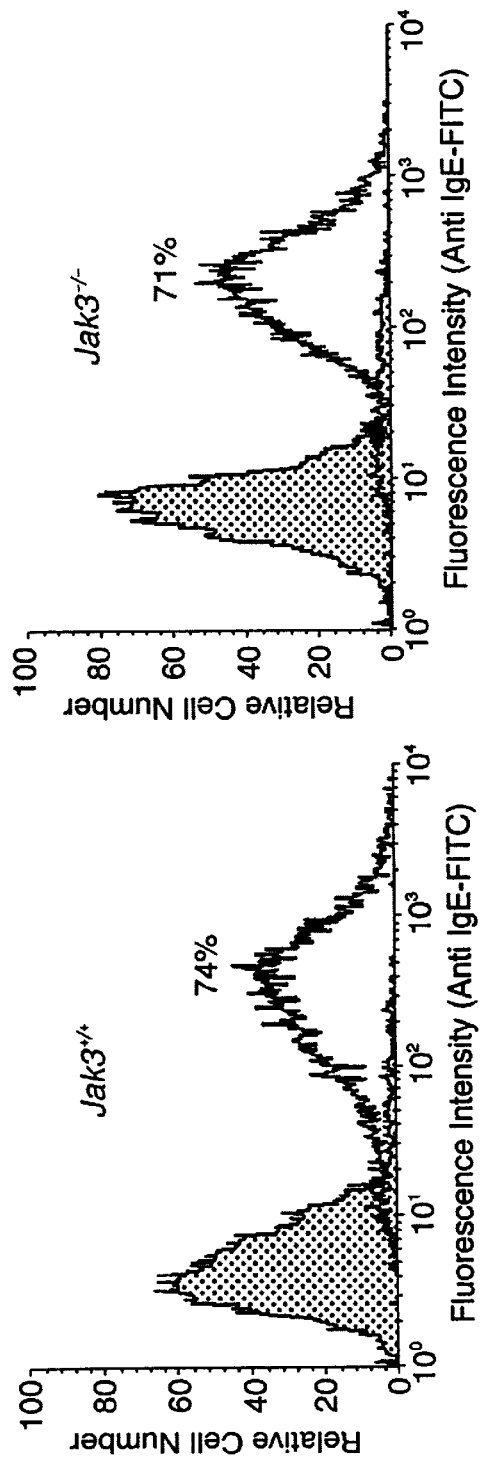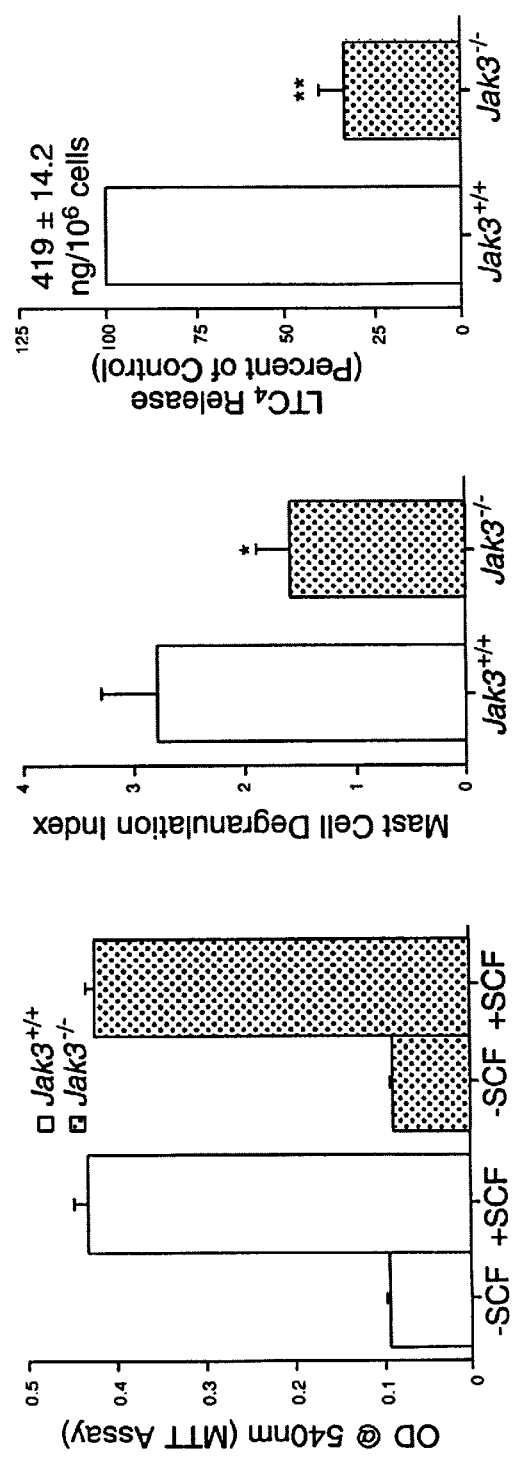

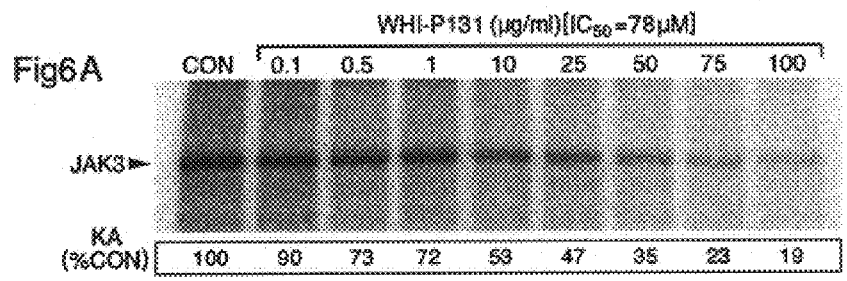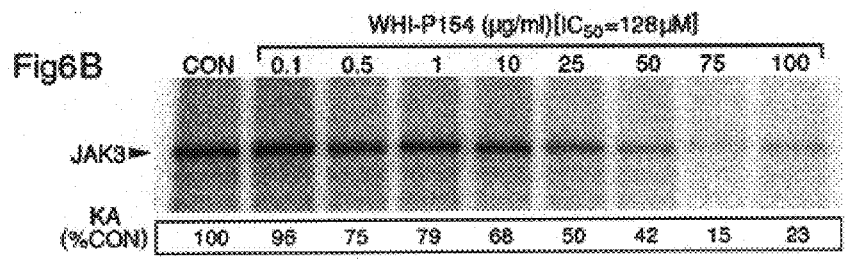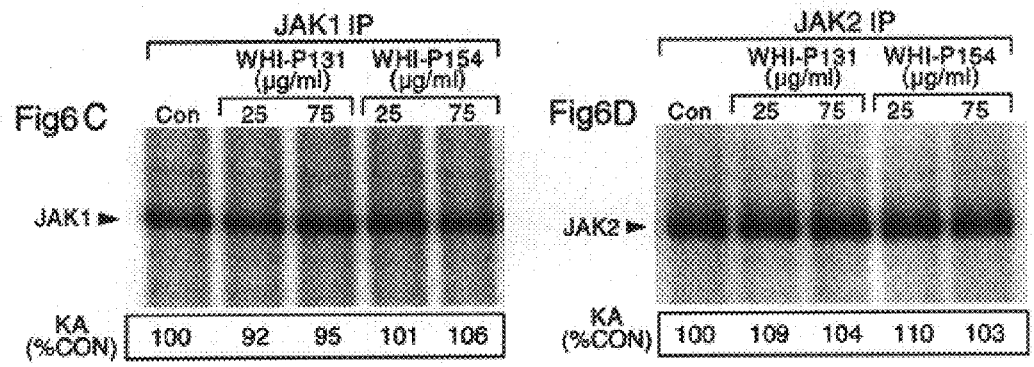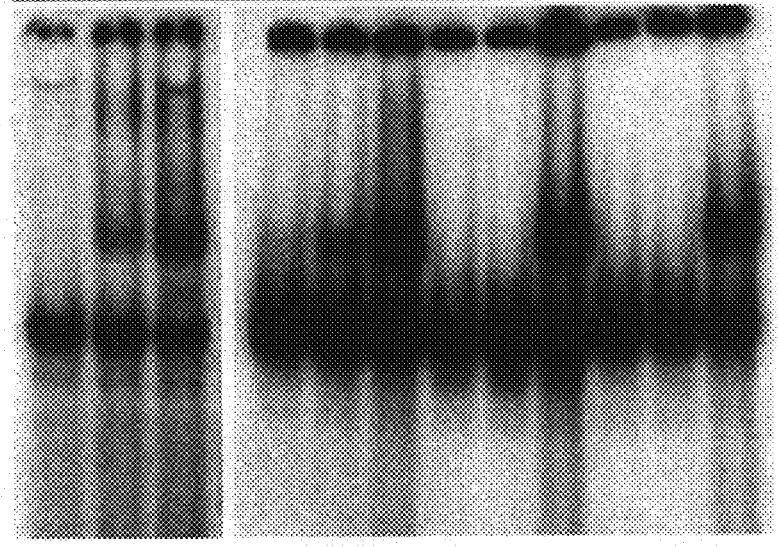
Fig6A, Fig6B, Fig6C, Fig6D, Fig6E

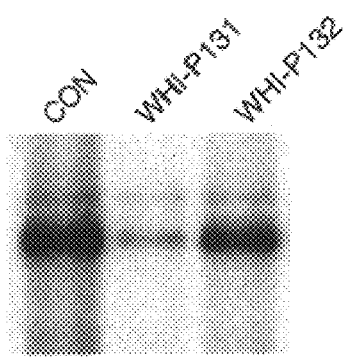
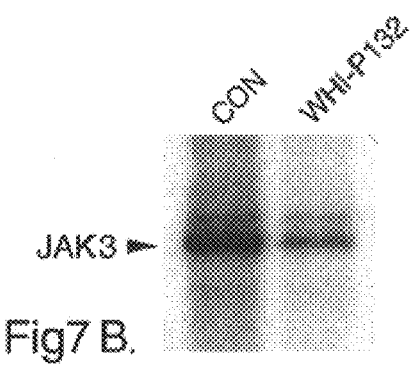
Fig 7A.  Fig 7B.
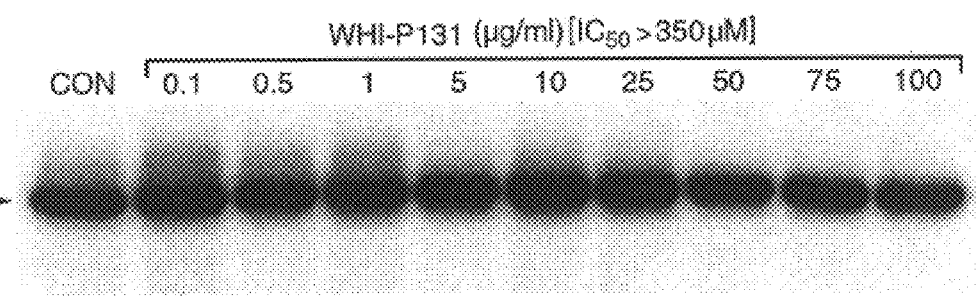
Fig 7C.
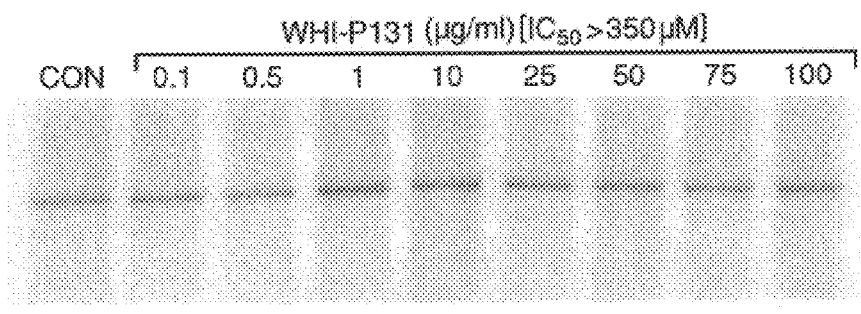
Fig 7D.
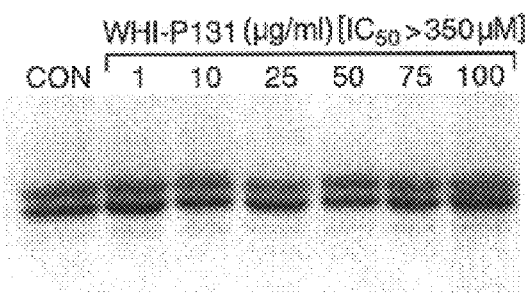
Fig 7E.
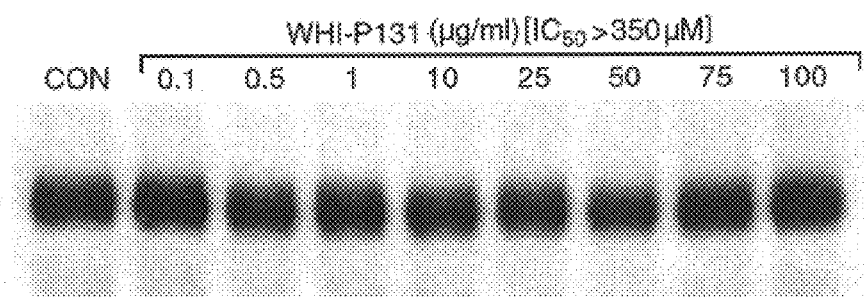
Fig 7F.

Vehicle

Vehicle

P258

P258

P131

P131

P112

P112

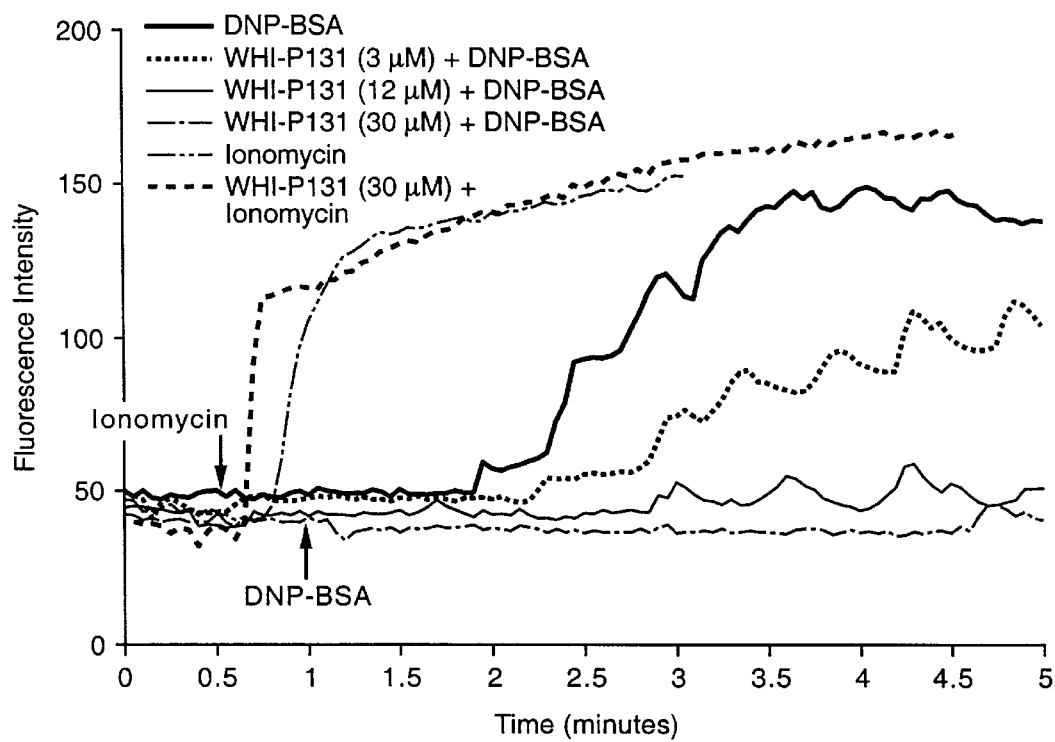

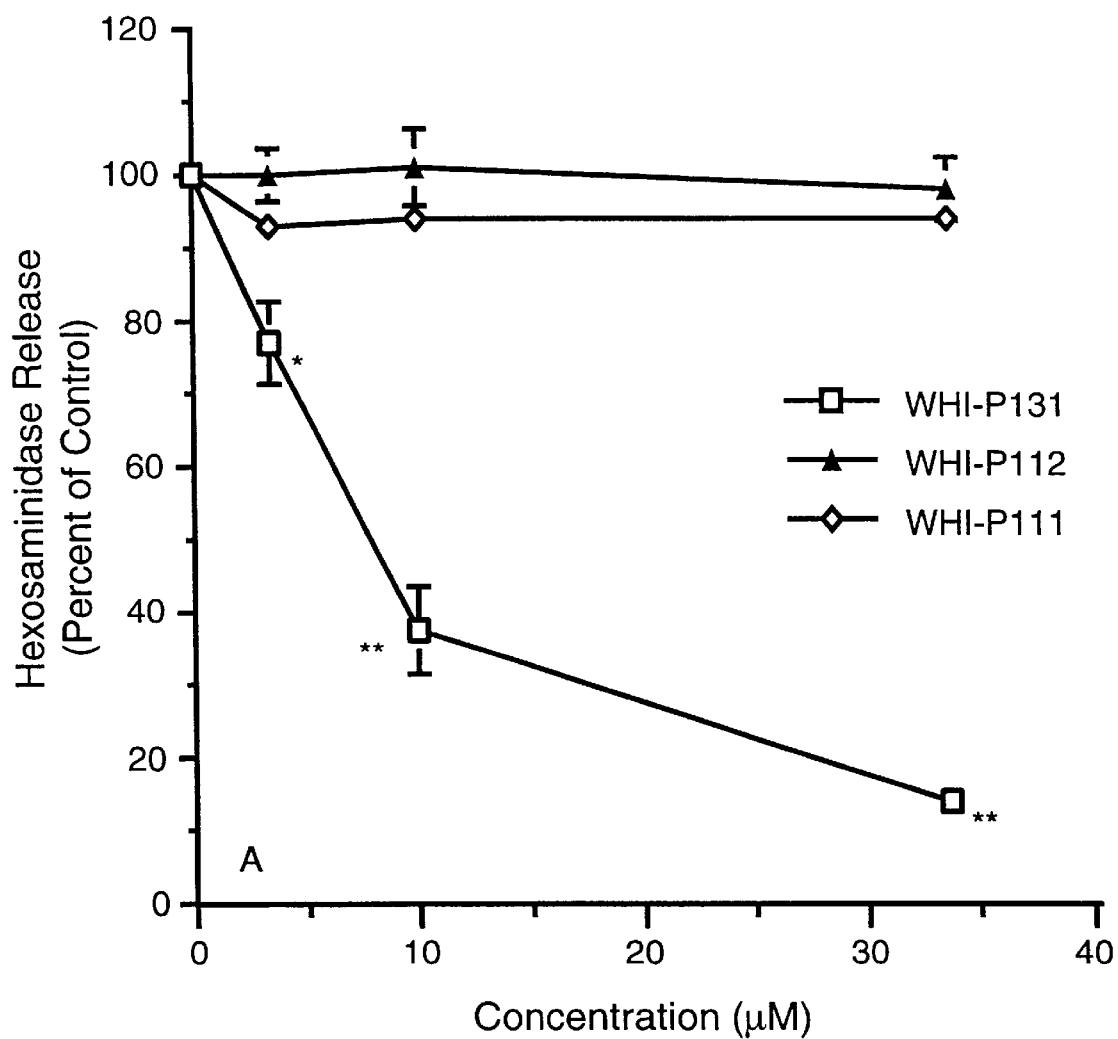

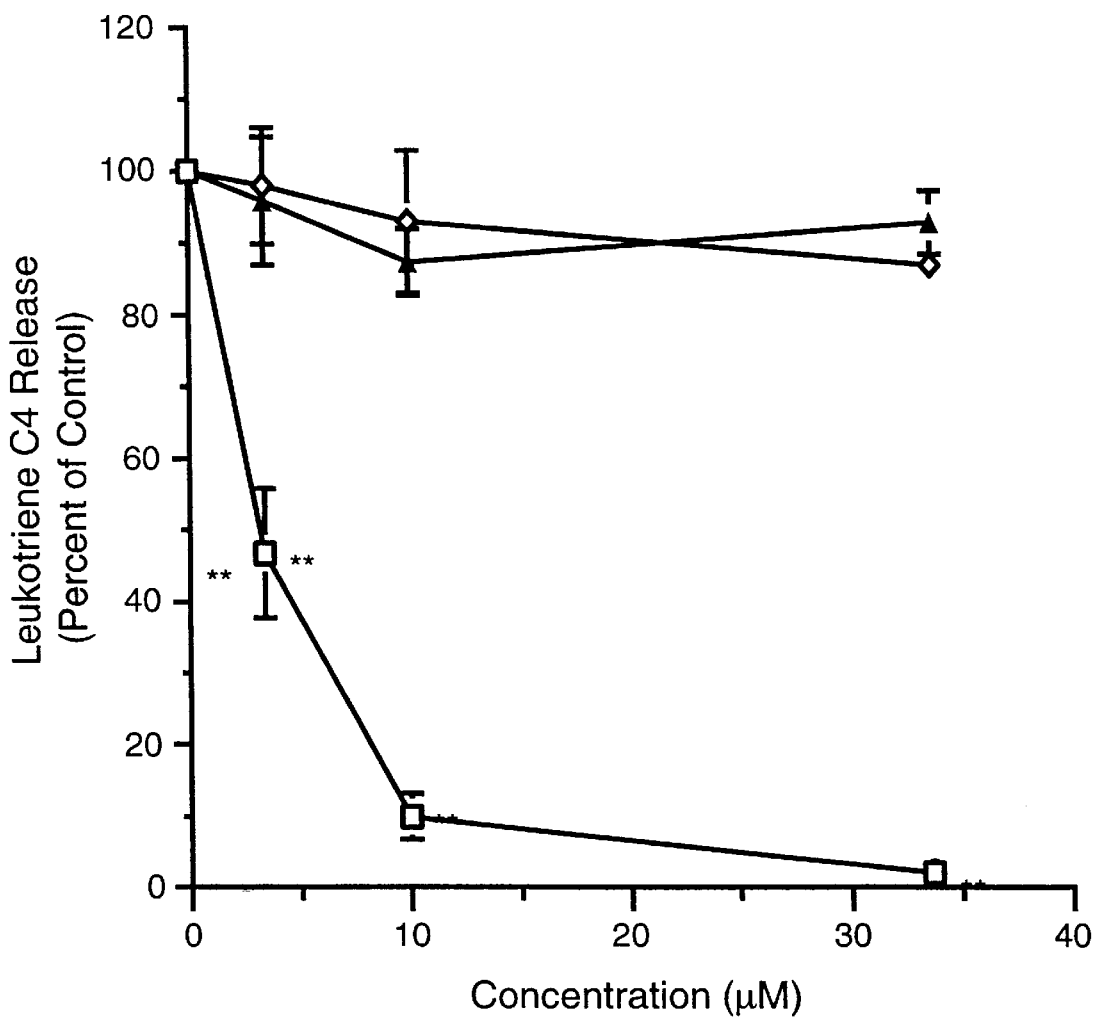

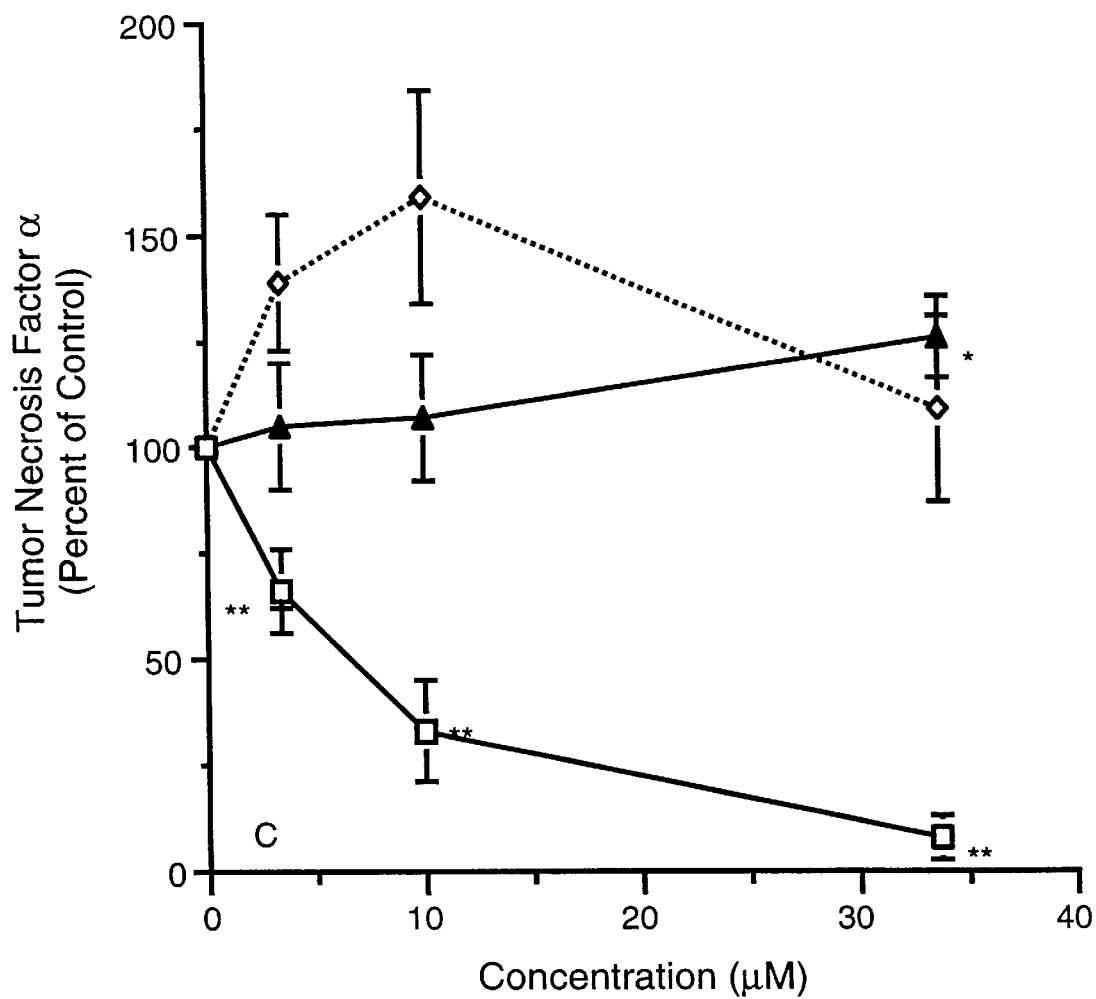

$V_C = 0.51$ L/kg
$C_{max} = 85.6$ μM
$t_{1/2}\beta = 2.1$ h
AUC = 29.8 μM x h $V_C = 0.29$ L/kg
$C_{max} = 57.7$ μM
$t_{1/2}\beta = 1.9$ h
AUC = 28.2 μM x h
F = 94.6%

B.1 Con    B.2 Vehicle→ IgE/Ag    B.3 WHI-P131 →IgE/Ag

C.1 Con    C.2 Vehicle→ IgE/Ag    C.3 WHI-P131 →IgE/Ag

THERAPEUTIC USE OF JAK-3 INHIBITORS

This application is a Continuation of application Ser. No. 09/263,420, filed Mar. 5, 1999, which application(s) are incorporated herein by reference.

This is a continuation of a U.S. Pat. No. 1,263,420, filed Mar. 5, 1999.

FIELD OF THE INVENTION

This invention relates to compositions and methods for inhibiting JAK-3 tyrosine kinase and to the treatment of allergic disorders by administering an inhibitor of Janus Kinase 3 (JAK3).

BACKGROUND OF THE INVENTION

Signal transducers and activators of transcription (STAT) are pleiotropic transcription factors which mediate cytokine-stimulated gene expression in multiple cell populations (D. A. Levy, Cytokine Growth Factor Rev., 8:81 (1997)). All STAT proteins contain a DNA binding domain, a Src homology 2 (SH2) domain, and a transactivation domain necessary for transcriptional activation of target gene expression. Janus kinases (JAK), including JAK1, JAK2, Tyk, and JAK3, are cytoplasmic protein tyrosine kinases (PTKs) which play pivotal roles in initiation of cytokine-triggered signaling events by activating the cytoplasmic latent forms of STAT proteins via tyrosine phosphorylation on a specific tyrosine residue near the SH2 domain (See J. N. Ihle et al., Trends Genet., 11: 69 (1995); J. E. Darnell et al., Science, 265: 1415 (1994); J. A. Johnston et al., Nature, 370: 1513 (1994)). Tyrosine phosphorylated STAT proteins dimerize through specific reciprocal SH2-phosphotyrosine interactions and translocate from the cytoplasm to the nucleus where they stimulate the transcription of specific target genes by binding to response elements in their promoters (See W. J. Leonard, Nature Medicine, 2: 968 (1996); Z. Zhong et al., PNAS USA, 91:4806 (1994) Darnell et al., Science, 264:1415 (1994)).

Among the four members of the JAK family, JAK3 is abundantly expressed in lymphoid cells and plays an important role in normal lymphocyte development and function, as evidenced by qualitative and quantitative deficiencies in the B-cell as well as T-cell compartments of the immune system of JAK3-deficient mice (T. Nosaka et al., Science, 270:800 (1995): D. C. Thomas et al., Science, 270:794 (1995)) and development of severe combined immunodeficiency in JAK3-deficient patients (R. H. Buckley et al., J Pediatr., 130: 379 (1997)). Besides lymphoid cells, non-lymphoid cells, including monocytes, megakaryocytes, endothelial cells, cancers cells, and, as descibed herein, mast cells also express JAK3, but no information is currently available regarding the physiologic function of JAK3 in these non-lymphoid cell populations. See, D. C. Thomas et al., Curr. Opin. Immunol., 9: 541 (1997); J. N. Hile, Philos. Trans. R. Soc. Lond B Biol. Sci., 351: 159 (1996); J. W. Verbsky et al. J Biol. Chem., 271: 13976 (1996).

JAK-3 maps to human chromosome 19p12-13.1. A cluster of genes encoding protooncogenes and transcription factors is also located near this region. JAK-3 expression has been demonstrated in mature B-cells as well as B-cell precursors. JAK-3 has also been detected in leukemic B-cell precursors and lymphoma B-cells. The physiological roles for JAK-3 have been borne out through targeted gene disruption studies in mice, the genetic analysis of patients with severe combined immunodeficiency, and biochemical studies of JAK-3 in cell lines. A wide range of stimuli result in JAK-3 activation in B-cells, including interleukin 7 and interleukin 4. The B-cell marker CD40 constitutively associates with JAK-3 and ligation of CD40 results in JAK-3 activation, which has been shown to be mandatory for CD40-mediated gene expression. Constitutive activity of JAK-3 has been observed in v-abl transformed pre-B cells and coimmuno-precipitations show that v-abl physically associates with JAK-3, implicating JAK-3 in v-abl induced cellular transformation. See J. N. Ihle, Philos Trans R Soc Lond B Biol Sci, 351: 159 (1996); W. J. Leonard et al., Cytokine Growth Factor Rev., 8: 81 (1997); M. C. Riedy et al., Genomics, 37: 57 (1996); M. G. Safford et al. [published erratum appears in Exp. Hematol., 1997 July;25(7):650] Exp. Hematol., 25: 374 (1997); A. Kumar et al., Oncogene, 13: 2009 (1996); S. M. Hoffman et al., Genomics, 43: 109 (1997); P. J. Tortolani et al., J. Immunol., 155: 5220 (1995); N. Sharfe et al., Clin. Exp. Immunol., 108: 552 (1997); C. B. Gurniak et al., Blood, 87: 3151 (1996); C. Rolling et al., Oncogene, 10: 1757 (1995); C. Rolling et al., FEBS Lett., 393: 53 (1996); S. H. Hanissian et al., Immunity, 6: 379 (1997); N. N. Daniel et al., Science, 269: 1875 (1995).

Acute allergic reactions, also known as immediate (type I) hypersensitivity reactions, including anaphylaxis with a potentially fatal outcome, are triggered by three major classes of proinflammatory mediators, namely preformed, granule-associated bioactive amines (e.g. histamine, serotonin) and acid hydrolases (e.g., $\beta$-hexosaminidase), newly synthesized arachidonic acid metabolites [e.g., leukotriene (LT) $C_4$, prostaglandin $D_2$, and platelet activating factor], and a number of proinflammatory vasoactive cytokines (e.g., tumor necrosis factor [TNF] $\alpha$, interleukin-6 [IL-6]) (R. Malavija et al., J Biol. Chem., 268: 4939 (1983); S. J. Galli et al., N. Eng. J Med., 328: 257 (1993)). These proinflammatory mediators are released from sensitized mast cells upon activation through the antigen-mediated crosslinking of their high affinity cell surface IgE receptors/ Fc$\epsilon$ RI (M. J. Hamany et al., Cellular Signaling, 7: 1535 (1995); A. M. Scharenberg et al., Clin. Immunol., G. Marone ed., Basel, Karger (1995) at p. 72)). IgE receptor/Fc$\epsilon$RI is a multimeric receptor with $\alpha$, $\beta$, and homodimeric $\gamma$ chains (See U. Blank et al., Nature, 337, 187 (1989)). Both $\beta$- and $\gamma$ subunits of the IgE receptor/Fc$\epsilon$RI contain ITAMs (Immunoreceptor Tyrosine-based Activation Motifs) which allow interaction with protein tyrosine kinases (PTK) and PTK substrates via their SH2 domains (See, N. Hirasawa et al., J Biol. Chem., 270: 10960 (1995)). The engagement of IgE receptors by antigen triggers a cascade of biochemical signal transduction events, including activation of multiple PTK (S. E. Lavens-Philips et al., Inflamm. Res., 47: 137 (1998)). The activation of PTK and subsequent tyrosine phosphorylation of their downstream substrates have been implicated in the pathophysiology of type I hypersensitivity reactions (See K. Moriya et al., PNAS USA, 94: 12539 (1997) Costello et al., Oncogene, 13:2595 (1996)).

Treatments for allergy are generally aimed at three possible components: 1) avoidance or reduced exposure to the allergen, which can be very difficult especially in case of children; 2) allergen immunotherapy, which only works for some allergens, and which is frequently ineffective; and 3) pharmacotherapy (medication), which is the most effective treatment. Allergy medication either should prevent the release of allergy causing chemicals such as histamine from mast cells, or stop the response of histamine on the tissues. Most currently available medications are anti-histamines. Usually in case of allergy and asthma, doctors prescribe second generation anti-histamines such as loraitidine (Claratin®), fexofenidine (Allegra®) or leukotriene synthesis inhibitors such as zafirlukast (Accolate®) and zileutron (Zyflo®). Because the airway is more sensitive to leukotrienes produced by a number of inflammatory cells, anti-leukotriene agents are usually more effective for asthmatic conditions.

Although the second generation antihistamines are as effective as the older ones (Benadryl and Chlortrimeton) they have two potential problems. First, these drugs only counteract the effect of histamine released by mast cells in the body, which are responsible for many but not all the symptoms of allergy. Therefore, anti-histamines are very effective in decreasing the itching, sneezing, and nasal secretions, but do not provide relief from nasal stuffiness and late phase allergic reactions. A number of inflammatory mediators other than histamine, such as leukotrienes and a number of vasoactive cytokines, are also released by mast cells and basophils. These inflammatory mediators remain unaffected by anti-histamines and contribute significantly to the patho-physiology of allergy and asthma. Sometimes a combination of anti-allergic and inflammatory drugs works better, but at the same time these combinations cause adverse side effects. Secondly, in more severe allergic reactions (anaphylaxis), anti-histamines do not have therapeutic effect.

Until recently, therapy for asthma was based on the drug theophylline. This drug is an excellent, time proven, time tested drug but had numerous side effects. In the 1980's short acting beta-adrenergic compounds were introduced. In the 1990's asthma therapy shifted, so that asthmatic patients started taking cortocosteroids, cromolyn, and theophylline in different combinations. Recently three anti-leukotriene drugs: Accolate, Zyflo and Singulair, were introduced in to the U.S. market for the treatment of asthma. These medications either block the release of leukotrienes (Zylec) or block their effect on tissues (Accolate). Each is available in tablet form to be taken 2 to 4 times a day. Although leukotriene inhibitors do not inhibit early phase of allergy or asthmatic reaction, they are found to improve pulmonary function and asthma symptoms and significantly reduce requirement of beta-agonist by reducing the bronchial hyper-responsiveness.

Despite the above described advances in therapy, there is currently a need for therapeutic agents and methods that are useful for preventing or reducing immediate (type I) hypersensitivity reactions, including anaphylaxis and other allergic reactions.

SUMMARY OF THE INVENTION

We have now discovered that IgE/antigen induced degranulation and mediator release are substantially reduced in Jak3$^{-/-}$ mast cells from JAK3-null mice that generated by targeted disruption of Jak3 gene in embryonic stem cells. Furthermore, treatment of mouse, rat, as well as human mast cells with 4-(4'-hydroxylphenyl)-amino-6,7-dimethoxyquinazoline) (WHI-P131), a rationally designed potent and specific inhibitor of JAK3 inhibited degranulation and proinflammatory mediator release after IgE receptor/FcεRI crosslinking. In vivo administration of this potent JAK3, inhibitor prevented mast cell degranulation and development of cutaneous, as well as systemic, fatal anaphylaxis in mice. Thus, JAK3 plays a pivotal role in IgE receptor/FcεRI mediated mast cell responses both in vitro and in vivo.

Treatment with JAK-3 inhibitor reduces and/or prevents allergic reactions and anaphylxis. JAK-3 inhibition results in reduced or inhibited degranulation and proinflamatory mediator release. Thus, targeting JAK-3 with a specific inhibitor provides a new and effective treatment and prevention for mast-cell mediated allergic reactions.

The invention provides a method comprising inhibiting mast cell activation or degranulation by contacting the mast cell (in vitro or in vivo) with an effective amount of a JAK-3 inhibitor.

The invention also provides a therapeutic method comprising treating a pathology wherein mast cell activation or degranulation is implicated and inhibition of mast cell activation or degranulation is desired by administering a JAK-3 inhibitor to a mammal (e.g. a human) in need of such therapy.

The invention also provides substances that are effective to inhibit JAK-3 for use in medical therapy, preferably for use in treating conditions associated with mast cell activation or degranulation, such as immediate hypersensitivity reactions. The invention also provides the use of a substance that inhibits JAK-3 for the manufacture of a medicament for the treatment of a condition that is associated with mast cell activation or degranulation.

The invention also provides novel compounds of formula I, as disclosed hereinbelow, as well as processes and intermediates useful for their preparation.

BRIEF DESCRIPTION OF THE FIGURES

FIG. 1A is a model of the JAK3 kinase domain showing molecular surface of protein (blue) and catalytic (ATP binding) site (yellow).

FIG. 1B is a ribbon representation (Ca backbone) of the homology model of the JAK3 kinase domain. The WHI-P131 molecule is shown as a space filling model in the catalytic site of JAK3.

FIG. 1C is a close-up view of the catalytic site of the JAK3 model with a docked inhibitor. WHI-P131 (green). Residues and inhibitor are shown as space filling atoms. The solvent-exposed opening of the catalytic site has dimensions to allow a relatively planar inhibitor to enter and bind to JAK3. The opening of the pocket is defined by residues Pro906, Ser907, Gly908, Asp912, Arg953, Gly829, Leu828, and Tyr904 (blue residues). The far wall deep inside the pocket is lined with Leu905 (backbone portion), Glu903, Met902, Lys905, and Asp967 (pink residues), and the floor of the pocket is lined by Leu905 (side chain portion), Val884, Leu956, and Ala966 (yellow residues). Residues defining the roof of the pocket include Leu828, Gly829, Lys830, and Gly831 (uppermost blue residues). Prepared using InsightII program.

FIG. 2A is a model of unoccupied space in the catalytic (ATP binding) site of a JAK3 homology model. Shown in green is the binding site for ATP and the most likely binding site for dimethoxyquinazoline inhibitors. The green kinase active site region represents a total volume of approximately 530 Å$^3$. Modeling studies showed that an inhibitor or a portion of an inhibitor with significant binding to this region would occupy a volume less than 530 Å$^3$ and have molecular dimensions compatible with the shape of the binding site region. Other regions near the binding site which show measurable unoccupied volume are shown in royal blue, pink, yellow, and light blue. These binding regions are either unavailable to inhibitor molecules (royal blue) or represent regions just large enough to occupy solvent molecules (pink, yellow, light blue). A model showing the inhibitor WHI-P131 docked into the catalytic site is shown in white, superimposed on the green region.

FIG. 2B is a model of the catalytic site of JAK3 with docked quinazolines WHI-P131 (multicolor), WHI-P132

(pink), and WHI-P154 (yellow). Each compound fits into the binding site, but WHI-P132 (shown to be inactive against JAK3 in biological assays). WHI-P 132 lacks an OH group in a location to bind with Asp967. WHI-P131 and WHI-P154, with OH groups at the C4' position of the phenyl ring, are able to form a favorable interaction with Asp967 of JAK3, which may contribute to their enhanced inhibition activity.

Figure 2A:
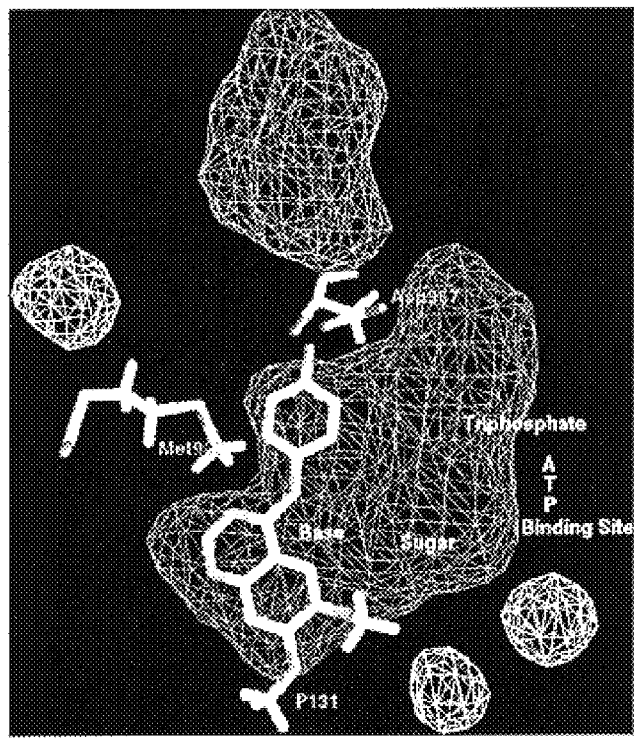
FIGS. 2A–2C.
Figure 2B:
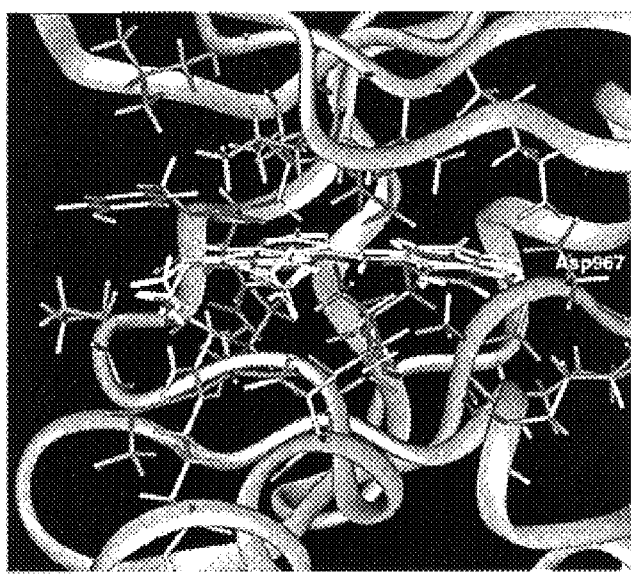
Figure 2C:
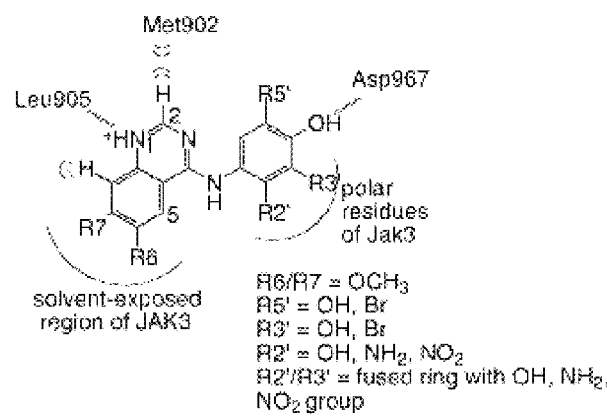

FIG. 2C is a diagram showing features of dimethoxy quinazoline derivatives which are predicted to aid binding to JAK3 catalytic site.

Figures 3A, 3B:
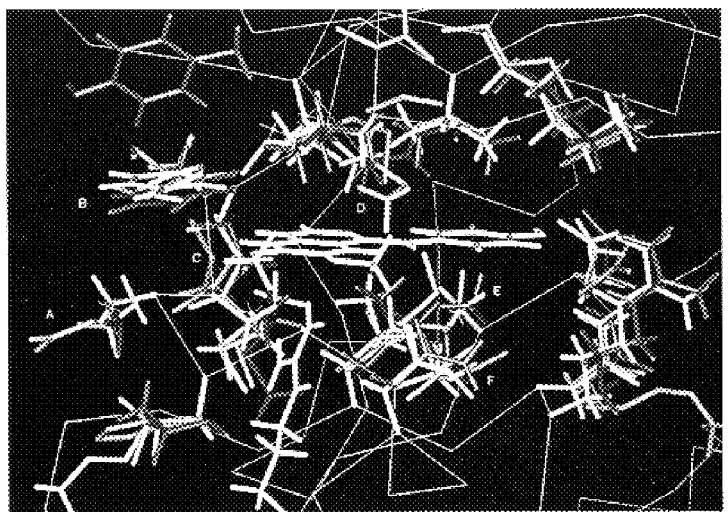

FIGS. 3A–3B. FIG. 3A shows a structural comparison of nonconserved residues in the catalytic sites of 5 different protein tyrosine kinases: JAK3 (pink), BTK (red), SYK (light blue), IRK (dark blue), and HCK (yellow). Residues within 5 Å of the docked JAK3 inhibitor, WHI-P131 (white), are shown as rod-shaped side chains. The C alpha backbone of JAK3 is shown as a thin pink line, for perspective. Regions A to F correspond to areas containing nonconserved residues in the catalytic site (see B and the Examples below). Crystal structure coordinates of HCK (Sicheri et. al., 1997, Nature 385:602–609) and IRK (Hubbard et. al., 1997, Nature 372:746–754), and homology models of JAK3, BTK (Mahajan et. al., 1999, J Biol. Chem., in press) and SYK were used for the structural analysis.

FIG. 3B shows nonconserved residues in the catalytic sites of 8 different protein tyrosine kinases. Regions A–F refer to locations in the catalytic site which are illustrated in A.

Figures 4A, 4B:
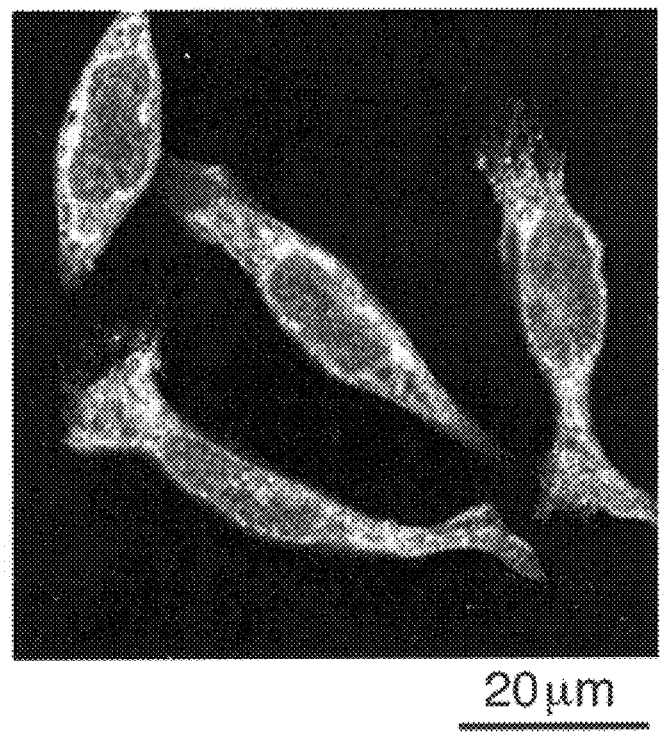

FIGS. 4A–4B show expression and activation of JAK3 in mast cells after IgE receptor crosslinking.

In FIG. 4A, RBL-2H3 mast cells were stained with a polyclonal anti-JAK3 antibody and labeled with a fluorescein labeled secondary antibody as well as the DNA specific dye toto-3 and visualized using confocal laser scanning microscopy.

In FIG. 4B, to study IgE/antigen induced activation of JAK3 in mast cells, RBL-2H3 mast cells were sensitized with monoclonal anti-DNP IgE and then challenged with DNP-BSA. Mast cells were lysed using a Nonidet-P40 lysis buffer prior to or 30 minutes after antigen challenge, and JAK3 immune complexes from these cell lysates were subjected to anti-phosphotyrosine (APT) Western blot analysis to examine the autophosphorylation of the JAK3 kinase (Lanes 1 and 2). In parallel, JAK3 immune complexes were also examined by anti-JAK3 immunoblotting (Lanes 3 and 4) to confirm that the increased tyrosine phosphorylation in APT blots was not due to differences in the amount of JAK3 immunoprecipitated.

FIGS. 5A–5D show IgE receptor/FcεRI-mediated responses of wild-type and Jak3$^{-/-}$ mast cells. Mast cells were cultured from the bone marrows of JAK3-null (Jak3$^{-/-}$), and wild-type (Jak3$^{+/+}$) control mice. FIGS. 5A1 and 5A2 show flow cytometric comparison of IgE receptor expression on Jak3$^{+/+}$ 5A1 versus Jak3$^{-/-}$ 5A2 mast cells. Mast cell bound IgE was stained with anti IgE-FITC antibody (PharMingen Laboratories). FIG. 5B is a graph showing the proliferative responses of Jak3$^{-/-}$ and Jak3$^{+/+}$ mast cells to SCF determined using the MTT assay system. FIGS. 5C and 5D are graphs showing activity of mast cells. Mast cells from Jak3$^{+/+}$ mice were sensitized with a monoclonal anti-DNP IgE, and then challenged with DNP-BSA, as described in detail in the Examples below. In parallel, Jak3$^{-/-}$ mast cells were also sensitized and challenged with antigen in the same fashion. Histamine (shown in 5C) and leukotriene (LT) C$_4$ (shown in 5D) levels were estimated in cell free supernatants of BMMC. The values (mean ± SEM; n=3) for spontaneous histamine release from Jak3$^{-/-}$ mast cells and control Jak3$^{+/+}$ mast cells were 84.4±12.4 pg/μg protein and 19.5±1.8 pg/μg protein respectively. The IgE/antigen-induced degranulation of bone marrow mast cells was expressed as degranulation index and was calculated using the formula: Degranulation index=Histamine release after antigen challenge/Spontaneous histamine release without antigen challenge. Mast cells from Jak3$^{+/+}$ mice released 41.9±14.2 ng LTC$_4$/10$^6$ cells. The LTC$_4$ release was expressed as percent of control.

FIGS. 6A–6E show the specificty of WHI-P131 of JAK3. In FIGS. 6A–6D, JAK3, JAK1, and JAK2 were immunoprecipitated from Sf21 insect ovary cells transfected with the appropriate baculovirus expression vectors and treated with WHI-P131, then subjected to in vitro kinase assays as described in the Examples below. The enzymatic activity of JAKs was determined by measuring autophosphorylation in a 10 minute kinase assay, as described in the Examples below. The kinase activity (KA) levels were expressed as percentage of baseline activity (%CON). In FIG. 6E, EMSAs of 32Dc22-IL-2Rβ cells are shown. WHI-P131 (100 μg/ml) and WHI-P154 (100 μg/ml) (but not WHI-P132; 100 μg/ml) inhibited IL-2 triggered JAK-3-dependent STAT activation but not IL-3-triggered JAK-1/JAK-2-dependent STAT activation in 32Dc11-IL-2Rβ cells.

FIG. 7 shows the specificity of WHI-P131 for JAK-3. JAK3, SYK, and BTK immunoprecipitated from Sf21 insect ovary cells transfected with the appropriate baculovirus expression vectors, LYN immunoprecipitated from NALM-6 human B-lineage ALL cells, and IRK immunoprecipitated from HepG2 hepatoma cells were treated with WHI-P131, then subjected to in vitro kinase assays, as described in the Examples below.

FIGS. 8A–8D demonstrate that WHI-P131 prevents JAK3 but not SYK Activation in Mast cells after IgE Receptor crosslinking. RBL-2H3 cells were sensitized with monoclonal anti-DNP IgE, treated with either vehicle (8A) or 30 μM WHI-P131 (8B) and then challenged with DNP-BSA. Cells were lysed, and JAK3 immune complexes were subjected to kinase assays in the presence of cold ATP followed by APT immunoblotting (upper panels in 8A & 8B) as well as to JAK3 Western blot analysis (lower panels in 8A & 8B) as described in the Examples below. To show the activation of SYK in mast cells after IgE receptor crosslinking, RBL-2H3 cells were sensitized with monoclonal anti-DNP IgE, left untreated (8C) or treated with either vehicle or 30 μM WHI-P131 (8D) and then challenged with DNP-BSA. Cells were lysed at the indicated time points, and SYK immune complexes were subjected to kinase assays in the presence of cold ATP followed by APT immunoblotting (upper panels in 8C & 8D) as well as to SYK Western blot analysis (lower panels in 8C & 8D). C: Baseline control.

FIG. 9 shows the effect of the JAK3 inhibitor, WHI-P131, on IgE/antigen-induced activation of RBL-2H3 mast cells. RBL-2H3 cells were cultured overnight on 22×22 mm coverslips at a cell density of 0.01×10$^6$/ml with 0.24 mg/ml DNP-IgE. Sensitized RBL-2H3 cells were then treated with 30 μM WHI-P131, vehicle, or control compounds WHI-P258 and WHI-P112 prior to challenge with DNP-BSA, as described in the legend of FIG. 4. After stimulation with DNP-BSA for 1 hour, cells were fixed in cold methanol for 15 minutes followed by permeabilization with PBS containing 0.1% Triton X-100. Cells were incubated with a monoclonal antibody recognizing alpha -tubulin (clone B-5-1-2, Sigma Chemicals, St. Louis, Mo.) for 40 minutes at 37° C.

After washing 3 times with PBS-0.1% Triton X-100, cells were incubated with fluorescein labeled secondary antibody (Zymed, San Francisco, Calif.) for another 40 minutes. Cells were washed three times to remove unbound antibody. DNA labeling was performed by incubation of coverslips with toto-3 (Molecular Probes, Eugene, Oreg.) for 10 minutes. Excessive dye was washed with PBS-0.1% Triton X-100. Cells were visualized under MRC 1024 Laser Scanning Microscope after mounting with Vectashield (Vector laboratories, Inc, Burlingame, Calif.), as previously reported.

FIG. 10 shows the effect of JAK3 inhibitor WHI-P131 on IgE receptor/FcεRI-mediated calcium response in mast cells. IgE sensitized RBL-2H3 cells were loaded with 1 $\mu$M Fluo-3 for 1 hour as described in the Examples below. The cells were then challenged with DNP-BSA or ionomycin and change in fluorescence was recorded. To study the effect of WHI-P131 on intracellular calcium mobilization, IgE-sensitized and Fluo-3 loaded RBL-2H3 cells were incubated with 3 $\mu$M, 12 $\mu$M or 30 $\mu$M WHI-P131 for 5 minutes prior to challenge with DNP-BSA or ionomycin.

FIGS. 11A–11C show the effect of the JAK3 inhibitor WHI-P131 on IgE receptor/FcεRI-mediated mast cell responses. RBL-2H3 cells were sensitized with monoclonal anti-DNP IgE, treated with WHI-P131, vehicle or control compounds, and then challenged with DNP-BSA, as described in detail in the Experimental Procedures section. FIG. 11A is a graph showing mast cell degranulation ($\beta$-hexosaminidase release, % of total), was assessed by measuring the $\beta$-hexosaminidase levels in cell free supernatants and Triton X-100 solubilized pellets using the formula: $\beta$-hexosaminidase release, % of total=100× ($\beta$-hexosaminidase level in supernatant/$\beta$-hexosaminidase level in supernatant+solubilized pellet). Vehicle treated control RBL-2H3 cells released 45.1±3.1% of their hexosaminidase contents after DNP-BSA challenge. FIG. 11B shows $LTC_4$ and FIG. 11C shows TNF-$\alpha$ levels measured in cell-free supernatants. Vehicle treated control cells released 11.3±1.3 pg $LTC_4$, and 160±33.0 pg TNF$\alpha$/$10^6$ mast cells. The results on $LTC_4$ and TNF$\alpha$ release are expressed as percent of maximum control release from vehicle treated control mast cells. The data points represent the mean ± SEM values obtained from 3–6 independent experiments. *$P<0.01$ compared to control as determined by Student's t test. *$P<0.05$ and **$P<0.0001$ compared to control as determined by Student's t test.

Figure 12A:
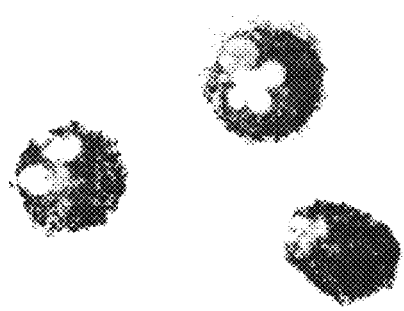
Figure 12B:
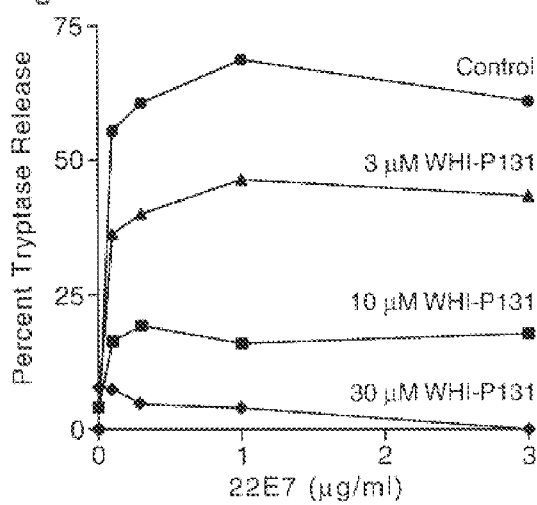
Figure 12C:
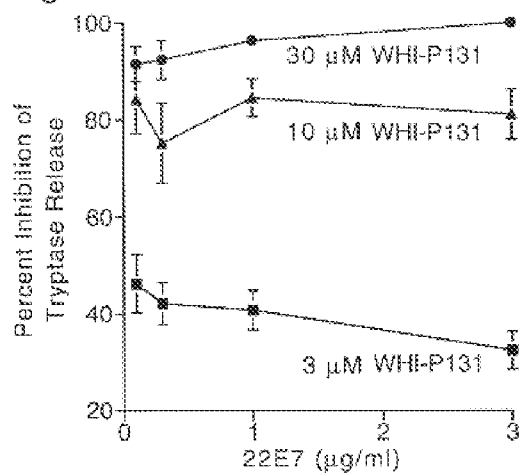
Figure 12D:
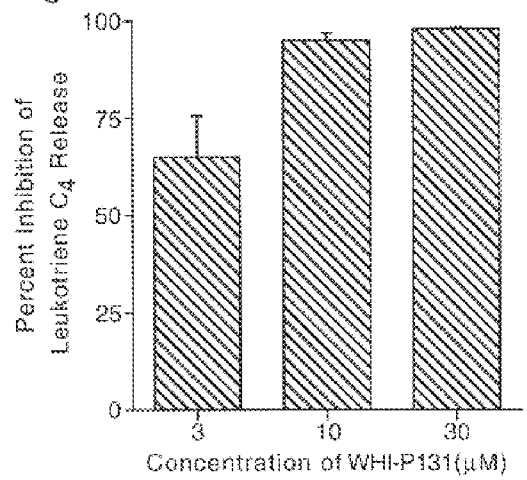

FIGS. 12A–12C show the effect of the JAK3 inhibitor WHI-P131 on IgE receptor/FcεRI-mediated Human Mast Cell Responses. Fetal liver derived human mast cells were cytocentrifuged and fixed with carnoy's fixative.

FIG. 12A is a photomicrograph showing mast cells staining (blue) for tryptase. Fetal liver derived mast cells were stimulated with various concentrations of 22E7 anti-(FcεRI antibody) for 15 minutes in tyrode buffer. In some experiments IgE sensitized mast cells were stimulated by challenging with anti-IgE. To study the effect of WHI-P131, mast cells were incubated with indicated concentrations of WHI-P131 prior to stimulation.

In FIG. 12B, mast cell tryptase release (% of total) was assessed by measuring the tryptase levels in cell free supernatants and solubilized cell pellets by ELISA. The results are expressed as percent tryptase release (B.1; a representative of 3 independent experiments) and percent inhibition of tryptase release (B.2; N=3). The mean spontaneous tryptase released was 8.3±3.9%. In FIG. 12C, $LTC_4$ levels were measured in cell-free supernatants by ELISA (N=6). The results are expressed as percent of control (N=6). Control stimulated cells released was 29.3±14 ng $LTC_4$/$10^6$ cells. The data points represent the mean ± SEM values.

Figure 13A:
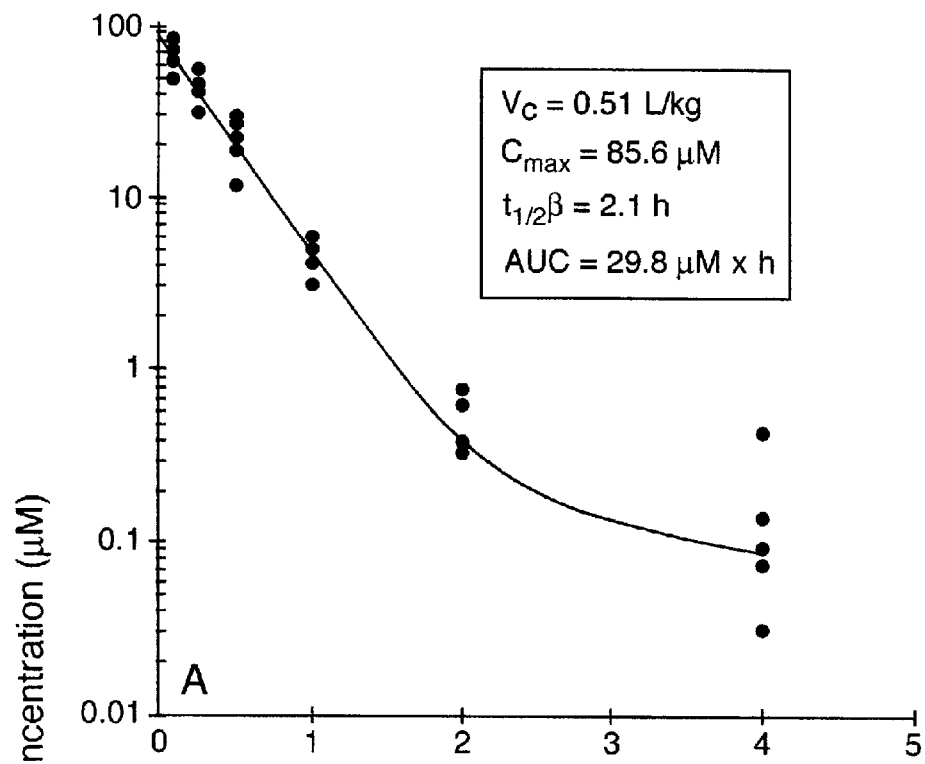
Figure 13B:
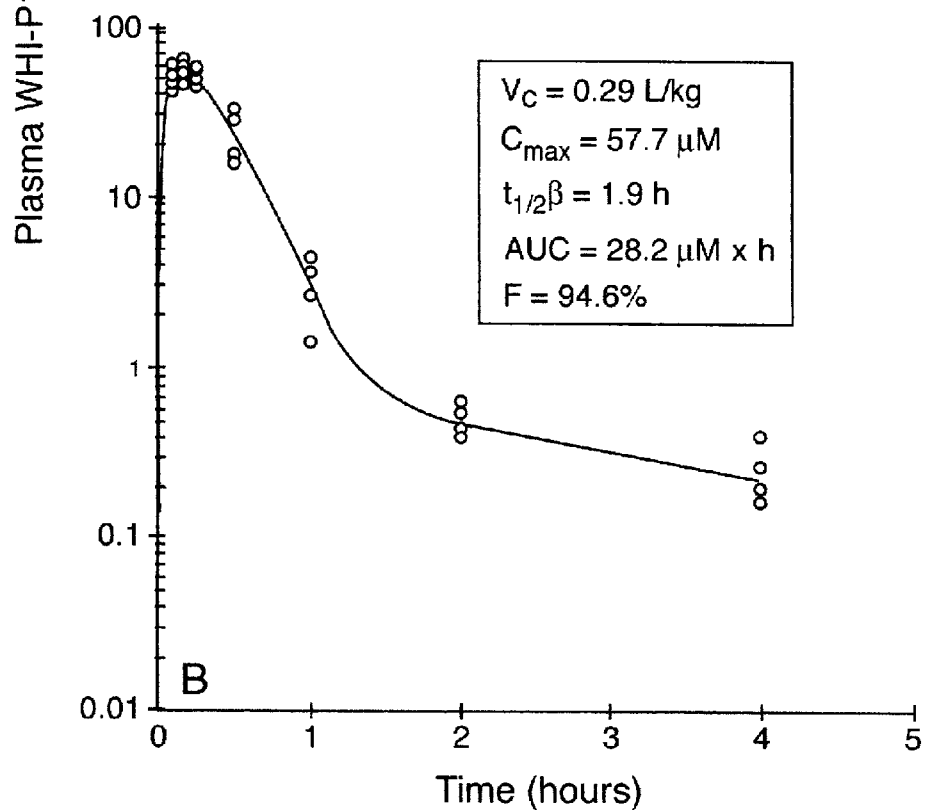

FIGS. 13A and 13B are graphs showing pharmacokinetic features of the JAK3 inhibitor WHI-P131 in mice. Plasma concentration-time profiles of WHI-P131 in mice following intravenous [13A] or intraperitoneal [13B] administration (12.5 mg/kg; 5 mice per group). The pharmacokinetic parameters, including the central volume of distribution (Vc), estimated maximum plasma concentration ($C_{max}$), elimination half-life ($t_{1/2}\beta$), systemic exposure level/area under plasma concentration-time curve (AUC), and bioavailability (F), are shown in the insets.

FIGS. 14A–14E show the effects of the JAK3 inhibitor WHI-P131 on anaphylaxis in mice.

Figure 14A:
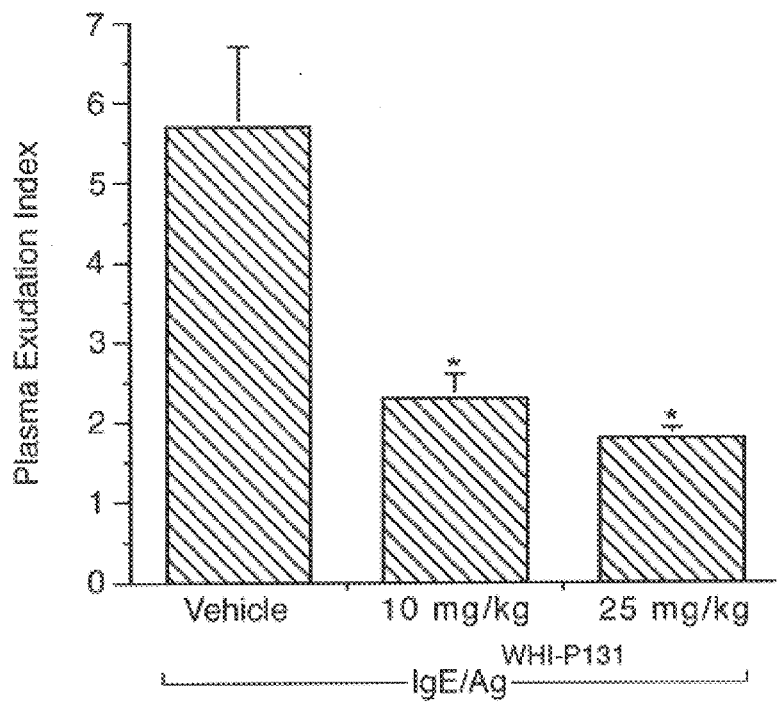

FIG. 14A is a graph showing the effects of WHI-P131 on anaphylaxis-associated vascular hyperpermeability, examined by evaluating the cutaneous extravasation of albumin-bound Evans blue dye in mice (n=12). The plasma exudation indices were determined for vehicle treated as well as WHI-P131 treated mice, as described in the Examples. To study the effect of WHI-P131 on anaphylaxis, IgE sensitized mice were injected with two consecutive doses of 10 or 25 mg/kg WHI-P131 at 90 minutes before and 30 minutes before the antigen challenge, respectively. Mice were then challenged with 100 $\mu$g DNP-BSA in 2% Evans blue dye and the plasma exudation indices were determined. The data points represent the mean ± SEM values. The data are expressed as plasma exudation index (times increase in optical density over PBS treated ears. The mean OD (at 620 nm) of vehicle treated ears was 0.22±0.04 before and 0.918±0.05 after the IgE/antigen challenge. * $p<0.05$ compared to vehicle treated controls.

Figure 14B:
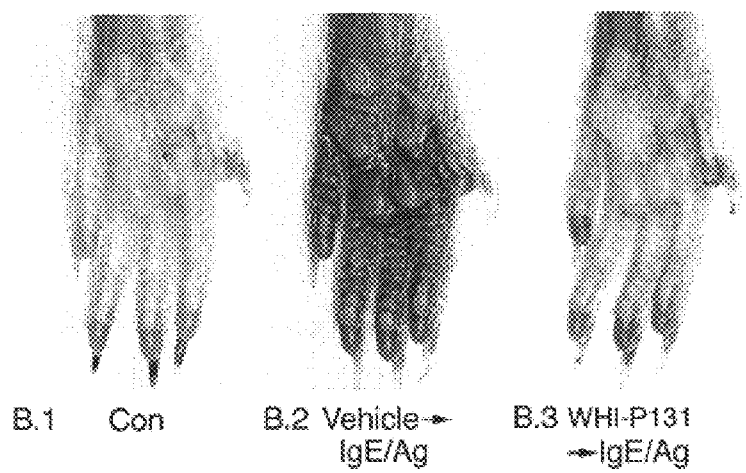

FIG. 14B is a photograph showing plasma extravasation during systemic anaphylaxis, evaluated as described in the Examples. FIG. 14B1 shows a foot pad of a control mouse after intravenous injection of Evans blue dye alone. FIG. 14B2 shows a foot pad of a vehicle treated mouse after coadministration of DNP-BSA and Evans blue. FIG. 14B3 shows a foot pad of a WHI-P131 treated mouse after coadministration of DNP-BSA and Evans blue.

Figure 14C:
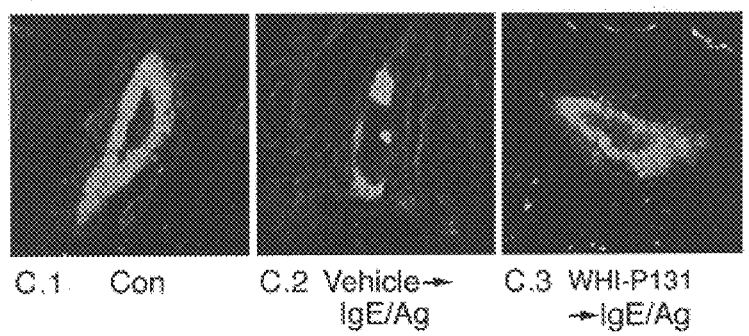

FIG. 14C is a photograph showing results of histopathologic evaluation of mast cell degranulation. Ears were removed 1 hour after the antigen challenge from vehicle treated as well as WHI-P131 treated mice. Formalin-fixed thin sections (3–5 $\mu$m) of ears from were stained with Avidin-FITC.

FIG. 4D is a graph showing blood histamine levels of sensitized mice analyzed after antigen challenge. Blood was collected by retro-orbital bleeding and histamine levels were measured by ELISA. Histamine levels are expressed as nM. The histamine levels in the blood of PBS treated mice and IgE/antigen stimulated mice was 493±131 and 7527±2102 nM respectively. The results are the mean ± SEM values; n=3.

Figure 14D:
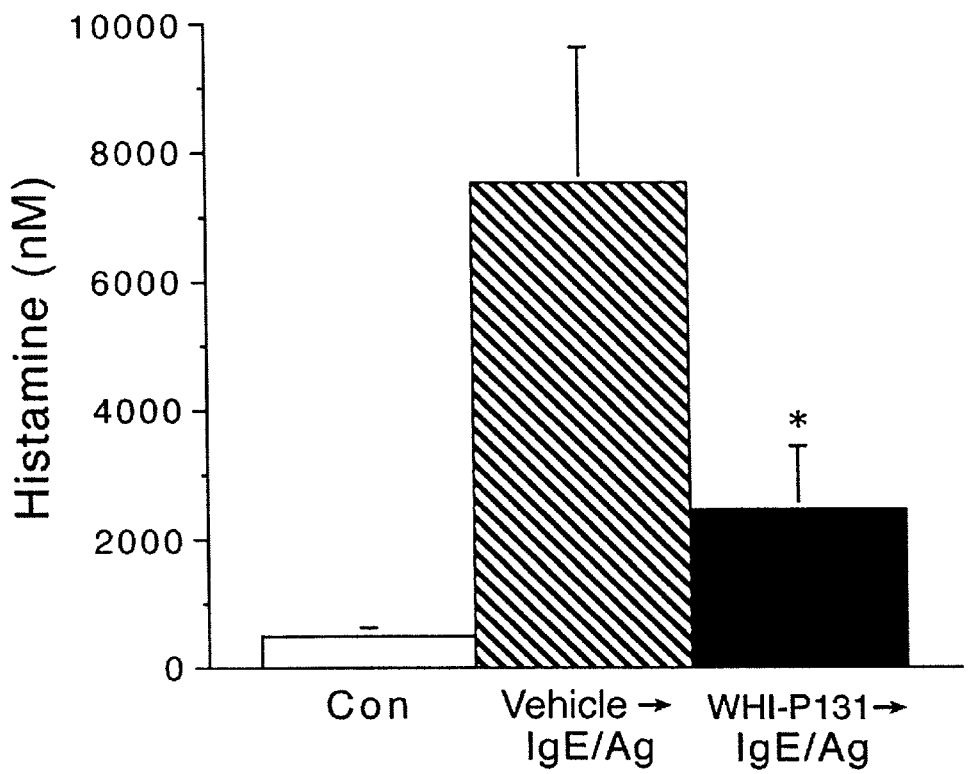
Figure 14E:
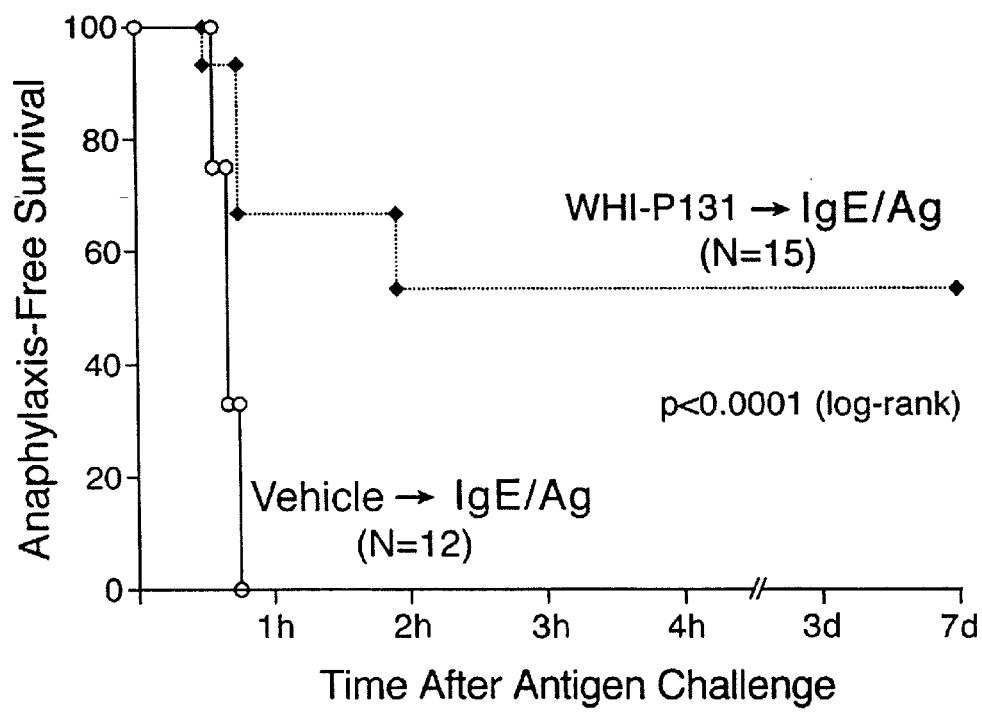

FIG. 14E is a graph showing results of a study of the effect of JAK3 inhibitor WHI-P131 on fatal anaphylaxis in mice. BALB/c mice were sensitized with 100 mg/kg bovine serum albumin in 200 $\mu$l of the adjuvant aluminum hydroxide gel (Reheis Inc., Berkeley, N.J.), which favors the production of IgE in response to the presented antigen. Ten days later, mice were treated with two doses of WHI-P131 (45 mg/kg) or vehicle 30 minutes apart and then challenged with an i.v. injection of the 10 mg/kg BSA. Cumulative proportions of mice surviving anaphylaxis-free are shown according to the time after the antigen challenge. Life-table analysis and statistical comparisons using the log-rank test were performed, as previously reported (Uckun et. al., 1998, *Clin. Cancer Res.*, 4:901–912; Uckun et. al., 1995, *Science*, 267:886–891).

Figure 15:
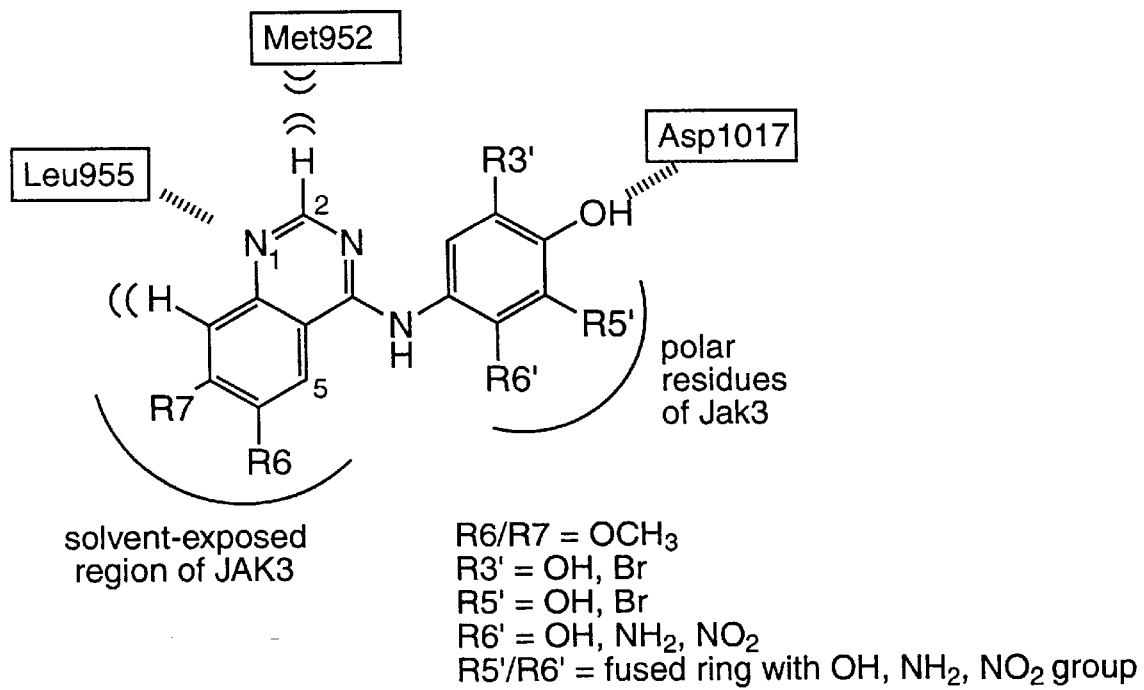

FIG. 15 is a diagram showing features of quinazoline derivatives which aid binding to the JAK3 catalytic site.

DETAILED DESCRIPTION

As used herein, the term "inhibit" means to reduce by a measurable amount, or to prevent entirely.

The term to "treat" comprises inhibiting or blocking at least one symptom that characterizes an immediate hypersensitivity reaction or acute allergic reaction, in a mammal threatened by, or afflicted with, said reaction.

JAK3, a member of the Janus family protein tyrosine kinases, was found to be abundantly expressed in mast cells and its enzymatic activity is enhanced by IgE receptor/FcεRI crosslinking. IgE/antigen induced degranulation and mediator release were substantially reduced with Jak3$^{-/-}$ mast cells from JAK3-null mice that were generated by targeted disruption of Jak3 gene in embryonic stem cells.

JAK3-null mice did not develop an anaphylactic reaction to bovine albumin whereas wild-type mice did. Treatment of mouse, rat, as well as human mast cells with 4-(4'-hydroxylphenyl)-amino-6,7-dimethoxyquinazoline) (Compound 1), a potent and specific inhibitor of JAK3, inhibited degranulation and proinflammatory mediator release after IgE receptor/FcεRI crosslinking. Effective mast cell inhibitory plasma concentrations of Compound 1 were achieved in vivo at non-toxic dose levels.

In vivo administration of this potent JAK3 inhibitor prevented mast cell degranulation and development of cutaneous as well as systemic fatal anaphylaxis in mice.

Thus, JAK3 plays a pivotal role in IgE receptor/FcεRI mediated mast cell responses, both in vitro and in vivo. Therefore, targeting JAK3 with specific inhibitors, such as those of formula I, provide a basis for new and effective treatment as well as prevention programs for mast cell mediated allergic reactions.

Methods of inhibiting JAK-3 can be carried out in vitro. Such in vitro methods are useful for studying the biological processes associated with cell response to allergens and for identifying new therapeutic agents. The methods of the invention can also be carried out in vivo. Such methods are useful for studying the biological processes associated with cell response to allergens, as well as for treating acute pathological conditions in mammals (e.g., humans) that result from exposure to allergens.

Allergic disorders associated with mast cell activation include Type I immediate hypersensitivity reactions such as allergic rhinitis (hay fever), allergic urticaria (hives), angioedema, allergic asthma and anaphylaxis, i.e., "anaphylatic shock." These disorders are treated or prevented by inhibition of JAK-3 activity, for example, by administration of a JAK-3 inhibitor.

According to the invention, the JAK-3 inhibitors may be administered prophylactically, i.e., prior to onset of acute allergic reaction, or the JAK-3 inhibitors may be administered after onset of the reaction, or at both times.

In a preferred embodiment, the JAK-3 inhibitor is targeted to cells that induce an inflamatory resposne, such as mast cells, eosinophils, T cells, and B cells. The compound is targeted by conjugation to a targeting moiety. Useful targeting moieties are ligands which specifically bind mast cell antigens or cell surface ligands, such as CD48 or the SCF receptor. Anti CD48 antibodies or SCF Ligand thus are examples targeting moieties useful in a JAK3 inhibitor conjugate to deliver JAK3 to mast cells.

In addition, the antibodies B43 (binds B cells), TXU (binds T cells), GMSCF (binds receptors on eosinophils) or anti CD13 antibody (binds mast cells) are useful.

Compounds of the Invention:

The JAK-3 inhibitors useful in the methods of the invention include all compounds capable of inhibiting the activity of JAK-3, it being well known in the art how to measure a compound's ability to inhibit JAK-3, for example, using standard tests similar to the test described in the in Examples below.

JAK-3 inhibitors that are useful in the methods of the invention include

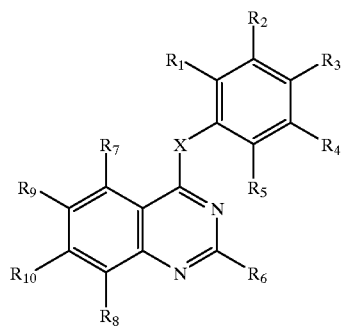

compounds of formula I:
wherein
X is HN, $R_{11}N$, S, O, $CH_2$, or $R_{11}CH$;
$R_{11}$ is hydrogen, $(C_1-C_4)$alkyl, or $(C_1-C_4)$alkanoyl;
$R_1-R_8$ are each independently hydrogen, hydroxy, mercapto, amino, nitro, $(C_1-C_4)$alkyl, $(C_1-C_4)$alkoxy, $(C_1-C_4)$alkylthio, or halo; wherein two adjacent groups of $R_1-R_5$ together with the phenyl ring to which they are attached may optionally form a fused ring, for example, forming a naphthyl or a tetrahydronaphthyl ring; and further wherein the ring formed by the two adjacent groups of $R_1-R_5$ may optionally be substituted by 1, 2, 3, or 4 hydroxy, mercapto, amino, nitro, $(C_1-C_4)$alkyl, $(C_1-C_4)$alkoxy, $(C_1-C_4)$alkylthio, or halo; and provided that at least one of $R_2-R_5$ is OH.

$R_9$ and $R_{10}$ are each independently hydrogen, $(C_1-C_4)$alkyl, $(C_1-C_4)$alkoxy, halo, or $(C_1-C_4)$alkanoyl; or $R_9$ and $R_{10}$ together are methylenedioxy; or a pharmaceutically acceptable salt thereof, and provided that at least one of $R_2-R_5$ is OH.

The following definitions are used, unless otherwise described: halo is fluoro, chloro, bromo, or iodo. Alkyl, alkanoyl, etc., denote both straight and branched groups; but reference to an individual radical such as "propyl" embraces only the straight chain radical, a branched chain isomer such as "isopropyl" being specifically referred to. $(C_1-C_4)$Alkyl includes methyl, ethyl, propyl, isopropyl, butyl, iso-butyl, and sec-butyl; $(C_1-C_4)$alkoxy includes methoxy, ethoxy, propoxy, isopropoxy, butoxy, iso-butoxy, and sec-butoxy; and $(C_1-C_4)$alkanoyl includes acetyl, propanoyl and butanoyl.

A specific group of compounds are compounds of formula I wherein $R_1-R_5$ are each independently hydrogen, mercapto, amino, nitro, $(C_1-C_4)$alkyl, $(C_1-C_4)$alkoxy, $(C_1-C_4)$alkylthio, halogen, or hydroxy, provided one of $R_2-R_5$ is OH.

Another specific group of compounds are compounds of formula I wherein $R_9$ and $R_{10}$ are each independently hydrogen, $(C_1-C_4)$alkyl, halo, or $(C_1-C_4)$alkanoyl; or $R_9$ and $R_{10}$ together are methylenedioxy; or a pharmaceutically acceptable salt thereof.

Preferred JAK-3 inhibitors include 4-(4'-hydroxylphenyl)-amino-6,7-dimethoxyquinazoline (P131), 4-(3'-bromo-4'-hydroxylphenyl)-amino-6,7-dimethoxyquinazoline (P154), 4-(3'-hydroxyphenyl)-amino-6,7-dimethoxyquinazoline, (P180) and 4-(3',5'-dibromo-4'-hydroxy phenyl)-6,7-dimethoxyquinazoline (P97) or a pharmaceutically acceptable salt thereof.

Second generation of JAK3 inhibitors:

Using the model methods modeling JAK-3 binding described hereinbelow, one skilled in the art can prepare a number of prefered JAK-3 inhibitors that fit the JAK-3 binding pocket are thereby predicted to have potent inhibitory activity.

Compounds are designed to fit and fill the binding pocket and to provide areas for interaction with contact residues as shown in FIG. 15. Second generation compounds of the invention, which were designed to fit and target the JAK-3 kinase active site, are predicted to interact favorably with JAK-3 kinase residues. These compounds of the invention are shown diagramatically below and particularly in Table 2. The synthetic schemes for producing these compounds are depicted below in schemes 3A–3D.

TABLE 2

Second generation quinazoline designs targeting JAK3 kinase active site. All compounds were predicted to interact favorably with JAK3 kinase residues. NA = not applicable.

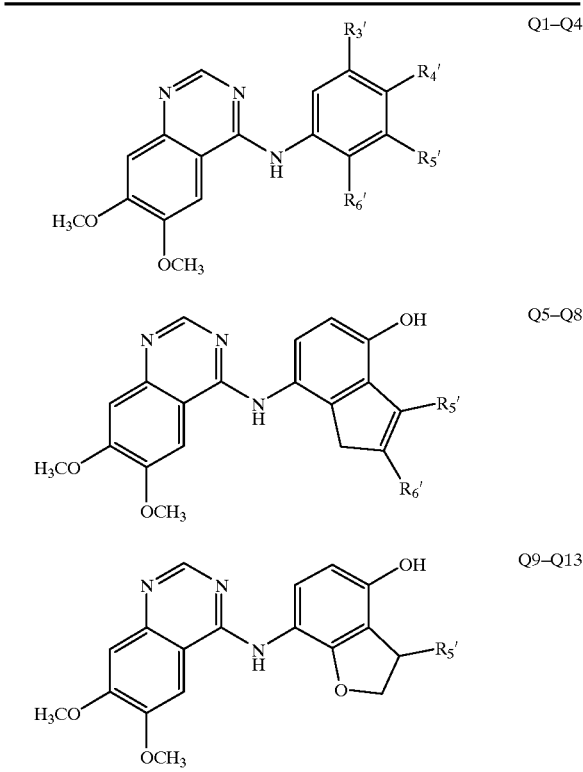

TABLE 2-continued

Second generation quinazoline designs targeting JAK3 kinase active site. All compounds were predicted to interact favorably with JAK3 kinase residues. NA = not applicable.

| Compound Name | R3' | R4' | R5' | R6' | R7' | Molecular Surface Area (Å$^2$) | Molecular Volume (Å$^3$) |
|---|---|---|---|---|---|---|---|
| Q1 | H | OH | OH | H | NA | 275 | 273 |
| Q2 | Br | H | OH | CH$_2$OH | NA | 300 | 288 |
| Q3 | Br | H | OH | NH$_2$ | NA | 283 | 274 |
| Q4 | Br | H | OH | NO$_2$ | NA | 300 | 294 |
| Q5 | H | OH | Br | OH | NA | 322 | 308 |
| Q6 | H | OH | Br | CH$_2$OH | NA | 327 | 323 |
| Q7 | H | OH | Hr | NH$_2$ | NA | 318 | 311 |
| Q8 | H | OH | Br | NO$_2$ | NA | 340 | 329 |
| Q9 | H | OH | Br | H | NA | 317 | 295 |
| Q10 | H | OH | OH | H | NA | 308 | 306 |
| Q11 | H | OH | CH$_2$OH | H | NA | 314 | 321 |
| Q12 | H | OH | NH$_2$ | H | NA | 309 | 309 |
| Q13 | H | OH | NO$_2$ | H | NA | 329 | 331 |
| Q14 | H | OH | Br | H | OH | 336 | 317 |
| Q15 | H | OH | Br | H | CH$_2$OH | 349 | 334 |
| Q16 | H | OH | Br | H | NH$_2$ | 336 | 321 |
| Q17 | H | OH | Br | H | NO$_2$ | 359 | 340 |

Scheme 3A
Synthesis of quinazoline derivaties Q1–Q4

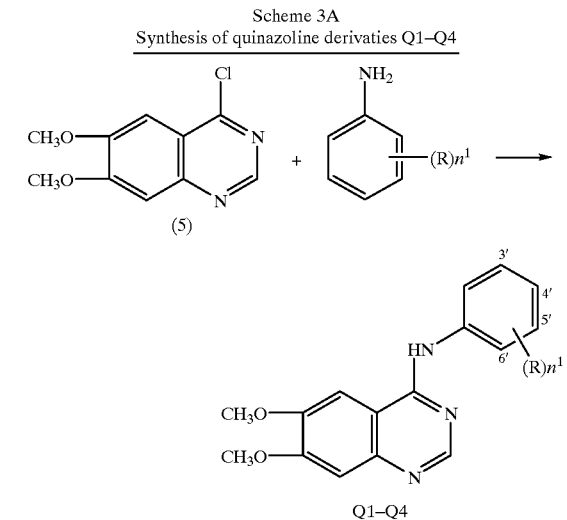

Preferred substitutions are those where:

R3'=H, Br, OH
R4'=H, OH, H, Br
R5'=OH
R6'=H, CH$_2$OH, NH$_2$, NO$_2$
$n^1$=1–3, provided one of $R_3$, $R_4$, $R_5$ is OH. Preferably, there are 1–3 substitutions on the phenyl ring.

Scheme 3B
Synthesis of quinazoline derivatives Q5–Q8

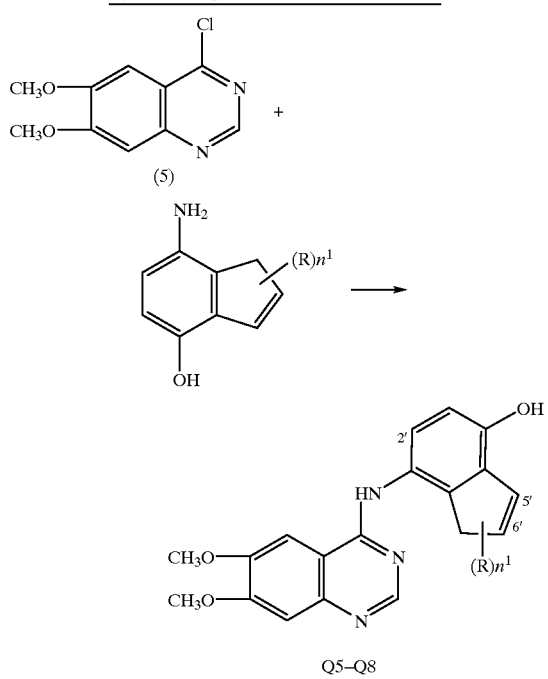

Preferred are:

R5'=Br

R6'=OH, CH$_2$OH, NH$_2$, NO$_2$ n$^1$=1–3

Scheme 3C
Synthesis of quinazoline derivatives Q9–Q13

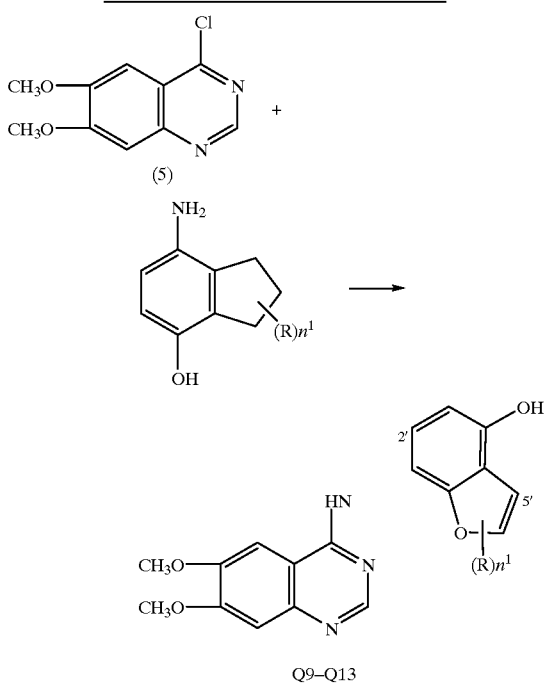

Preferably, R5'=Br, OH, CH$_2$OH, NH$_2$, or NO$_2$.

Scheme 3D.
Synthesis of quinazoline derivatives Q14–Q17.

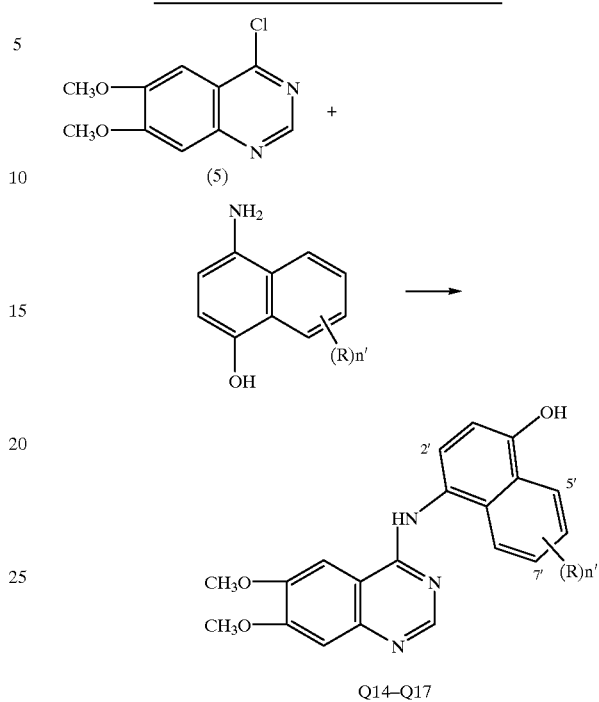

Preferably:

R5'=Br

R7'=OH, CH$_2$OH, NH$_2$, or NO$_2$ n$^1$=1–3

Suitable JAK-3 inhibitors also include antibodies to JAK-3, and antisense oligonucleotides that inhibit JAK-3 expression and synthesis.

Compounds that inhibit JAK-3 can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, JAK-3 inhibitors may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the JAK-3 inhibitors may be combined with one or more excipients and used in the form of ingestible tablets, buccal tablets, troches, capsules, elixirs, suspensions, syrups, wafers, and the like. The JAK-3 inhibitors may be combined with a fine inert powdered carrier and inhaled by the subject or insufflated. Such compositions and preparations should contain at least 0.1% JAK-3 inhibitor. The percentage of the compositions and preparations may, of course, be varied and may conveniently be between about 2 to about 60% of the weight of a given unit dosage form. The amount of JAK-3 inhibitor in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the JAK-3 inhibitor may be incorporated into sustained-release preparations and devices.

The JAK-3 inhibitor may also be administered intravenously or intraperitoneally by infusion or injection. Solutions of the JAK-3 inhibitor can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the JAK-3 inhibitor which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the JAK-3 inhibitor in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the JAK-3 inhibitor may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water-alcohol/glycol blends, in which the JAK-3 inhibitor can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the JAK-3 inhibitors to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the JAK-3 inhibitor in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the JAK-3 inhibitor required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The JAK-3 inhibitor is conveniently administered in unit dosage form; for example, containing 5 to 1000 mg, conveniently 10 to 750 mg, most conveniently, 50 to 500 mg of active ingredient per unit dosage form.

Ideally, the JAK-3 inhibitor should be administered to achieve peak plasma concentrations of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the JAK-3 inhibitor, optionally in saline, or orally administered as a bolus containing about 1–100 mg of the JAK-3 inhibitor. Desirable blood levels may be maintained by continuous infusion to provide about 0.01–5.0 mg/kg/hr or by intermittent infusions containing about 0.4–15 mg/kg of the JAK-3 inhibitor.

The JAK-3 inhibitor may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Example 1

Construction of a Homology Model for the JAK-3 Kinase Domain

Because the three dimensional coordinates of the JAK3 kinase domain are currently unknown, a structural model of JAK3 was required for a docking analysis of JAK3 inhibitors. A homology model of JAK3 was constructed by using known coordinates of homologous kinase domains as a reference.

The design of the JAK3 homology model was carried out by first obtaining the protein sequence of JAK3 (Swiss-Prot #P52333, Univ. of Geneva, Geneva, Switzerland) from GenBank (National Center for Biotechnology Information, Bethesda, Md.) and determining the most reasonable sequence alignment for the JAK3 kinase domain relative to some template coordinates [known kinase structures, HCK (Sicheri et. al., 1997, Nature 385, 602–609), FGFR (Mohammadi et. al., 1996; Mohammadi et. al., 1997), and IRK (Hubbard, 1997, EMBO J. 16, 5572–5581)]. This was accomplished by first superimposing the Cα coordinates of the kinase domains of HCK, FGFR, and IRK using the InsightII program (Molecular Simulation Inc. 1996, San Diego, Calif.) to provide the best overall structural comparison. The sequences were then aligned based on the superimposition of their structures (amino acid sequences were aligned together if their Cα positions were spatially related to each other). The alignment accommodated such features as loops in a protein which differed from the other protein sequences. The structural superimposition was performed using the Homology module of the InsightII program and a Silicon Graphics INDIGO2 computer (Silicon Graphics, Mountain View, Calif.).

The sequence alignment was done manually and produced a sequence variation profile for each superimposed Cα position. The sequence variation profile served as a basis for the subsequent sequence alignment of the JAK3 kinase with the other three proteins. In this procedure, the sequence of JAK3 was incorporated into the program and aligned with the three known kinase proteins based on the sequence variation profiles described previously.

Next, a set of 3D coordinates was assigned to the JAK3 kinase sequence using the 3D coordinates of HCK as a template and the Homology module within the InsightII program. The coordinates for a loop region where a sequence insertion occurs (relative to HCK without the loop) were chosen from a limited number of possibilities automatically generated by the computer program and manually adjusted to a more ideal geometry using the program CHAIN (Sack, 1988).

Finally, the constructed model of the JAK3 kinase domain was subjected to energy minimization using the X-PLOR program (Brunger, 1992) so that any steric strain introduced during the model-building process could be relieved. The model was screened for unfavorable steric contacts and if necessary such side chains were remodeled either by using a rotamer library database or by manually rotating the respective side chains. The procedure for homology model construction was repeated for JAK1 (SWISS-PROT #P23458) and JAK2 (Genbank #AF005216) using the JAK3 model as a structural template. The energy minimized homology models of JAK1, JAK2, and JAK3 were then used, in conjunction with energy-minimized structural models of dimethoxyquinazoline compounds, for modeling studies of JAK/dimethoxyquinazoline complexes.

Figure 1A:
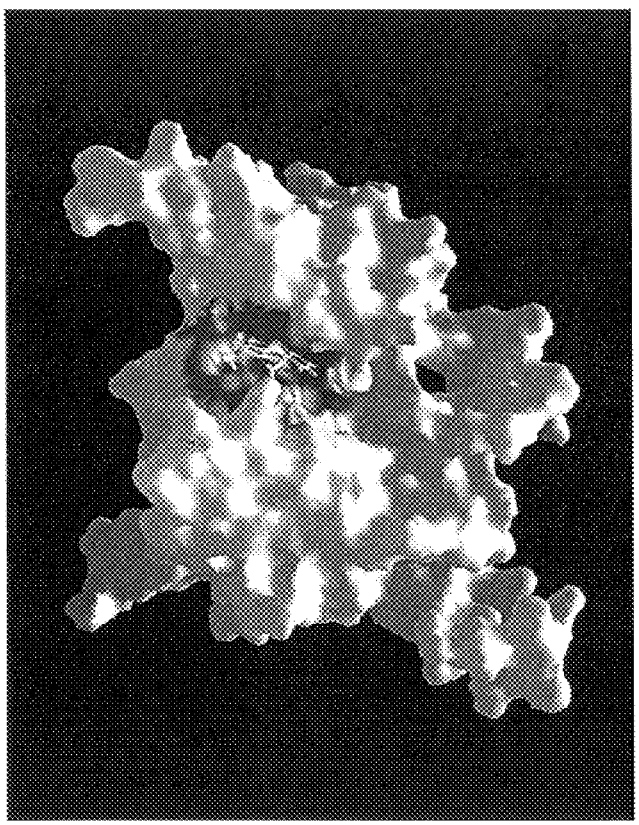
FIGS. 1A–1C.
Figure 1B:
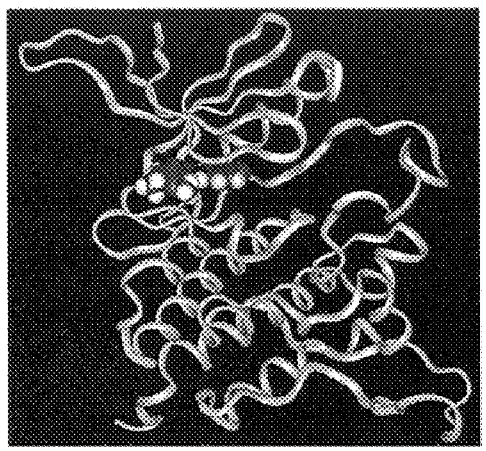

FIGS. 1A & 1B show the JAK3 homology model of the kinase domain, which is composed of an N-terminal lobe and a C-terminal lobe that are linked by a hinge region near the catalytic (ATP-binding) site. The catalytic site is a pocket located in the central region of the kinase domain, which is defined by two β-sheets at the interface between the N and C lobes. The opening to the catalytic site is solvent accessible and facilitates binding of ATP. Small molecule inhibitors could also bind to the catalytic site which would result in an attenuation of PTK activity by inhibiting the ATP binding.

Figure 1C:
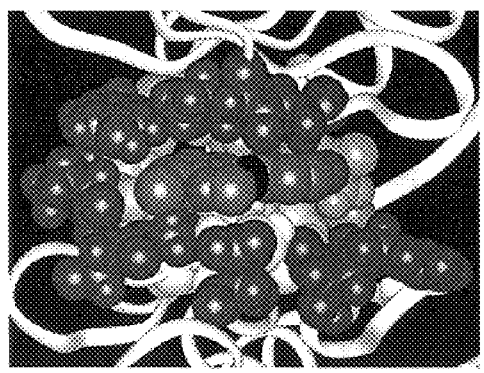

An analysis of the JAK3 model revealed specific features of the catalytic site which can be described as a quadrilateral-shaped pocket (FIG. 1C). The opening of the pocket is defined by residues Pro906, Ser907, Gly908, Asp912, Arg953, Gly829, Leu828, and Tyr904 (blue residues in FIG. 1C). The far wall deep inside the pocket is lined with Leu905 (backbone portion), Glu903, Met902, Lys905, and Asp967 (pink residues, FIG. 1C). The floor of the pocket is lined by Leu905 (side chain portion), Val884, Leu956, and Ala966 (yellow residues, FIG. 1C). The residues defining the roof of the pocket include Leu828, Gly829, Lys830, and Gly831 (uppermost blue residues, FIG. 1C). FIGS. 1C and 2A illustrate that the catalytic site of the JAK3 model has approximate dimensions of 8 Å×11 Å×20 Å and an available volume for binding of approximately 533 Å$^3$. According to the model, the solvent exposed opening to the binding region would allow inhibitors to enter and bind if the molecule contains some planarity. Asp 1017 can form a hydrogen bond with a 3' or 4' OH group of a quinazoline bound to the catalytic site, and Leu955 can interact with a quinazoline ring nitrogen hydrophilic substituent at C5' and C6' on the phenyl ring of quinazoline would also enhance binding to JAK3. Steric hinderence with Met 952 prevents the addition of a non-hydrogen substituent at C2. Modifications to increase the volume of the inhibitor in the pocket, for example to a volume of about 200 Å$^3$–500 Å$^3$, 225–350 Å$^3$ will provide more potent compounds.

While most of the catalytic site residues of the JAK3 kinase domain were conserved relative to other PTK, a few specific variations were observed (FIG. 3). These differences include an alanine residue in BTK, IRK, and HCK/LYN (region A, FIG. 3A) which changes to Glu in SYK and Pro906 in JAK3. At region B, a tyrosine residue is conserved in JAK3 (Tyr904), BTK, and LYN, but changes to Phe in HCK (which is the only apparent residue difference between HCK and LYN which is relevant to inhibitor binding), Met in SYK, and Leu in IRK. Region C shows a methionine residue which is conserved in BTK. IRK, and HCK/LYN, but changes to Leu905 in JAK3 and to Ala in SYK. Region D shows Met902 in JAK3, which is conserved in SYK and IRK but changes to Thr in BTK and to a much smaller residue, Ala, in LYN and HCK. This Met902 residue in JAK3, which is located on the back wall of the pocket and protrudes in toward the center of the pocket volume, can significantly affect the shape of the binding pocket. At this location, the extended conformation of the Met902 side chain can hinder the close contact of inhibitors with residues lining the back wall of the pocket and the hinge region, relative to other kinases with smaller residues here such as BTK (Thr) and HCK/LYN (Ala).

Ala966 in region E is conserved in HCK/LYN but changes to Gly in IRK and to the more hydrophilic residue Ser in BTK and SYK. Region F, which is farther away from the inhibitor location, is the least conserved region of the catalytic site and contains Asp912 in JAK3, Asn in BTK, Lys in SYK, Ser in IRK, and Asp in HCK/LYN (FIG. 3). These residue identity differences among tyrosine kinases provide the basis for designing selective inhibitors of the JAK3 kinase domain.

JAK3 contains Ala 1016 in the binding site, which changes to glycine in JAK1 and JAK2. The slightly larger alanine residue of JAK3 can provide larger alanine residue of JAK3 can provide larger surface contact and hydrophobic interactions with inhibitors.

Example 2

Docking Procedure using Homology Model of JAK3 Kinase Domain

Modeling of the JAK3/dimethoxyquinazoline complexes was done using the Docking module within the program INSIGHTII and using the Affinity suite of programs for automatically docking an inhibitor into a kinase domain binding site. An energy-minimized model for each inhibitor compound was docked into the homology model coordinates of the catalytic site of JAK3. Each compound was docked into the active site of the JAK3 kinase domain based on the position of quercetin in the HCK/quercetin crystal structure (Sicheri et al., 1997, *Nature,* 385:602–609).

The hydrogens on JAK3 were generated and potentials were assigned to JAK3 and its inhibitor model prior to the start of the docking procedure. The docking method in the InsightII program uses the CVFF force field and a Monte Carlo search strategy to search for and evaluate docked structures. While the coordinates for the bulk of the receptor were kept fixed, coordinates of a defined region of the binding site were allowed to adjust as simulated interactions with the inhibitor were estimated. This binding region was defined as a zone 4.5 Å away from the inhibitor and allowed residues within this zone to shift and/or rotate to energetically favorable positions to accommodate the inhibitor.

After an assembly was defined which included the protein and its inhibitor molecule, docking calculations were performed using the fixed docking mode. Calculations which approximated hydrophobic and hydrogen bonding interactions were used to identify the five best docked positions for each compound in the JAK3 catalytic site. The various docked positions of each compound were evaluated using a Ludi (Bohm, 1994) scoring procedure in INSIGHTII which estimates a binding constant, $K_i$, taking into account lipophilic, hydrogen bonding, and van der Waals interactions between the inhibitor and the protein. A comparison of the catalytic site residues of several different PTK was made by manually superimposing crystal structure coordinates of the kinase domains of HCK, and IRK (Hubbard, 1997, EMBOJ. 16:5572–81) and models of JAK1, JAK2, JAK3, BTK (Mahajan, et. al., 1999, Mol. Cell. Biol. 15, 5304–5311), and SYK (Mao, unpublished data), and then identifying features in the active site which were unique to JAK3 (FIG. 3).

The computer docking procedure was used to predict how well potential inhibitors could fit into and bind to the catalytic site of JAK3 and result in kinase inhibition (FIG. 2B). The dimethoxyquinazoline compound WHI-P258 (4-(phenyl)-amino-6,7-dimethoxyquinazoline) contains two methoxy groups on the quinazoline moiety but no other ring substituents. Molecular modeling studies using the homology model of JAK3 kinase domain suggested that WHI-P258 would fit into the catalytic site of JAK3, but probably would not bind very tightly due to limited hydrogen bonding interactions. Asp967, a key residue in the catalytic site of JAK3, can form a hydrogen bond with molecules binding to the catalytic site, if such molecules contain a hydrogen bond donor group such as an OH group. WHI-P258, however, does not contain an OH group and therefore would not interact as favorably with Asp967. We postulated that the presence of an OH group at the 4' position of the phenyl ring of WHI-P258 would result in stronger binding to JAK3 because of added interactions with Asp967. A series of dimethoxyquinazoline compounds were designed and synthesized to test this hypothesis.

An estimation of the molecular volume for the compounds is provided in Table 1. A summary of structural features of the designed dimethoxyquinazoline compounds which were observed to be relevant for binding to the catalytic site of JAK3 is shown in FIG. 2C. The approximate molecular volumes of the compounds in Table 1 range from 252 $Å^3$ to 307 $Å^3$, which are small enough to fit into the 530 $Å^3$ binding site of JAK3 kinase. Table 1 also lists the results of molecular modeling studies including estimated binding constants (i.e., $K_i$ values) for the compounds which were docked into the JAK3 catalytic site. The compounds which were evaluated in docking studies contain substitutions of similar functional groups at different positions on the phenyl ring.

TABLE 1

Predicted interaction of quinazolines with JAK3 kinase active site and measured inhibition values ($IC_{50}$ values) for JAK3 kinase.

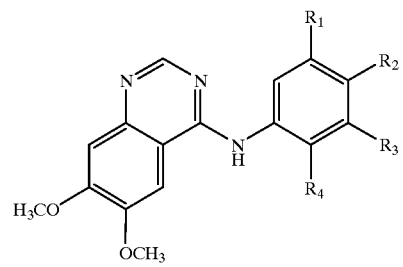

| Compound Name | $R_1$ | $R_2$ | $R_3$ | $R_4$ | Predicted binding to JAK3 | Molecular Surface Area ($Å^2$) | Molecular Volume ($Å^3$) | $IC_{50}$ ($\mu M$) |
|---|---|---|---|---|---|---|---|---|
| WHI-P131 | H | OH | H | H | favorable | 726 | 261 | 78 |
| WHI-P154 | H | OH | Br | H | favorable | 296 | 284 | 128 |
| WHI-P180 | H | H | OH | H | favorable | 273 | 260 | 3 |
| WHI-P97 | Br | OH | Br | H | favorable | 314 | 307 | 11 |

TABLE 1-continued

Predicted interaction of quinazolines with JAK3 kinase active site and measured inhibition values ($IC_{50}$ values) for JAK3 kinase.

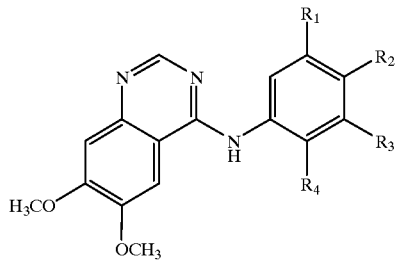

| Compound Name | $R_1$ | $R_2$ | $R_3$ | $R_4$ | Predicted binding to JAK3 | Molecular Surface Area (Å²) | Molecular Volume (Å³) | $IC_{50}$ (μM) |
|---|---|---|---|---|---|---|---|---|
| WHI-P79 | H | H | Br | H | less favorable | 278 | 272 | >300 |
| WHI-P111 | H | $CH_3$ | Br | H | less favorable | 309 | 291 | >300 |
| WHI-P112 | Br | H | H | Br | less favorable | 306 | 297 | >200 |
| WHI-P132 | H | H | H | OH | less favorable | 269 | 262 264 | >300 |
| WHI-P258 | H | H | H | H | less favorable | 266 | 252 | >300 |

The conformations of the energy-minimized models of the compounds listed in Table 1 were relatively planar, with dihedral angles of approximately 4–18° between the phenyl ring and quinazoline ring system. This conformation allows the compounds to fit more easily into the catalytic site of JAK3. All of the listed compounds contain a ring nitrogen (N1), which can form a hydrogen bond with NH of Leu905 in the hinge region of JAK3. When N1 is protonated, the NH can instead interact with the carbonyl group in Leu905 of JAK3. The presence of an OH group at the 4' position on the phenyl ring was anticipated to be particularly important for binding to the catalytic site of JAK3. WHI-P131 (estimated $K_i$=2.3 μM), WHI-P154 (estimated $K_i$=1.4 μM), WHI-P97 (estimated $K_i$=0.6 μM) shown in Table 1 were predicted to have favorable binding to JAK3 and potent JAK3 inhibitory activity because they contain a 4' OH group on the phenyl ring which can form a hydrogen bond with Asp967 of JAK3, contributing to enhanced binding. By comparison, the 2' OH group of WHI-P132 is not in the right orientation to interact with Asp967 and it probably would form an intramolecular hydrogen bond with the quinazoline ring nitrogen, which may contribute to a significantly lower affinity of WHI-P132 for the catalytic site of JAK3.

The relatively large bromine substituents (WHI-P97, WHI-P154) can increase the molecular surface area in contact with binding site residues if the molecule can fit into the binding site. Modeling of WHI-P154 and WHI-P97 showed that there is enough room to accommodate the bromine groups if the phenyl ring is tilted slightly relative to the fused ring group of the molecule.

Example 3

Chemical synthesis and Characterization of JAK-3 Inhibitors

The results from the modeling studies prompted the hypothesis that WHI-P131, WHI-P154, and WHI-P97 would exhibit potent JAK3-inhibitory activity. In order to test this hypothesis and validate the predictive value of the described JAK3 homology model, we synthesized WHI-P131, WHI-P154, WHI-P97, and 5 other dimethoxyquinazoline compounds listed in Table 1.

Chemical synthesis of quinazoline derivatives. The common starting material, 4-chloro-6,7-dimethoxyquinazoline (1) for the synthesis of all the WHI compounds, was prepared using published procedures as shown in Scheme 1.

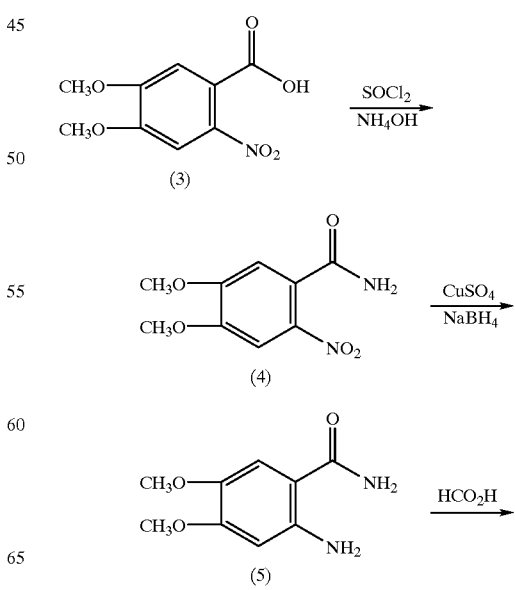

-continued

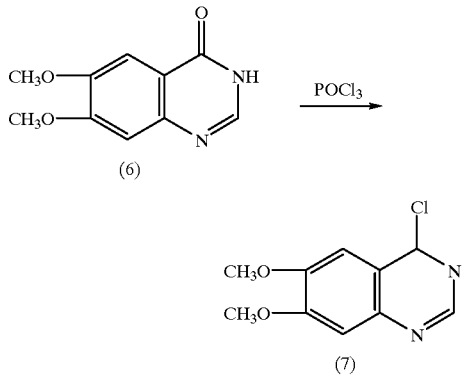

4,5-Dimethoxy-2-nitrobenzoic acid (3) was treated with thionyl chloride and then reacted with ammonia to give 4,5-dimethoxy-2-nitrobenzamide (4) as described by F. Nomoto et al. *Chem. Pharm. Bull.,* 1990, 38, 1591–1595. The nitro group in compound (4) was reduced with sodium borohydride in the presence of copper sulfate (see C. L. Thomas, *Catalytic Processes and Proven Catalysts,* Academic Press, New York (1970)) to give 4.5-dimethoxy-2-aminobenzamide (5) which was cyclized by refluxing with formic acid to give 6,7-dimethoxyquinazoline-4(3H)-one (6). Compound (6) was refluxed with phosphorus oxytrichloride to provide the common synthetic precursor (7).

The compounds listed in Table 1 were all synthesized from 4-chloro-6,7-dimethoxyquinazoline 1 according to Scheme 2, as previously reported (Narla et. al., 1998). In this procedure, a mixture of 4-chloro-6,7-dimethoxyquinazoline 1 (448 mg, 2 mmols) and the substituted aniline (2.5 mmols) in EtOH (20 mL) was heated to reflux. Heating was continued for 4–24 hours. After cooling to room temperature, excess amount of Et₃N was added to neutralize the solution and the solvent was concentrated to give the crude product, which was recrystallized from DMF.

Scheme 2
Synthesis of JAK3 inhibitors

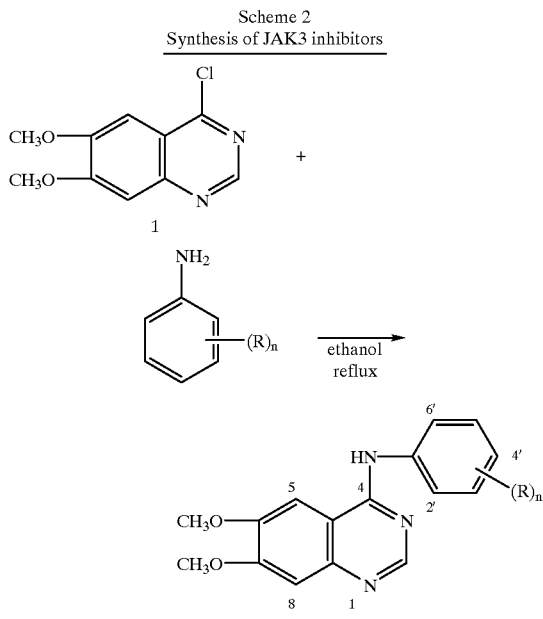

WHI-P79: R = 3'-Br.
WHI-P97: R = 3'-Br, 4'-OH, 5'-Br.
WHI-P111: R = 3'-Br, 4'-CH₃.
WHI-P112: R = 2'-Br; 5'-Br.
WHI-P131: R = 4'-OH.
WHI-P132: R = 2'-OH.
WHI-P154: R = 3'-Br, 4'-OH.
WHI-P258: R = H
WHI-P180: R = 5'OH

Analytical data for synthesized compounds:

Melting points are uncorrected. ¹H NMR spectra were recorded using a Varian Mercury 300 spectrometer in DMSO-d₆ or CDCl₃. Chemical shifts are reported in parts per million (ppm) with tetramethylsilane (TMS) as an internal standard at zero ppm. Coupling constants (J) are given in hertz and the abbreviations s, d, t, q, and m refer to singlet, doublet, triplet quartet and multiplet, respectively. Infrared spectra were recorded on a Nicolet PROTEGE 460-IR spectrometer. Mass spectroscopy data were recorded on a FINNIGAN MAT 95, VG 7070E-HF G. C. system with an HP 5973 Mass Selection Detector. UV spectra were recorded on BECKMAN DU 7400 and using MeOH as the solvent. TLC was performed on a precoated silica gel plate (Silica Gel KGF; Whitman Inc). Silica gel (200–400 mesh, Whitman Inc.) was used for all column chromatography separations. All chemicals were reagent grade and were purchased from Aldrich Chemical Company (Milwaukee, Wis.) or Sigma Chemical Company (St. Louis, Mo.).

4-Chloro-6,7-dimethoxyquinazoline 1: Yield 75.00%; mp 259.0–263.0° C.; ¹H NMR (DMSO-d₆) d 8.75 (s, 1H, 2-H), 7.53 (s, 1H, 5-H), 7.25 (s, 1H, 8H), 3.91 (s, 3H, —OCH₃), 3.89 (s, 3H, —OCH₃); IR (KBr) 2963, 2834, 1880, 1612, 1555, 1503, 1339, 1153, 962 cm⁻¹; GC/MS m/z 224 (M⁺, 100), 209 (M⁺—CH₃, 9), 189 (19), 169 (11); Anal. (C₁₀H₉ClN₂O₂) C, H, N.

4,5-Dimethoxy-2-nitrobenzamide 3: Yield 88.50%; mp 197.0–200.0° C.; ¹H NMR(DMSO-d₆) d 7.60 (s, 2H, —NH₂), 7.57 (s, 1H, 6-H), 7.12 (s, 1H, 3-H), 3.90 (s, 3H, —OCH₃), 3.87 (s, 3H, —OCH₃); IR (KBr) 3454,2840, 1670, 1512, 1274, 1227 cm⁻¹; GC/MS m/z 226 (M⁺, 10), 178(99), 163(100), 135(51).

6,7-Dimethoxyquinazoline-4(3H)-one 5: Yield 81.50%; mp 295.0–297.0° C.; ¹H NMR (DMSO-d₆) d 12.03 (br, s, 1H, —NH), 7.99 (s, 1H, 2-H), 7.42 (s, 1H , 5-H), 7.11 (s, 1H , 8-H), 3.88 (s, 3H, —OCH₃), 3.85 (s, 3H, —OCH₃); IR (KBr) 3015, 2840, 1648, 1504, 1261, 1070 cm⁻¹; GC/MS m/z 206 (M⁺, 100), 191 (M⁺—CH₃, 31), 163 (17), 120 (15).

4-(3'-Bromophenyl)-amino-6,7-dimethoxyquinazoline WHI-P79: Yield 84.17%; mp 246.0–249.0° C.; ¹H NMR (DMSO-d₆) d 10.42 (br, s, 1H, NH), 8.68 (s, 1H , 2-H), 8.07–7.36 (m, 5H, 5, 2', 4', 5', 6'-H), 7.24 (s, 1H, 8-H), 3.98 (s, 3H, —OCH₃), 3.73 (s, 3H, —OCH₃); IR (KBr) 3409, 28836, 1632, 1512, 1443, 1243, 1068 cm⁻¹; GC/MS m/z 361 (M⁺+1.62),360 (M⁺, 100), 359 (M⁺−1, 64), 344(11), 222(11), 140(14); Anal. (C₁₆H₁₄BrN₃O₂) C, H, N.

4-(3',5'-Dibromo-4'-hydroxylphenyl)-amino-6,7-dimethoxyquinazoline WHI-P97: Yield 72.80%; mp>300.0° C.; ¹H NMR (DMSO-d₆) d 9.71 (s, 1H, —NH), 9.39 (s, 1H, —OH), 8.48 (s, 1H, 2-H), 8.07 (s, 2H, 2',6'-H), 7.76 (s, 1H, 5-H), 7.17 (s, 1H, 8-H), 3.94 (s, 3H, — OCH₃), 3.91 (s, 3H, —OCH₃); IR (KBr) 3504,3419, 2868, 1627,1512,1425, 1250, 1155 cm⁻¹; GC/MS m/z 456 (M⁺+1, 54), 455 (M⁺, 100), 454 (M⁺−1, 78), 439 (M⁺—OH, 8), 376 (M⁺+1—Br, 10), 375 (M⁺—Br, 11), 360 (5); Anal. (C₁₆H₁₃Br₂N₃O₃) C, H, N.

4-(3'-Bromo-4'-methylphenyl)-amino-6,7-dimethoxyquinazoline WHI-P111: Yield 82.22%; mp 225.0–228° C.; $^1$H NMR(DMSO-d$_6$) d 10.23 (s, 1H, —NH), 8.62 (s, 1H, 2-H), 8.06 (d, 1H, J$_{2',6'}$=2.1 Hz, 2'-H), 7.89 (s, 1H, 5-H), 7.71 (dd, 1H, J$_{5',6'}$=8.7 Hz, J$_{2',6'}$=2.1 Hz, 6'-H), 7.37 (d, 1H, J$_{5',6'}$=8.7 Hz, 5'-H), 7.21 (s, 1H, 8-H), 3.96 (s, 3H, —OCH$_3$), 3.93 (s, 3H, —OCH$_3$), 2.33 (s, 3H, —CH$_3$); IR (KBr) 3431, 3248, 2835, 1633, 1517, 1441, 1281, 1155 cm$^{-1}$; GC/MS m/z 375 (M$^+$+1, 77), 374 (M$^+$, 100), 373 (M$^+$−1, 77), 358 (M$^+$+1—OH, 11), 357 (1), 356 (6); Anal. (C$_{17}$H$_{16}$BrN$_3$O$_2$.HCl) C, H, N.

4-(2',5'-Dibromophenyl)-amino-6,7-dimethoxyquinazoline WHI-P112: yield 70.05%; mp>300.0° C.; $^1$H NMR (DMSO-d6) d 11.51 (s, 1H, —NH), 8.76 (s, 1H, 2-H), 8.21 (s, 1H, 5-H), 7.81 (d, 1H, J$_{4',6'}$=2.4 Hz, 6'-H), 7.75(d, 1H, J$_{3',4'}$=8.7 Hz, 3'-H), 7.55 (dd, 1H, J$_{4',6'}$=2.4 Hz, J$_{3',4'}$=8.7 Hz, 4'-H), 7.33 (s, 1H, 8-H), 3.98 (s, 3H, —OCH$_3$), 3.97(s, 3H, —OCH$_3$); IR (KBr) 3444, 2836, 1628, 1510, 1431, 1277, 1070 cm$^{-1}$; GC/MS m/z 440 (M$^+$+1, 10), 439 (M+, 7), 438 (M$^+$−1, 4), 360 (M$^+$+1—Br, 99), 359 (M$^+$—Br, 20), 358 (M$^+$−1—Br, 100), 343(21), 299 (9); Anal. (C$_{16}$H$_{13}$Br$_2$N$_3$O$_2$.HCl) C, H, N.

4-(4'-Hydroxylphenyl)-amino-6,7-dimethoxyquinazoline WHI-P131: Yield 84.29%; mp 245.0–248.0° C.; $^1$H NMR (DMSO-d$_6$) d 11.21 (s, 1H, —NH), 9.70 (s, 1H, —OH), 8.74 (s, 1H, 2-H), 8.22 (s, 1H, 5-H), 7.40 (d, 2H, J=8.9 Hz, 2',6'-H), 7.29 (s, 1H, 8-H), 6.85 (d, 2H, J=8.9 Hz, 3', 5'-H), 3.98 (s, 3H, —OCH$_3$), 3.97 (s, 3H, —OCH$_3$); IR (KBr) 3428, 2836, 1635, 1516, 1443, 1234 cm$^{-1}$; GC/MS m/z 298 (M$^+$+1, 100), 297(M$^+$, 27), 296(M$^+$−1, 12); Anal. (C$_{16}$H$_{15}$N$_3$O$_3$,HCl) C, H, N.

4-(2'-Hydroxylphenyl)-amino-6,7-dimethoxyquinazoline WHI-P132: Yield 82.49%; mp 255.0–258.0° C. $^1$H NMR (DMSO-d$_6$) d 9.78 (s, 1H, —NH), 9.29 (s, 1H, —OH), 8.33 (s, 1H, 2-H), 7.85 (s, 1H, 5-H), 7.41–6.83 (m, 4H, 3', 4', 5', 6'-H), 7.16 (s, 1H, 8-H), 3.93 (s, 3H, — OCH$_3$), 3.92 (s, 3H, —OCH$_3$); IR(KBr) 3500, 3425, 2833, 1625, 1512, 1456, 1251, 1068 cm$^{-1}$; GC/MS m/z 298 (M$^+$+1, 9), 297 (M$^+$, 57), 281 (M$^+$+1—OH, 23), 280 (M$^+$—OH, 100); Anal. (C$_{16}$H$_{15}$N$_3$O$_3$.HCl) C, H, N.

4-(3'-Bromo-4'-hydroxylphenyl)-amino-6,7-dimethoxyquinazoline WHI-P154: Yield 89.90%; mp 233.0–233.5° C.; $^1$H NMR (DMSO-d$_6$) d 10.08 (s, 1H, —NH), 9.38 (s, 1H, —OH), 8.40 (s, 1H, 2-H), 7.89 (d, 1H, J$_{2',6'}$=2.7 Hz, 2'-H), 7.75 (s, 1H, 5-H), 7.55 (dd, 1H, J$_{5',6'}$=9.0 Hz, J$_{2',6'}$=2.7 Hz, 6'-H), 7.14 (s, 1H, 8-H), 6.97 (d, 1H, J$_{5',6'}$=9.0 Hz, 5'-H), 3.92 (s, 3H, —OCH$_3$), 3.90 (s, 3H, —OCH$_3$); IR (KBr) 3431, 2841, 1624, 1498, 1423, 1244 cm$^{-1}$; GC/MS m/z 378 (M$^+$+2, 91), 377 (M$^+$+1, 37), 376 (M$^+$, 100), 360 (M$^+$, 4), 298 (19), 282 (7); Anal. (C$_{16}$H$_{14}$BrN$_3$O$_3$.HCl) C, H, N.

4-(3'-hydroxyphenyl)-amino-6,7-dimethoxyquinazoline WHI-P180: was synthesized as described prevoiusly (Narla et al., 1998, Clin. Cance Res., 4:1405–1414.)

4-(Phenyl)-amino-6,7-dimethoxyquinazoline WHI-P258: Yield 88.26%; mp 258.0–260.0° C.; $^1$HNMR (DMSO-d$_6$) d 11.41 (s, 1H, —NH), 8.82 (s, 1H, 2-H), 8.32 (s, 1H, 5-H), 7.70–7.33 (m, 5H, 2', 3', 4', 5', 6'-H), 7.36 (s, 1H, 8-H), 4.02 (s, 3H, —OCH$_3$), 4.00 (s, 3H, —OCH$_3$); IR (KBr) 2852, 1627, 1509, 1434, 1248 cm$^{-1}$; GC/MS m/z 282(M$^+$+1, 11), 281 (M$^+$, 55), 280 (M$^+$−1, 100), 264 (16), 207 (9); Anal. (C$_{16}$H$_{15}$N$_3$O$_2$) C, H, N.

Example 4

JAK-3 Expression in Mast Cells

Expression of JAK-3 in mast cells was studied.

Materials and Methods:

Mice—Male C57BL/6 and Balb/c mice (6–8 weeks old) were purchased from Charles River Laboratories (Wilmington, Mass.). Breeder pairs of JAK3-null mice (Nosaka et. al., 1995) were obtained from Dr. J. Ihle (St. Jude Children's Research Hospital, Memphis, Tenn.). Animals were caged in groups of five in a pathogen free environment in accordance with the rules and regulations of U. S. Animal Welfare Act, and National Institutes of Health (NIH). Animal care and the experimental procedures were carried out in agreement with institutional guidelines.

Fetal bovine serum was obtained from Hyclone (Logan, Utah). Histopaque-1077, A23187, bovine serum albumin, toluidine blue, hydrogen peroxide, napthol AS-MX phosphate, fast blue RR, alcian blue, anti-human IgE, and dimethyl sulphoxide (DMSO) were purchased from Sigma (St. Louis, Mo.). Leukotriene (LT) C$_4$ ELISA kits were from Cayman Company (Ann Arbor, Mich.). Histamine ELISA kits were purchased from Immunotech (Westbrook, Me.). The preparation of dinitrophenyl (DNP)-BSA (Wei et. al., 1986, J. Immunol., 137:1993–2000), monoclonal anti-DNP-IgE (Liu et. al., 1980, J. Immunol., 124:2728–2737) and FcεRIa chain antibody, 22E7 (Riske et. al., 1991, J. Biol. Chem., 266:11245–11251) have been described. Recombinant hSCF and IL-4 were purchased from Genzyme (Cambridge, Mass.). Alkaline phosphatase labeled anti-tryptase antibody was purchased from Chemicon (Temecula, Calif.). Affinity purified JAK3 and STAT5 antibodies were purchased from Quality Control Biochemicals (Hopkins, Mass.). Anti-phosphotyrosine monoclonal antibody (Mab) was purchased from Upstate Biotechnology Inc. Human IgE was purchased from Calbiochem (San Diego, Calif.).

Mast Cell Cultures:

RBL-2H3 Cells: RBL-2H3 cells were a gift from Dr. Reuben P. Siraganian (Laboratory of Microbiology and Immunology, National Institute of Dental Research, National Institute of Health). The cells were maintained as monolayer cultures in 75- or 150-cm$^2$ flask in Eagle's essential medium supplemented with 20% fetal calf serum (Hamawy et. al., 1995, Cellular Signalling 7:535–544).

Mouse Mast Cells: Mast cells were cultured from the bone marrow specimens of JAK3-null (Jak3$^{-/-}$) and JAK3$^{30}$/+ control mice in a medium supplemented with 25% WEHI-3 cell supernatant for 3 weeks, as previously described (Malaviya et. al., 1993, J Biol. Chem., 268:4939–4944; Malaviya et. al., 1994a, J. Immunol., 152:1907–1914). Cell density was adjusted to 1×10$^5$ cells/ml on a weekly basis. After 3 weeks, mast cells were characterized by staining with toluidine blue and alcian blue. Mast cells show metachromatic granules after staining with toluidine blue, whereas alcian blue specifically stains mast cell granules containing chrondroitin sulfate.

Human Mast Cells: Cells from human fetal livers (16 to 21 weeks of gestational age) were cultured for 5 weeks in the presence of 50 ng/ml rhSCF, 2 ng/ml rhIL-4 (Xia et. al., 1997, J. Immunol., 159:2911–2921). Culture medium was replaced with fresh medium once a week for the first 2 weeks and twice a week thereafter. At the end of the 5 weeks, the fetal liver derived cell cultures contained >70% mast cells, based on tryptase staining (Irani et. al., 1989, J. Histochem. Cytochem, 37:1509–1515).

Confocol Microscopy: Staining of mast cells with primary and secondary antibodies followed by confocal laser scanning microscopy was performed as previously described in detail (Uckun et. al., 1998, *Clin. Cancer Res.*, 4:901–912). After staining with appropriate primary and secondary antibodies, cells were washed three times to remove unbound antibody. DNA labeling was performed by incubation of coverslips with toto-3 (Molecular Probes, Eugene, Oreg.) for 10 min. Excessive dye was washed with PBS-0.1% triton X-100. Cells were visualized under MRC 1024 Laser Scanning Microscope after mounting with Vectashield (Vector laboratories, Inc, Burlingame, Calif.). The anti-JAK3 (Witthuhn et. al., 1999, *Lymphoma Leukemia*, in press) and anti-tubulin (clone B-5-1-2, Sigma Chemicals, St. Louis. Mo.) antibodies were used according to standard procedures (Uckun, et. al., 1998, *Clin. Cancer Res.* 4:901–912).

Immune Complex Kinase Assays. Sf21 (IPLB-SF21-AE) cells (Vassilev et. al., 1999, *J. Biol. Chem*,. 274:1646–1656) derived from the ovarian tissue of the fall armyworm *Spodotera frugiperda*, were obtained from Invitrogen and maintained at 26–28° C. in Grace's insect cell medium supplemented with 10% FBS and 1.0% antibiotic/antimycotic (GIBCO-BRL). Stock cells were maintained in suspension at 0.2–1.6×10$^6$/ml in 600 ml total culture volume in 1 L Bellco spinner flasks at 60–90 rpm. Cell viability was maintained at 95–100% as determined by trypan blue dye exclusion.

Sf21 cells were infected with a baculovirus expression vector for BTK, SYK, JAK1, JAK2, or JAK3, as previously reported (Mahajan et. al., 1999, *J Biol. Chem.*, 274:1646–1656). The human B-lineage leukemia cell line NALM-6 and the EBV-transformed lymphoblastoid B-cell line KL-2 were maintained in RPMI 1640 medium supplemented with 10% heat-inactivated fetal bovine serum (Uckun et. al., 1996, *Science*, 273: 1096–1100; Uckun et. al., 1995, *Science*, 267:886–891). Cells were harvested, lysed (10 mM Tris pH 7.6, 100 mM NaCl, 1% Nonidet P-40, 10% glycerol, 50 mM NaF, 100 mM Na$_3$VO$_4$, 50 mg/ml phenylmethylsulfonyl fluoride, 10 mg/ml aprotonin, 10 mg/ml leupeptin), and the kinases were immunoprecipitated from the lysates, as reported (Vassilev et. al., 1999,*J Biol. Chem.*,. 724:1646–1656). Antibodies used for immunoprecipitations from insect cells are as follows: polyclonal rabbit anti-BTK serum, polyclonal rabbit anti-JAK1 (HR-785), cat# sc-277, polyclonal goat anti-JAK2 (C-20-G), cat.# sc-294-G, polyclonal rabbit anti-JAK3 (C-21), cat # sc-513, polyclonal rabbit anti-SYK (C-21) cat# sc-929 (Santa Cruz Biotechnology). Antibodies directed against BTK and LYN have been described previously (Mahajan et. al., 1995, *Mol. Cell. Biol.*, 15:5304–5311; Uckun et. al., 1996, *Science*, 273: 1096–1100; Uckun et. al., 1995, *Science*, 267:886–891; Uckun et. al., 1996a, *J. Biol. Chem*,. 271:6396–6397.; Vassilev et. al., 1999, *J. Biol. Chem.*, 274:1646–1656; Goodman et. al., 1998, *J. Biol. Chem.*, 273:17742–17748). Immune-complex kinase assays were conducted as described in these references. Kinase assays were performed following a 1 hour exposure of the immunoprecipitated tyrosine kinases to the test compounds, as described in detail elsewhere (Mahajan et. al., 1995, *Mol. Cell. Biol.*, 15:5304–5311; Uckun et. al., 1996, *Science*, 273:1096–1100). The immunoprecipitates were subjected to Western blot analysis as previously described (Uckun et. al., 1996, *Science*, 273: 1096–1100; Uckun et. al., 1996a, *J. Biol. Chem,*. 271:6396–6397; Vassilev et. al., 1999, *J. Biol. Chem.*, 274:1646–1656).

For insulin receptor kinase (IRK) assays, HepG2 human hepatoma cells grown to approximately 80% confluency were washed once with serum-free DMEM and starved for 3 hours at 37° in a CO$_2$ incubator. Subsequently, cells were stimulated with insulin (Eli Lilly, cat# CP-410;10 units/ml/10×10$^6$ cells) for 10 minutes at room temperature. Following this IRK activation step, cells were washed once with serum free medium, lysed in NP-40 buffer and IRK was immunoprecipitated from the lysates with an anti-IRb antibody (Santa Cruz. Cat.# sc-711. polyclonal IgG). Prior to performing the immune complex kinase assays, the beads were equilibrated with the kinase buffer (30 mM Hepes pH 7.4, 30 mM NaCl, 8 mM MgCl$_2$, 4 mM MnCl$_2$). LYN was immunoprecipitated from whole cell lysates of NALM-6 human leukemia cells as previously reported (Uckun et. al., 1995, *Science*, 267:886–891).

In JAK3 immune complex kinase assays (Goodman et. al., 1998,*J. Biol. Chem.*, 273:17742–17748; Witthuhn et. al., 1999, *Lymphoma Leukemia*, in press"; Mahajan, et. al., 1999, *J. Biol. Chem.*, in press). KL-2 EBV-transformed human lymphoblastoid B cells (native JAK3 kinase assays) or insect ovary cells (recombinant JAK3 kinase assays) were lysed with NP-40 lysis buffer (50 mM Tris, pH 8, 150 mM NaCl, 5 mM EDTA, 1% NP-40, 100 $\mu$M sodium orthovanadate, 100 $\mu$M sodium molybdate, 8 $\mu$g/ml aprotinin, 5 $\mu$g/ml leupeptin, and 500 $\mu$M PMSF) and centrifuged 10 minutes at 13000× g to remove insoluble material. Samples were immunoprecipitated with antisera prepared against JAK3. The antisera were diluted and immune complexes collected by incubation with 15 $\mu$l protein A Sepharose. After 4 washes with NP-40 lysis buffer, the protein A Sepharose beads were washed once in kinase buffer (20 mM MOPS, pH 7.0, 10 mM MgCl$_2$) and resuspended in the same buffer. Reactions were initiated by the addition of 25 $\mu$Ci $\gamma$[$^{32}$P] ATP (5000 Ci/mMole) and unlabeled ATP to a final concentration of 5 $\mu$M. Reactions were terminated by boiling for 4 min in SDS sample buffer. Samples were run on 9.5% SDS polyacrylamide gels and labeled proteins will be detected by autoradiography. Following electrophoresis, kinase gels were dried onto Whatman 3M filter paper and subjected to phosphoimaging on a Molecular Imager (Bio-Rad, Hercules, Calif.) as well as autoradiography on film. For each drug concentration, a kinase activity index (KA) was determined by comparing the kinase activity in phosphorimager units (PIU) to that of the baseline sample. In some experiments, cold kinase assays were performed, as described (Uckun et. al., 1998, *Clin. Cancer Res.*, 4:901–912).

Electrophoretic Mobility Shift Assays (EMSAs). EMSAs were performed to examine the effects of dimethoxyquinazoline compounds on cytokine-induced STAT activation (Goodman et. al., 1998). Specifically, 32Dc11/IL2R$\beta$ cells (gift from James Ihle, St. Jude Children's Research Hospital) were exposed at 8×10$^6$/ml in RPMI supplemented with FBS to WHI-P131. WHI-P154, or the control compound WHI-P132 at a final concentration of 10 $\mu$g/ml in 1% DMSO for 1 hour and subsequently stimulated with IL2 or IL3 as indicated in the text. Cells were collected after 15 minutes and resuspended in lysis buffer (100 mM Tris-HCl pH 8.0, 0.5% NP-40, 10% glycerol, 100 mM EDTA, 0.1 mM NaVO3, 50 mM NaF, 150 mM NaCl, 1 mM DTT, 3 $\mu$g/ml Aprotinin, 2 $\mu$g/ml Pepstatin A, 1 $\mu$g/ml Leupeptin and 0.2 mM PMSF). Lysates were precleared by centrifugation for 30 min. Cell extracts (approximately 10 $\mu$g) were incubated with 2 $\mu$g of poly(dI-dC) for 30 minutes, followed by a 30 minutes incubation with 1 ng of poly nucleotide kinase-$^{32}$P labeled double stranded DNA oligonucleotide representing the IRF-1 STAT DNA binding sequence (Santa Cruz Biotechnology, Santa Cruz, Calif.). Samples were resolved by non-denaturing PAGE and visualized by autoradiography.

Stimulation of Mast Cells: RBL-2H3 cells and bone marrow mast cells (BMMC) cultured from the bone marrow cells of JAK3$^{-/-}$ or JAK3$^{+/+}$ mice were sensitized with monoclonal anti-DNP IgE antibody (0.24 mg/ml) for 1 h at 37° C. in a 48-well tissue culture plate. RBL-2H3 cells were allowed to adhere to the plate, whereas BMMC were used in suspension. Unbound IgE was removed by washing the cells with phosphate buffered saline. After washing the BMMC were re-suspended in RPMI-hepes buffer whereas PIPES-buffered saline containing 1 mM calcium chloride was added to the monolayers of the RBL-2H3 cells. The cells were challenged with 20 ng/ml DNP-BSA for 30 minutes at 37° C. The plate was centrifuged at 200 g for 10 minutes at 4° C. Supernatants were removed and saved. The RBL-2H3 cell pellets were washed with phosphate buffered saline and solubilized in PIPES buffered saline containing 0.1% Triton X-100.

Fetal liver derived human mast cells were resuspended in tyrode buffer containing calcium and magnesium and challenged with anti-FcεRI antibody 22E7 for 15 minutes. In some experiments fetal liver derived human mast cells were re-suspended in culture medium at a cell density of 5×10$^6$/ml and sensitized with IgE (150 μg/ml) for 3 hours at 4° C. After sensitization the cells were washed with tyrode buffer containing calcium and magnesium and challenged with mouse monoclonal anti-human IgE (40 μg/ml) for 30 minutes at 37° C. To study the effects of the test compounds, mast cells were incubated with WHI-P131, WHI-P154, WHI-P111 or WHI-P112 at the indicated concentrations or vehicle for 1 hour prior to challenge.

Mediator Release Assays: Histamine content in cell free supernatants and in the solubilized cell pellets was estimated using a commercially available enzyme immunoassay (Malaviya et. at., 1996a, *J. Invest. Dermatol*, 106:785–789). Leukotriene (LT) C$_4$ levels were estimated in cell free supernatants by immunoassay (Malaviya et. al., 1993, *J Biol. Chem.*, 268:4939–4944). TNFα levels were estimated in cell free supernatants using a standard cytotoxicity assay (Malaviya et. al., 1996, *Nature*, 381: 77–80). In RBL-2H3 cells, β-hexosaminidase release was estimated in cell free supernatants and Triton X-100 solubilized pellets, as described (Ozawa et. al., 1993, *J Biol. Chem.*, 268:1749–1756). Tryptase levels were quantitated in cell free supernatants and pellets of fetal liver derived human mast cells as has been described in detail (Xia et. al., 1997, *J Immunol.*, 159:2911–2921).

Proliferation Assay: The proliferative responses of mast cells to SCF were determined using the MTT (3-[4,5-dimethylthiazol-2-yl]-2,5-diphenyl tetrazolium bromide) assay (Boehringer Mannheim Corp., Indianapolis, Ind.) (Uckun et. al., 1998, *Clin. Cancer Res.*, 4:901–912). Briefly wild-type and JAK3 null BMMC were cultured in 96-well tissue culture plates at a cell density of 0.1×10$^5$ cells/ml in 100 μl media in the presence and absence of 100 ng/ml SCF for 96 hours at 37° C. To each well 10 μl of MTT (final concentration, 0.5 mg/ml) was added, and the plates were incubated at 37° C. for 4 hours to allow formazan crystals to form by reacting with metabolically active cells. The formazan crystals were solubilized overnight at 37° C. in a solution containing 10% SDS in 0.01N-HCl. The absorbance of each well was measured in a microplate reader (Labsystems) at a wave length of 540 nm.

IgE Binding Assay: RBL-2H3 cells were incubated of 0.24 mg/ml monoclonal anti-DNP IgE antibody for 1 hour at 37° C. The cells were washed thoroughly three times with saline containing 1% BSA and labeled with 10 μg/ml anti-IgE-FITC (PharMingan Laboratories) for 30 minutes at 4° C. Following incubation the cells were washed were analyzed by flow cytometry.

Calcium Measurement: Calcium mobilization assay was performed as described earlier (Zhu et. al. 1998. *Clin. Cancer Res.*, 4:2967–2976). RBL-2H3 cells were loaded with Fluo-3 and stimulated with DNP-BSA in presence and absence of WHI-P131 as described above. Calcium response was measured by an calcium imaging device (Universal Imaging Co., West Chester, Pa.) mounted onto a inverted microscope. The exitation wavelength was 485 nm and the emission wavelength for detection was 535 nm. The fluorescent image of an individual cell was acquired by a CCD72 video camera (Dage-MTI Inc., Michigan City, Ill.) at the speed of 1 frame/s and digitized by computer.

Immune-Complex Kinase Assays and Western Blot Analyses of Mast Cell Lysates.

RBL-2H3 cells were stimulated as described above in the presence and absence of WHI-P131 for the indicated times. Cells were harvested, lysed (10 mM Tris pH 7.6, 100 mM NaCl, 1% Nonidet P-40, 10% glycerol, 50 mM NaF, 100 mM Na$_3$VO$_4$, 50 mg/ml phenylmethylsulfonyl fluoride, 10 mg/ml aprotonin, 10 mg/ml leupeptin), and the kinases were immunoprecipitated from the lysates, as reported (Uckun et. al., 1995, *Science*, 267:886–891; Uckun et. al., 1996, *Science*, 273:1096–1100). Antibodies directed against JAK3, STAT5, and SYK used for immunoprecipitations have been described previously (Uckun et. al. 1995, *Science*, 267:886–891; Uckun et. al., 1996, *Science*, 273:1096–1100; Witthuhn et. al. 1999, *Lymphoma Leukemia*, in press"; Mahajan et. al., 1999, *J. Biol. Chem.*, in press). Immunoprecipitations, and immunoblotting using the ECL chemiluminescence detection system (Amersham Life Sciences) were conducted as described previously (Uckun et. al., 1996, *Science*, 273:1096–1100).

Anaphylaxis Models: In order to examine the effect of WHI-P131 on passive cutaneous anaphylaxis in mice, dorsal sides of the ears of BALB/c mice were injected intradermally with 20 ng of DNP-IgE (left ears) or PBS (right ears) in 20 μL volume using a 30-gauge needle, as previously described (Miyajima et. al., 1997, *J Clin. Invest.*, 99:901–914). After 20 hours, mice were treated with WHI-P131 (10 or 25 mg/kg i.p.) twice at 1 hour intervals prior to the antigen challenge. Control mice were treated with an equal volume of vehicle. Thirty minutes after the last dose of WHI-P131 or vehicle, mice were challenged with 100 μg antigen (DNP-BSA) in 200 μl 2% Evans blue dye intravenously. Mice were sacrificed by cervical dislocation 30 minutes after the antigen challenge. For quantitation of Evans blue dye extravasation as a measure of anaphylaxis-associated vascular hyperpermeability, 8 mm skin specimens were removed from the ears of mice, minced in 2 ml formamide and incubated at 80° C. for 2 hours in water bath to extract the dye. The absorbance was read at 620 nm. The data were expressed as plasma exudation indices (i.e., times increase in optical density over PBS treated ears at 620 nm).

To induce passive systemic anaphylaxis, BALB/c mice were sensitized with 50 μg DNP-IgE intravenously. At 24 hours DNP-BSA (2 mg) was administered intravenously with 0.5% Evans blue (200 μl). For assessment of vascular leak, animals were sacrificed 30 minutes after the antigen challenge and their foot pads were examined for blue coloration. Histamine levels in plasma were measured 5 minutes after the antigen challenge. To this end, blood samples were obtained from the ocular venous plexus by retroorbital venupuncture and histamine levels were determined by ELISA using a commercial kit (Immnunotech, West Brook, Me., Malaviya et. al., 1996, *Nature*, 381:

77–80). For histopathologic evaluation of tissue mast cell degranulation, ears of mice were removed 1 hour after the DNP-BSA injection and fixed in 10 percent buffered formalin. Processed thin sections (3–5 μm) were stained with Avidin-FITC (6.25 μg/ml) for 2 hours, washed with PBS to remove unbound dye and then mounted in buffered glycerol, 30 mM triethylenediamine, pH 8.6 (Malaviya et. al., 1994, *J. Clin. Invest.* 93:1645–1653). In the murine model for antigen induced active anaphylaxis, mice were sensitized with 2 mg BSA in 200 μl aluminum hydroxide gel (Reheis Inc., Berkeley, N.J.). Ten days later anaphylactic shock was induced by the i.v. injection of the animals with 200 μg BSA.

Toxicity Studies in Mice. The toxicity profile of WHI-P131 in mice was examined, as previously reported for other new agents (Uckun et. al., 1995, *Science*, 267:886–891; Uckun et. al. 1998, *Clin. Cancer Res.,* 4:901–912). Female BALB/c mice were used and monitored daily for lethargy, cleanliness and morbidity. At the time of death, necropsies were performed and the toxic effects of WHI-P131 administration were assessed. For histopathologic studies, tissues were fixed in 10% neutral buffered formalin, dehydrated, and embedded in paraffin by routine methods. Glass slides with affixed 6 micron tissue sections were prepared and stained with Hemotoxylin and Eosin (H&E). Female BALB/c mice were administered an i.p. bolus injection of WHI-P131 in 0.2 ml PBS supplemented with 10% DMSO, or 0.2 ml PBS supplemented with 10% DMSO alone (control mice). No sedation or anesthesia was used throughout the treatment period. Mice were monitored daily for mortality for determination of the day 30 $LD_{50}$ values. Mice surviving until the end of the 30 days monitoring were sacrificed and the tissues were immediately collected from randomly selected mice, and preserved in 10% neutral buffered formalin. Standard tissues collected for histologic evaluation included: bone, bone marrow, brain, cecum, heart, kidney, large intestine, liver, lung, lymph node, ovary, pancreas, skeletal muscle, skin, small intestine, spleen, stomach, thymus, thyroid gland, urinary bladder, and uterus (as available).

Pharmacokinetic Studies: In pharmacokinetic studies, mice were injected either intravenously (i.v.) via the tail vein or intraperitoneally (i.p.) with a bolus dose of 300 μg/mouse (~12.5 mg/kg=34 μmols/kg) of WHI-P131. Blood samples were obtained from the ocular venous plexus by retroorbital venupuncture prior to and at 3 minutes, 5 minutes, 10 minutes, 15 minutes, 30 minutes, 45 minutes and 1 hour, 2 hours, 4 hours and 8 hours after administration of WHI-P131. All collected blood samples were heparinized and centrifuged at 7.000× g for 10 minutes in a microcentrifuge to obtain plasma. The plasma samples were stored at –20° C. until analysis. Aliquots of plasma were used for extraction and HPLC analysis. Pharmacokinetic modeling and pharmacokinetic parameter calculations were carried out using the pharmacokinetics software, WinNonline Program, Version 1.1. (Scientific Consulting Inc., Cary, N.C.). Concentration data were weighted by 1/concentration. An appropriate pharmacokinetic model was chosen on the basis of lowest weighted squared residuals, lowest Schwartz criterion (SC), lowest Akaike's Information Criterion (AIC) value, lowest standard errors of the fitted parameters, and dispersion of the residuals. The elimination half-life was estimated by linear regression analysis of the terminal phase of the plasma concentration profile. The area under the concentration time curve (AUC) was calculated by the trapezoidal rule between first (0 h) and last sampling time plus C/k, where C is the concentration of last sampling and k is the elimination rate constant. Systemic clearance (CL) was determined by dividing the dose by the AUC. The apparent volume of distribution at steady-state was calculated using the following equation, $V_{SS}$=Dose•AUMC/$(AUC)^2$. Bioavailability (F) was estimated using the equation $F(\%)=AUC_{ip} \times Dose_{iv}/AUC_{iv} \times Dose_{ip}$.

HPLC Analysis of Plasma WHI-P131 Levels: A highly sensitive quantitative HPLC detection method (Chen et. al., 1998, *J. Chromatography B* (*Biomedical sciences*), in press) was used to determine the pharmocokinetics of WHI-P131. In brief, the HPLC system consisted of a Hewlett Packard (HP) series 1100 equipped with an automated electronic degasser, a quaternary pump, an autosampler, an automatic thermostatic column compartment, diode array detector and a computer with a Chemstation software program for data analysis. A 250×4 mm Lichrospher 100, RP-18 (5 μm) analytical column and a 4×4 mm Lichrospher 100, RP-18 (5 μm) guard column were obtained from Hewlett Packard Inc. (San Fernando, Calif.). Acetonitrile/water containing 0.1% of trifluoroacetic acid (TFA) and 0.1% triethylamine (TEA) (28:72, v/v) was used as the mobile phase. The wavelength of detection was set at 340 nm. Peak width, response time and slit were set at >0.03 minutes, 0.5 seconds and 8 nm, respectively. For determination of WHI-P13 1 levels, 10 μL of internal standard WHI-P154 (50 μM) was added to a 100 μL plasma sample. For extraction, 7 ml chloroform was then added to the plasma sample, and the mixture was vortexed thoroughly for 3 minutes. Following centrifugation (300× g, 5 minutes), the aqueous layer was frozen using acetone/dry ice and the organic phase was transferred into a clean test tube. The chloroform extracts were dried under a slow steady stream of nitrogen. The residue was reconstituted in 100 μL of methanol: water (9:1) and 50 μL aliquot of this solution was used for HPLC analysis. Under the described chromatographic separation conditions, the retention times for WHI-P131 and WHI-P154 were 5.1 minutes and 9.5 minutes, respectively. At the retention time, WHI-P131 and its internal standard WHI-P154 were eluted without any interference peaks from the blank plasma.

Example 5

Expression and IgE Receptor/FcεRI-mediated Activation of Janus Kinase 3 in Mast Cells As shown in FIG. 4A, JAK3 is abundantly expressed in RBL-2H3 mast cells. This finding prompted us to examine the potential involvement of JAK3 in IgE receptor/FcεRI-mediated mast cell activation. Crosslinking of the IgE receptors on RBL-2H3 mast cells that were previously sensitized by a monoclonal anti-dinitrophenyl (DNP)-IgE antibody, with the specific antigen DNP-BSA resulted in rapid activation of JAK3 (FIG. 4B).

To elucidate the role of JAK3 in IgE receptor/FcεRI mediated mast cell responses, we cultured mast cells from the bone marrows of wild-type and JAK3-null mice ($Jak3^{-/-}$) that were generated by targeted disruption of Jak3 gene in embryonic stem cells (Nosaka et. al., 1995, *Science*, 270:800–802). Similar numbers of mast cells (range: 3.5–3.9×$10^5$ per $10^6$ nucleated bone marrow cells) were obtained from bone marrow specimens of $JAK3^{+/+}$ and $Jak3^{-/-}$ mice after 3 weeks of culture in medium supplemented with WEHI-3 cell supernatants (25% v/v). $JAK3^{-/-}$ mast cells showed typical mast cell staining characteristics towards alcian blue and toluidine blue (data not shown). When we compared the FcεRI receptor expression between $JAK3^{+/+}$ and $JAK3^{-/-}$ mast cells we found that $JAK3^{+/+}$ and $JAK3^{-/-}$ mast cells express similar levels of IgE receptor/FcεRI (FIG. 5A). Thus, JAK3 deficiency does not affect IgE receptor expression on mast cells. Fully differentiated mast cells express functional c-kit receptors and activation of c-kit receptor by its ligand, stem cell factor (SCF), triggers proliferation of mast cells (Dvorak et. al., 1994, *Am. J. Pathol.* 144:160–170). We compared the proliferative responses of JAK3$^{-/-}$ versus JAK3$^{+/+}$ mast cells to SCF using MTT assays. JAK3$^{+/+}$ or JAK3$^{-/-}$ mast cells at a cell density of 0.1×10$^5$ cells/ml, were incubated in the presence and absence of 100 ng/ml SCF for 96 hours at 37° C. At the end of the SCF incubation, virtually identical cell counts were obtained from cultures of JAK3$^{+/+}$ and JAK3$^{-/-}$ mast cells (FIG. 5B). Thus, JAK3 deficiency does not affect the in vitro proliferative responses of mast cells to SCF.

To further evaluate the potential role of JAK3 in mast cell responses, we next compared the IgE receptor/FcεRI mediated release of inflammatory/allergic mediators from JAK3$^{+/+}$ and JAK3$^{-/-}$ mast cells. Mast cells cultured from the bone marrows of JAK3$^{+/+}$ and JAK3$^{-/-}$ mice were sensitized with anti-DNP monoclonal IgE and challenged with DNP-BSA. The release of preformed granule-associated histamine, a marker for mast cell degranulation, was measured by comparing the histamine contents of the in cell free supernatants and cell pellets. The release of the arachidonic acid metabolite LTC$_4$, which serves as a marker for release of newly synthesized mediators, was estimated by determining the LTC$_4$ levels in cell free supernatants. Although the cellular histamine contents of JAK3$^{-/-}$ mast cells and JAK3$^{-+}$ mast cells were identical, JAK3$^{-/-}$ mast cells released approximately half of the amount of histamine released by JAK3$^{+/+}$ mast cells (FIG. 5C). LTC$_4$ release (FIG. 5D) after IgE receptor/FcεRI crosslinking was also substantially reduced with JAK3$^{-/-}$ mast cells. These results indicate that JAK3 plays an important role in IgE receptor/FcεRI-mediated mast cell responses. In agreement with these in vitro results, none of the BSA-sensitized Jak3$^{-/-}$ mice (N=3) showed an adverse reaction to a rechallenge with 200 μg BSA injected intraperitoneally in our active systemic anaphylaxis (ASA) model (Amir and English, 1991), whereas all BSA-sensitized JAK3$^{+/+}$ mice (N=5) developed a severe anaphylactic reaction within 10 minutes after BSA rechallenge under the same experimental conditions (data not shown). Taken together, these experiments provided unprecedented evidence that the IgE receptor/FcεRI-mediated activation of mast cells triggers a biochemical JAK3-activation signal which is important for pleiotropic biological mast cell responses to IgE receptor/FcεRI-engagement and hence for mast cell-mediated hypersensitivity reactions.

Example 6

Effects of Dimethoxy Quinozalines on JAK-3 Activity

We first used immune complex kinase assays to compare the effects of the synthesized dimethoxyquinazoline compounds on the enzymatic activity of human JAK3 immunoprecipitated from the KL2 EBV-transformed human lymphoblastoid B cell line. WHI-P131, WHI-P154, and WHI-P97, which had very similar estimated K$_i$ values ranging from 0.6 μM to 2.3 μM and were predicted to show significant JAK3 inhibitory activity at micromolar concentrations (which was not the case for the other compounds which had estimated K$_i$ values ranging from 25 μM to 72 μM), inhibited JAK3 in dose-dependent fashion. The measured IC$_{50}$ values were 9.1 μM for WHI-P131, 11.0 μM for WHI-P97, and 27.9 μM for WHI-P154, but >300 μM for all the other dimethoxyquinazoline compounds (Table 1). WHI-P131 and WHI-P154 were also tested against recombinant murine JAK3 expressed in a baculovirus vector expression system and inhibited JAK3 in a dose-dependent fashion with an IC$_{50}$ value of 23.2 μg/ml (~78 mM, FIG. 6A) and 48.1 μg/ml (~128 μM, FIG. 6B), respectively. The ability of WHI-P131 and WHI-P154 to inhibit recombinant JAK3 was confirmed in four independent experiments. These kinase assay results are consistent with our modeling studies described above.

Importantly, WHI-P131 and WHI-P154 did not exhibit any detectable inhibitory activity against recombinant JAK1 or JAK2 in immune complex kinase assays (FIGS. 6C & D). Electrophoretic Mobility Shift Assays (EMSAs) were also performed to confirm the JAK3 specificity of these dimethoxyquinazoline compounds by examining their effects on cytokine-induced STAT activation in 32Dc11/IL2Rβ cells. As shown in FIG. 6E, both WHI-P131 (10 μg/ml=33.6 μM) and WHI-P154 (10 μg/ml=26.6 μM) (but not the control compound WHI-P132, 10 μg/ml=33.6 μM) inhibited JAK3-dependent STAT activation after stimulation with IL-2, but they did not affect JAK1/JAK2-dependent STAT activation after stimulation with IL-3. Modeling studies suggest that this exquisite JAK3 specificity could in part be due to an alanine residue (Ala966) which is present in the catalytic site of JAK3 but changes to glycine in JAK1 and JAK2. This alanine group which is positioned near the phenyl ring of the bound dimethoxyquinazoline compounds can provide greater hydrophobic contact with the phenyl group and thus contribute to higher affinity relative to the smaller glycine residue in this region of the binding site in JAK1 and JAK2.

Example 7

Specificity of JAK-3 Inhibitors

Compound WHI-P131 was selected for further experiments designed to examine the sensitivity of non-Janus family protein tyrosine kinases to this novel dimethoxyquinazoline class of JAK3 inhibitors. The inhibitory activity of WHI-P131 against JAK3 was specific since it did not affect the enzymatic activity of other protein tyrosine kinases, including the ZAP/SYK family tyrosine kinase SYK, TEC family tyrosine kinase BTK, SRC family tyrosine kinase LYN, and receptor family tyrosine kinase IRK even at concentrations as high as 350 μM (FIG. 7).

A structural analysis of these PTK was performed using the crystal structures of HCK (Sicheri et. al. 1997) (which served as a homology model for LYN) IRK (Hubbard, 1997) and constructed homology models of JAK3, BTK, and SYK. This analysis revealed some nonconserved residues located in the catalytic binding site of the different tyrosine kinases which may contribute to the specificity of WHI-P131 (FIG. 3). One such residue which is located closest to the docked inhibitors is Ala966 in JAK3 (shown in region E in FIG. 5) which may provide the most favorable molecular surface contact with the hydrophobic phenyl ring of WHI-P131. The fact that WHI-P131 did not inhibit LYN, even though LYN contains the Ala residue conserved in JAK3 (Ala966), suggests that other factors (residue differences) contribute to this selectivity. Other nonconserved residues in the catalytic site of tyrosine kinases are shown in regions A to F (FIG. 5A). All of these differences in residues, especially residues which directly contact the bound inhibitor, may play an important role in the observed specificity of WHI-P131 for JAK3.

Example 8

Effects of JAK3 Inhibitors on In Vitro Mast Cell Responses

Figure 8A:
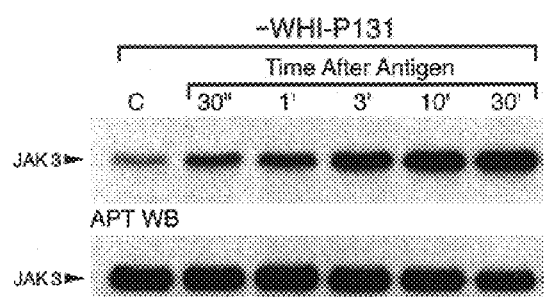
Figure 8B:
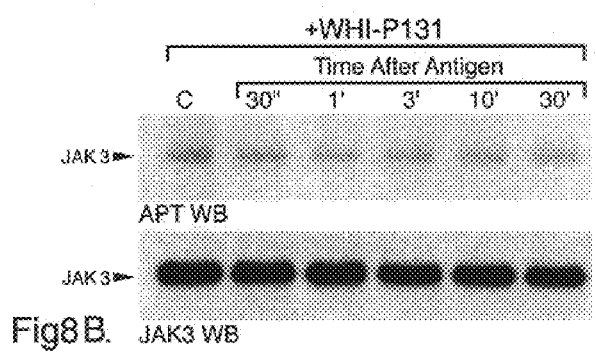
Figure 8C:
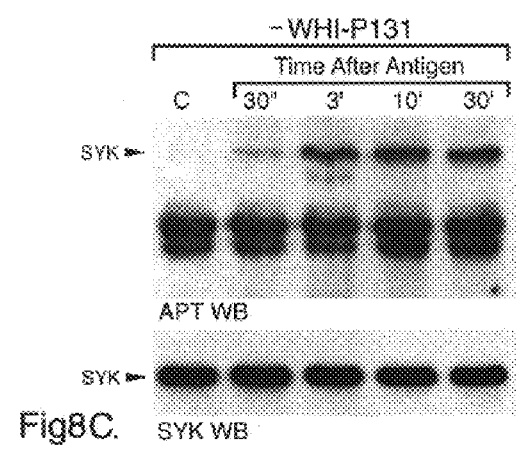
Figure 8D:
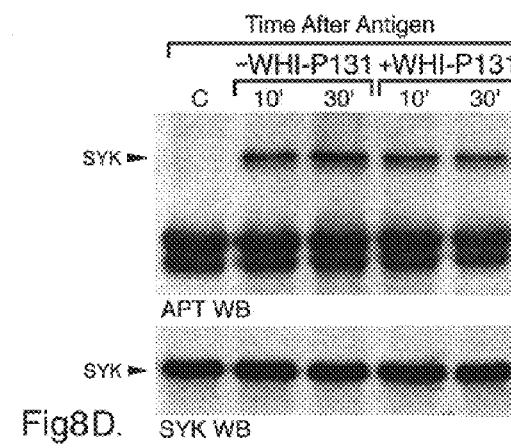

Treatment of the rat mucosal mast cell line RBL-2H3 with the JAK3-specific tyrosine kinase inhibitor WHI-P131 abrogated JAK3 activation after IgE receptor crosslinking (FIGS. 8A & B). Notably, WHI-P131 did not prevent SYK activation in RBL-2H3 mast cells after IgE receptor/FcϵRI crosslinking (FIGS. 8C & D). Therefore, any biologic consequences of JAK3 inhibition in WHI-P131-treated mast cells can not be attributed to impaired SYK activation.

Figure 9A:
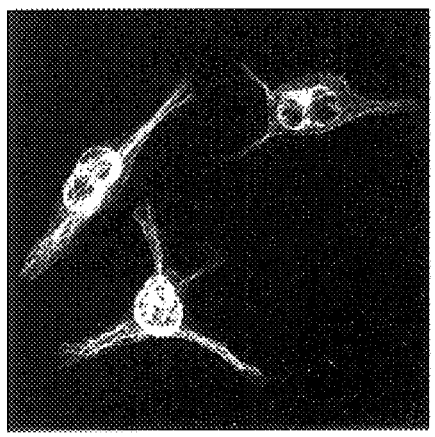
Figure 9B:
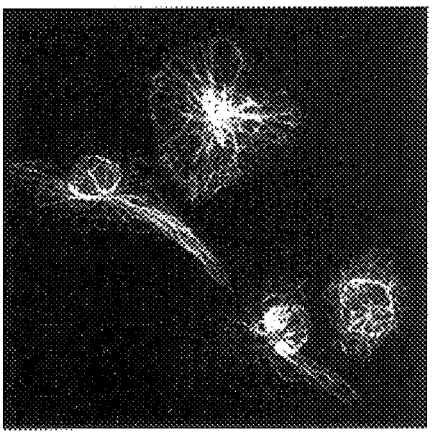
Figure 9C:
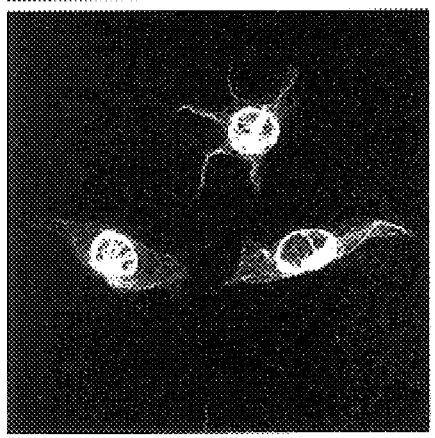
Figure 9D:
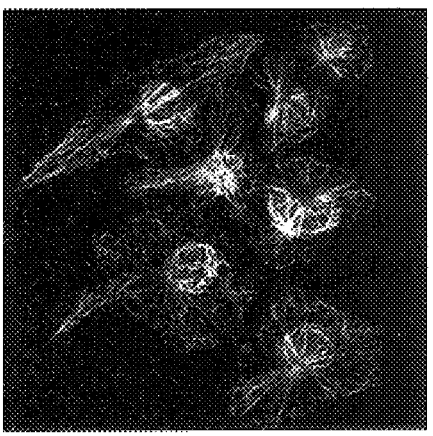
Figure 9E:
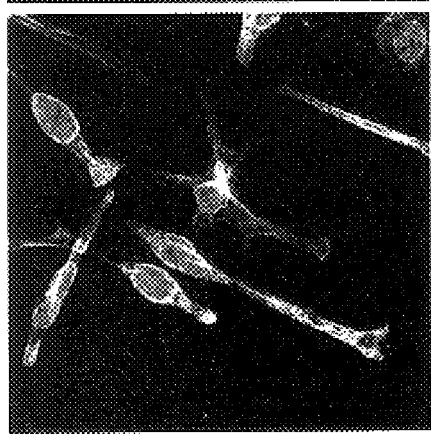
Figure 9F:
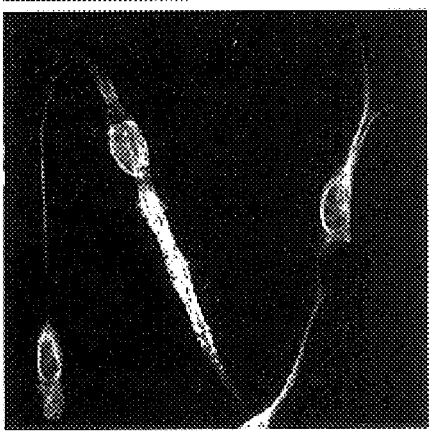
Figure 9G:
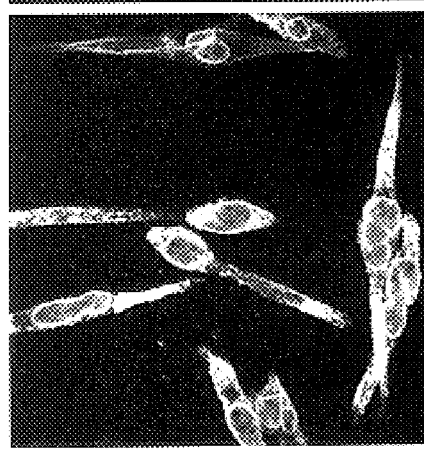
Figure 9H:
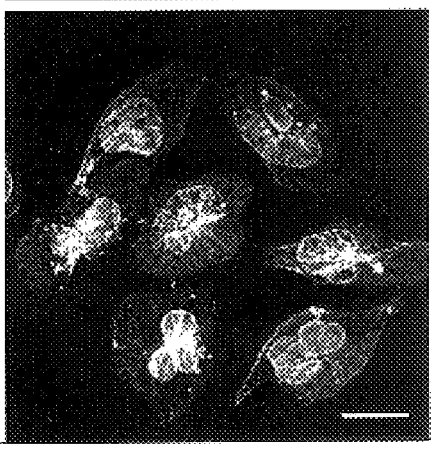

In a systematic effort aimed at elucidating the biologic consequences of JAK3 inhibition in mast cells, we first sought to determine if the JAK3 inhibitor WHI-P131 could prevent the IgE receptor/FcϵRI-mediated activation of mast cells. Since the IgE receptor/FcϵRI-mediated activation of mast cells results in a distinct morphologic transformation with marked cell spreading due to membrane ruffling, microtubule formation and actin polymerization (Apgar, 1997), we evaluated the effects of WHI-P131 on the activation-associated transformation of shape and surface topography of RBL-2H3 mast cells using confocal laser scanning microscopy (Ghosh et. al., 1998). The vast majority (95%) of unstimulated RBL-2H3 mast cells exhibited a spindle shape with arborized extensions and longitudinally oriented bundles of microtubules (FIG. 9A). Activation of RBL-2H3 mast cells by crosslinking their IgE receptors/FcϵRI using IgE/antigen induced a dramatic cell spreading response and 93% of cells assumed a flattened shape with a generalized microtubule organization throughout their cytoplasm (FIG. 9B). A two hour incubation with the JAK3 inhibitor WHI-P131 (but not the unsubstituted parent dimethoxyquinazoline compound WHI-P258, which lacks JAK3 inhibitory activity) at a concentration of 30 $\mu$M prevented the IgE/antigen-induced mast cell activation, as evidenced by markedly reduced spreading (23% flattened; 58% spindle shaped) and microtubule organization (FIGS. 9C–F). In contrast to WHI-P131, the bromo-substituted control dimethoxyquinazoline compound WHI-112. which does not inhibit JAK3, was unable to produce any significant effects on antigen induced mast cell spreading or microtubule organization (FIGS. 9G & H). In parallel, we tested the effect of the compounds on the viability of RBL-2H3 cells (as assessed by trypan blue dye exclusion test) under these experimental conditions and found that they do not affect cell viability up to 300 $\mu$M concentrations (data not shown).

Example 9

Effect on Calcium Mobilization

Since calcium influx is one of the earliest events in IgE receptor/FcϵRI-mediated mast cell activation (Millard et. al., 1989; Hamawy et. al., 1995), we also investigated whether $Ca^{2+}$ mobilization is affected by the JAK3 inhibitor WHI-P131. RBL-2H3 cells were sensitized with IgE and loaded with Fluo-3 prior to stimulation with DNP-BSA. The intracellular calcium ion concentration reached a maximum within 2–3 min after stimulation (FIG. 10) which is consistent with previous findings (Millard et. al., 1989; Wong et. al., 1992). In contrast, when RBL-2H3 cells were stimulated with DNP-BSA in presence of 30 $\mu$M WHI-P131, the calcium response was abrogated (FIG. 10). Thus, JAK3 is essential for IgE receptor/FcϵRI-mediated activation and calcium mobilization in mast cells. In contrast, ionomycin induced nonspecific mast cell calcium responses were not affected by WHI-P131 (FIG. 10).

Example 10

Mast Cell Degranulation and Mediator Release

In order to further examine the role of JAK3 in IgE receptor/FcϵRI-mediated mast cell activation and degranulation, we next assessed the effects of the JAK3 inhibitors WHI-P131 and WHI-P154 on mast cell degranulation and mediator release induced by IgE/antigen. WHI-P111 and WHI-P112, which do not inhibit JAK3, were included as controls. RBL-2H3 mast cells were preincubated with increasing concentrations of the test compounds or vehicle for 1 h before challenge with antigen (DNP-BSA). Stimulation of RBL-2H3 mast cells using IgE/antigen resulted in release of significant amounts of $\beta$-hexosaminidase (45.1±3.1% of total cellular content), $LTC_4$ (11.3±1.3 pg/$10^6$ cells), and TNFa (160±33.0 pg/$10^6$ cells). Notably, both JAK3 inhibitors, WHI-P131 and WHI-P154, prevented mast cell degranulation and release of preformed granule-associated $\beta$-hexosaminidase (FIG. 11A) as well as release of the newly synthesized arachidonic acid metabolite $LTC_4$ (FIG. 11B) and the proinflammatory cytokine TNFa (FIG. 11C) in a dose-dependent fashion with near to complete inhibition at $\geq$30 $\mu$M. Unlike these JAK3 inhibitors, the control dimethoxyquinazoline derivatives WHI-P111 and WHI-P112 lacking JAK3 inhibitory activity did not inhibit mast cell degranulation or mediator release after IgE receptor/FcϵRI crosslinking (FIGS. 11A–C).

The effect of WHI-P131 on RBL-2H3 was dependent on the presence of the drug and caused by an irreversible cytopathic effect of the drug preincubation because when the bulk of WHI-P131 was removed by repeated washing of the cells prior to antigen challenge, the inhibitory effect of the drug was significantly reduced (data not shown). Similar to these results obtained using the rat mast cell line RBL-2H3, treatment with the JAK3 inhibitor WHI-P131 markedly reduced IgE receptor/FcϵRI-mediated release of histamine and $LTC_4$ from mouse bone marrow mast cells as well (data not shown).

The effects of WHI-P131 on IgE receptor/FcϵRI mediated degranulation and mediator release from human mast cells was next examined. Fetal liver derived human mast cells were cultured in presence of SCF and IL-4 for 5 weeks. IgE-sensitized human mast cells were exposed to vehicle or increasing concentrations of WHI-P131 for 30 minutes. Human mast cells store the mast cell specific protease $\beta$-tryptase in their secretory granules (FIG. 12A) and the release of $\beta$-tryptase by degranulation is a specific marker for human mast cell activation (Hogan and Schwartz, 1997, *Methods*, 13:43–52). The FcϵRI receptors of fetal liver derived human mast cells were crosslinked with anti-IgE and the resulting mast cell degranulation (i.e., ϵ-tryptase) (Xia et. al., 1997, *J Immunol.*, 159:2911–2921) and $LTC_4$ release (Malaviya et. al., 1993, *J Biol. Chem.*, 268:4939–4944) were quantitated. WHI-P131 inhibited the release of ϵ-tryptase (FIG. 12B) as well as $LTC_4$ (FIG. 12C) from IgE/antigen stimulated human mast cells in a dose-dependent fashion.

In similar experiments, WHI-P180 effectively inhibited IgE/antigen induced mast cell degranulation, as measured by ϵ-hexasaminidase release, as well as secretion of newly synthesized mediators ($LTC_4$ release) WHI-P180 was much more potent than the unsubstituted dimethoxyquinazolines WHI-P258. (Chen et al., 1999, *Pharmac. Res.*, 16:117–122)

Taken together, these in vitro JAK3 inhibitor studies provided biochemical evidence confirming and extending the genetic evidence obtained using Jak3$^{-/-}$ mast cells that JAK3 in mast cells is a key regulator of IgE receptor/FcϵRI-mediated responses. The ability of the JAK3 inhibitor WHI-P131 to inhibit mast cell degranulation as well as mediator release after IgE receptor/FcϵRI crosslinking prompted us to further evaluate the potential of this compound as an anti-allergic agent.

Example 11

Effects of JAK3 Inhibitors on In Vivo Mast Cell Responses

WHI-P131 was not toxic to mice at intraperitoneal single bolus doses ranging from 0.5 mg/kg to 250 mg/kg. None of the 50 mice treated with WHI-P131 experienced side effects or died of toxicity during the 30 day observation period. In particular, we observed no hematologic side effects such as neutropenia, lymphopenia, or anemia at the tested dose levels. No histopathologic lesions were found in the organs of WHI-P131 treated mice that were electively killed at 30 days and there was no bone marrow hypoplasia or lymphoid cell depletion in spleen and lymph nodes. Thus, the maximum tolerated dose (MTD) of WHI-P131 was not reached at 250 mg/kg. We next examined the pharmacokinetic features of WHI-P131 in mice. A two-compartment pharmacokinetic model was fit to the pharmacokinetics data obtained following the intravenous (i.v.) (FIG. 13A) or intraperitoneal (i.p.) (FIG. 13B) administration of a single non-toxic 12.5 mg/kg bolus dose of WHI-P131. The estimated maximum plasma concentrations ($C_{max}$) of WHI-P131 were 85.6 $\mu$M after i.v. administration and 57.7 $\mu$M after i.p. administration, which are higher than the target effective concentration of 30 $\mu$M, at which WHI-P131 abrogates mast cell responses in vitro. WHI-P131 demonstrated rapid absorption after i.p. administration (estimated bioavailability: 94.4%) with an absorption half-life of 0.10 h, and the time to reach maximum plasma WHI-P131 concentration was 0.17 hours. WHI-P131 also had a rapid elimination rate with a β-half-life of 2.1 hours after i.v. administration and 1.9 hour after i.p. administration.

Example 12

Murine Models of Anaphylaxis

Taken together, these studies prompted the hypothesis that effective mast cell inhibitory plasma concentrations of WHI-P131 can be achieved in vivo in mice receiving non-toxic doses of this potent JAK3 inhibitor. To test this hypothesis, the effects of WHI-P131 in murine models of anaphylaxis were determined. Increased vascular permeability induced by mast cell mediators, such as histamine and leukotrienes, is a hallmark of anaphylaxis (Oettgen et. al., 1994, *Nature*, 370:367–370; Miyajima et. al., 1997, *J. Clin. Invest.*, 99:901–914).

Therefore, the effect of the JAK3 inhibitor WHI-P131 on vascular permeability was first examined in a well-characterized murine model of passive cutaneous anaphylaxis (Miyajima et. al., 1997, *J. Clin. Invest.*, 99:901–914). WHI-P131 inhibited the IgE/antigen induced plasma exudation, as measured by extravasation of systemically administered Evan's blue dye, in mice that had been pre-sensitized with antigen specific IgE by 70% at the 25 mg/kg nontoxic dose level (FIG. 14A).

Next, the effect of WHI-P131 on passive systemic anaphylaxis was studied in mice (Amir and English, 1991, *Eur. J. Pharmacol.*, 203:125–127; Oettgen et. al., 1994, *Nature*, 370:367–370; Miyajima et. al., 1997, *J Clin. Invest.*, 99:901–914). Mice were sensitized intravenously with 50 $\mu$g anti DNP-IgE. Twenty four hours later, drug or vehicle-treated animals were challenged with 2 mg DNP-BSA systemically in presence of 0.5% Evans blue dye to document the increased vascular permeability. Plasma exudation was assessed by blue coloring of foot pads 30 min after the antigen challenge (Oettgen et. al., 1994, *Nature*, 370:367–370). Vehicle-treated control mice showed a marked blue coloring of their foot pads after antigen challenge but no significant blue coloring was observed in mice pretreated with the JAK3 inhibitor WHI-P131 (FIG. 14B).

Mast cell degranulation in histologic sections of ears was also assessed by examining their fluorescence intensity after staining with avidin-FITC. Avidin specifically binds to heparin, the major proteoglycan in the granules of connective tissue mast cells (Malaviya et. al., 1994, *J Clin. Invest.*, 93:1645–1653). The fluorescence intensity of the stained mast cells is proportional to the amount of heparin and therefore degranulation reduces the fluorescence intensity. Whereas the IgE/antigen challenge resulted in a marked reduction of fluorescence intensity of avidin-FITC stained tissue mast cells of control mice consistent with degranulation-associated depletion of heparin, no reduction in fluorescence intensity was observed for mast cells from WHI-P131 pretreated mice (FIG. 14C). Since the major vasoactive mediator released from activated mast cells is histamine, and systemic anaphylaxis in humans and rodents has been associated with a significant increase in blood histamine levels (Oettgen et. al., 1994, *Nature*, 370:367–370; Miyajima et. al., 1997, *J Clin. Invest.* 99:901–914), blood samples were obtained from mice 5 minutes after the antigen challenge to determine their plasma histamine levels (Malaviya et. al., 1996a, *J. Invest. Deermatol*, 106:785–789). As expected, the antigen challenge resulted in marked elevation of plasma histamine levels, but pretreatment with the JAK3 inhibitor WHI-P131 substantially reduced this histamine response (FIG. 14D). These results demonstrate that WHI-P131 is capable of preventing passive cutaneous and systemic anaphylaxis by blocking mast cell degranulation in vivo.

The efficacy of WHI-P131 was next tested in a model of IgE/antigen-induced active systemic anaphylaxis. To this end, mice were first injected with BSA in an aluminum hydroxide gel to trigger a BSA-specific IgE response. Ten days later, these BSA-sensitized mice were rechallenged with this antigen to induce anaphylaxis. Eight of 15 (53%) BSA-sensitized mice that were treated with WHI-P131 prior to antigen challenge survived without any signs of anaphylaxis, whereas 12 of 12 control mice (100%) developed anaphylaxis within 45 minutes after antigen challenge (P<0.0001 by log-rank test; FIG. 14E).

CONCLUSION

In summary, the studies detailed herein provide experimental evidence that JAK3, a member of Janus family protein tyrosine kinases, plays a pivotal role in IgE receptor-mediated mast cell responses. Furthermore, the data demonstrate that targeting JAK3 in mast cells with WHI-P131 [4-(4'-hydroxylphenyl)-amino-6,7-dimethoxyquinazoline], a potent and specific inhibitor of JAK3, abrogates mast cell degranulation and release of allergic mediators in vitro and, at nontoxic dose levels, prevents IgE receptor/FcεRI mediated anaphylactic reactions, including fatal anaphylactic shock, in vivo.

Studies employing chimeric receptors and chimeric JAKs support the notion that JAKs act primarily as conduits of signal transmission by an authoritative cytokine receptor (Nelson et. al., 1996, *Mol. Cell. Biol.*, 16:369–375). Recent studies suggest that individual JAKs may also have distinct functions and promote unique signals by selectively recognizing specific substrates (Endo et. al., 1997, *Nature*, 387:921–924; Witthuhn et. al., 1999, *Lymphoma Leukemia*, in press"). Janus kinase JAK3 has been shown to play an important role for lymphocyte development, activation, and cytokine responsiveness (Ihle and Kerr, 1995. *Trends Genet,* 11:69–74; Nosaka et. al., 1995, *Science,* 270:800–802). The present study expands knowledge of JAK3 functions and reveals that JAK3 has essential and non-redundant functions for the full signaling capacity of the high affinity IgE receptor on mast cells. This previously unknown function of JAK3 provides a basis for new and effective treatment as well as prevention programs for mast cell mediated allergic reactions using JAK3 inhibitors. Based on the data presented herein and previous reports regarding the known function of Syk in IgE receptor/FcεRI mediated responses (Costello, et. al. 1996, *Oncogene,* 13:2595–2605; Oliver, et. al., 1994, *J Biol Chem.* 269:29697–29703), JAK3 and Syk may cooperate in initiation of mast cell mediated hypersensitivity reactions.

Intriguingly, SYK is also activated by cytokines, such as IL-2, IL-3, and GMCSF, known to also activate the JAK/STAT pathway and is capable of phosphorylating STATs (Matsuda and Hirano, 1994, *Blood,* 83: 3457–3461). Similarly, JAK3 can modulate the function of the Syk substrate P13-kinase via phosphorylation of the insulin receptor substrate proteins IRS1 and IRS2 (Johnston et. al., 1995, *J. Biol. Chem.,* 270:28527–30; Yamauchi et. al., 1998, *J Biol. Chem.* 273:15719–15726). Another possible mechanism for crosstalk may be through JAK3 interactions with Sam68, a Src substrate which associates with the SYK substrates PLCγ, PI3-kinase, Grb2, and Cb1 as well (Yin et. al., 1995, *J Biol. Chem.* 270:20497–502; Fusaki et. al., 1997, *J Biol. Chem.* 272:6214–6219; Deckert et. al., 1998, *J. Biol. Chem.,* 273:8867–8874).

This investigation extends earlier studies on the role of PTK in mast cell responses (Blank et. al., 1989, *Nature,* 337:187–189; Oliver et. al., 1994, *J Biol Chem.* 269:29697–29703; Hamawy et. al., 1995, *Cellular Signalling* 7:535–544; Scharenberg et. al., 1995, *EMBO J.,* 14:3385–3395; Costello et. al., 1996, *Oncogene,* 13:2595–2605) and offers new evidence supporting the therapeutic potential of PTK inhibitors in the treatment of allergic disorders. Because of its in vivo potency and lack of systemic toxicity, WHI-P131 and structural analogs that fit the binding pocket model, are not only the first JAK3-specific PTK inhibitors but also the first PTK inhibitors to modulate mast cell functions both in vitro and in vivo, and offer a new and effective treatment for mast cell mediated hypersensitivity reactions in clinical settings.

What is claimed is:

1. A therapeutic method comprising treating a pathology wherein JAK-3 kinase activation is implicated and inhibition of JAK-3 kinase activation is desired by administering a JAK-3 inhibitor to a mammal in need of such therapy.

2. The method of claim 1, wherein the JAK-3 inhibitor is one or more of:
(P131) 4-(4'-Hydroxylphenyl)-amino-6,7-dimethoxyquinazoline;
(P97) 4-(3',5'-dibromo-4'-hydroxy phenyl)-6,7-dimethoxyquinazoline;
(P154) 4-(3'-bromo-4'-hydroxylphenyl)-amino-6,7-dimethoxyquinazoline; or
(P180) 4-(3'-hydroxyphenyl)-amino-6,7-dimethoxyquinazoline.

3. The method of claim 1 wherein the administration occurs prior to onset of the pathology.

4. The method of claim 1 wherein the administration occurs after onset of the pathology.

5. The method of claim 1 wherein the JAK-3 inhibitor is a compound of formula I:

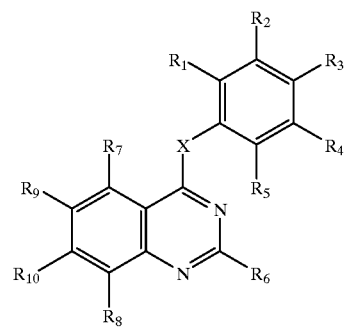

wherein
X is HN, $R_{11}$N, S, O, $CH_2$, or $R_{11}$CH;
$R_{11}$ is hydrogen, $(C_1-C_4)$alkyl, or $(C_1-C_4)$alkanoyl;
$R_1-R_8$ are each independently hydrogen, hydroxy, mercapto, amino, nitro, $(C_1-C_4)$alkyl, $(C_1-C_4)$alkoxy, $(C_1-C_4)$alkylthio, or halo; wherein two adjacent groups of $R_1-R_5$ together with the phenyl ring to which they are attached may optionally form a fused ring, for example forming a naphthyl or a tetrahydronaphthyl ring; and further wherein the ring formed by the two adjacent groups of $R_1-R_5$ may optionally be substituted by 1, 2, 3, or 4 hydroxy, mercapto, amino, nitro, $(C_1-C_4)$alkyl, $(C_1-C_4)$alkoxy, $(C_1-C_4)$alkylthio, or halo; and
$R_9$ and $R_{10}$ are each independently hydrogen, $(C_1-C_4)$alkyl, $(C_1-C_4)$alkoxy, halo, or $(C_1-C_4)$alkanoyl; or $R_9$ and $R_{10}$ together are methylenedioxy or $R_9$ and $R_{10}$ can independently be a producing derivative; or a pharmaceutically acceptable salt thereof.

6. The method of claim 1, wherein the JAK3 inhibitor is a compound of formula II:

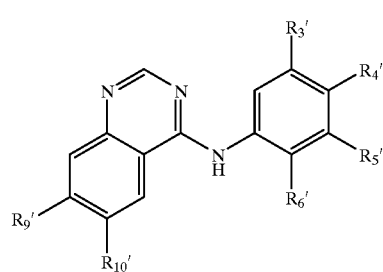

where:
R3' is H or halo
R4' is H or OH
R5' is OH
R6' is H, OH, $NO_2$, $NH_2$, $CH_2OH$
R9' and R10' are $R_9$ and $R_{10}$ are each independently hydrogen, $(C_1-C_4)$alkyl, $(C_1-C_4)$alkoxy, halo, or $(C_1-C_4)$alkanoyl; or $R_9$ and $R_{10}$ together are methylenedioxy or $R_9$ and $R_{10}$ can independently be a producing derivative; or a pharmaceutically acceptable salt thereof.

7. The method of claim 1, wherein the JAK3 inhibitor is a compound of formula III:

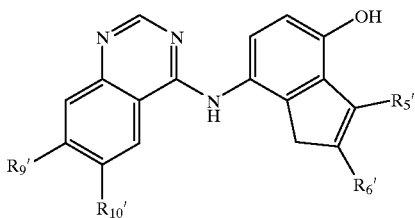

(III)

where:

R4' is OH

R5' is halo

R9' and R10' are $R_9$ and $R_{10}$ are each independently hydrogen, $(C_1-C_4)$alkyl, $(C_1-C_4)$alkoxy, halo, or $(C_1-C_4)$alkanoyl; or $R_9$ and $R_{10}$ together are methylenedioxy or $R_9$ and $R_{10}$ can independently be a pro-ducing derivative; or a pharmaceutically acceptable salt thereof.

8. The method of claim 1, wherein the JAK3 inhibitor is a compound of formula IV:

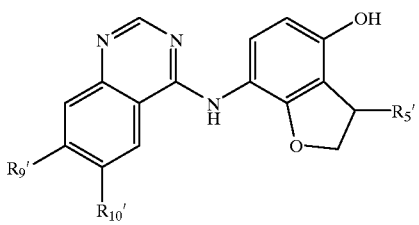

(IV)

where:

R5' is halo, OH, $NH_2$, $NO_2$, $CH_2OH$

R9' and R10' are $R_9$ and $R_{10}$ are each independently hydrogen, $(C_1-C_4)$alkyl, $(C_1-C_4)$alkoxy, halo, or $(C_1-C_4)$alkanoyl; or $R_9$ and $R_{10}$ together are methylenedioxy; or a pharmaceutically acceptable salt thereof.

9. The method of claim 1 is a compound of formula V:

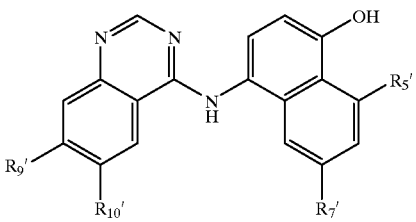

(V)

where:

R5' is halo

R7' is halo, OH, $NH_2$, $NO_2$, $CH_2OH$

R9' and R10' are $R_9$ and $R_{10}$ are each independently hydrogen, $(C_1-C_4)$alkyl, $(C_1-C_4)$alkoxy, halo, or $(C_1-C_4)$alkanoyl; or $R_9$ and $R_{10}$ together are methylenedioxy; or a pharmaceutically acceptable salt thereof.

10. The method of claim 1 wherein the mammal is a human.

11. The method of claims 5, wherein said inhibitor is conjugated to an antibody for targeted delivery.

* * * * *